(12) United States Patent
Ujikawa et al.

(10) Patent No.: US 8,937,055 B2
(45) Date of Patent: Jan. 20, 2015

(54) HETEROCYCLIC RING COMPOUND HAVING MUSCLE CELL OR ADIPOCYTE DIFFERENTIATION REGULATING ACTION

(75) Inventors: Osamu Ujikawa, Kanagawa (JP); Kazuaki Takami, Kanagawa (JP); Nobuyuki Takakura, Kanagawa (JP); Nozomu Sakai, Kanagawa (JP)

(73) Assignee: Takeda Pharmaceutical Company Limited, Osaka (JP)

( * ) Notice: Subject to any disclaimer, the term of this patent is extended or adjusted under 35 U.S.C. 154(b) by 0 days.

(21) Appl. No.: 13/810,021

(22) PCT Filed: Jul. 14, 2011

(86) PCT No.: PCT/JP2011/066153
§ 371 (c)(1),
(2), (4) Date: Jan. 14, 2013

(87) PCT Pub. No.: WO2012/008549
PCT Pub. Date: Jan. 19, 2012

(65) Prior Publication Data
US 2013/0116214 A1    May 9, 2013
US 2013/0296276 A2    Nov. 7, 2013

(30) Foreign Application Priority Data

Jul. 15, 2010  (JP) ................................ 2010-160240

(51) Int. Cl.
| | | |
|---|---|---|
| *A01N 57/00* | (2006.01) | |
| *A61K 31/675* | (2006.01) | |
| *C07F 9/58* | (2006.01) | |
| *A61K 31/4418* | (2006.01) | |
| *A61K 31/4439* | (2006.01) | |
| *A61K 31/506* | (2006.01) | |
| *A61K 31/5377* | (2006.01) | |
| *C07D 213/56* | (2006.01) | |
| *C07D 401/12* | (2006.01) | |
| *C07D 413/12* | (2006.01) | |

(52) U.S. Cl.
CPC ............ *C07F 9/582* (2013.01); *A61K 31/4418* (2013.01); *A61K 31/4439* (2013.01); *A61K 31/506* (2013.01); *A61K 31/5377* (2013.01); *A61K 31/675* (2013.01); *C07D 213/56* (2013.01); *C07D 401/12* (2013.01); *C07D 413/12* (2013.01)
USPC .............. 514/86; 514/89; 514/336; 514/337; 514/338; 514/339; 514/340; 514/341; 514/342; 514/343; 514/256; 544/243; 544/333; 544/335; 546/268.1; 546/268.4; 546/269.1; 546/276.4; 546/329; 546/22

(58) Field of Classification Search
USPC ................ 544/242, 333, 335; 546/269.1, 337
See application file for complete search history.

(56) References Cited

U.S. PATENT DOCUMENTS

| | | | |
|---|---|---|---|
| 7,115,750 | B1 | 10/2006 | Kato et al. |
| 7,592,373 | B2 * | 9/2009 | Lehmann-Lintz et al. ... 514/613 |
| 2004/0058903 | A1 | 3/2004 | Takasugi et al. |
| 2004/0077557 | A1 | 4/2004 | Ali et al. |
| 2004/0138301 | A1 | 7/2004 | Hansen et al. |
| 2004/0152742 | A1 * | 8/2004 | Stenkamp et al. ............ 514/352 |
| 2005/0137243 | A1 | 6/2005 | Souers et al. |
| 2005/0154020 | A1 | 7/2005 | Marzabadi et al. |
| 2005/0215495 | A1 | 9/2005 | Alihodzic et al. |
| 2005/0267093 | A1 | 12/2005 | Lehmann-Lintz et al. |
| 2005/0277638 | A1 | 12/2005 | Souers et al. |
| 2006/0128662 | A1 | 6/2006 | Tagmose et al. |
| 2006/0211636 | A1 | 9/2006 | Alihodzic et al. |
| 2006/0229265 | A1 | 10/2006 | Milburn et al. |

(Continued)

FOREIGN PATENT DOCUMENTS

| | | |
|---|---|---|
| WO | 01/21577 | 3/2001 |
| WO | 02/22122 | 3/2002 |

(Continued)

OTHER PUBLICATIONS

J.H. Poupaert, Drug Design: Basic Principles and Applications, in 2 Encyclopedia of Pharmaceutical Technology 1362-1369, 1367 (James Swarbrick ed., 3rd ed., 2007).*

(Continued)

*Primary Examiner* — James O Wilson
*Assistant Examiner* — Alexander R Pagano
(74) *Attorney, Agent, or Firm* — Wenderoth, Lind & Ponack, L.L.P.

(57) ABSTRACT

The present invention provides a compound having a muscle cell or adipocyte differentiation regulating action, useful for the prophylaxis or treatment of diseases such as diabetes, obesity, dyslipidemia and the like, and the like, and having superior efficacy.

The present invention provides a compound represented by the formula:

(I)

[Chemical structure showing a pyridine ring with substituent A (phenyl), X, connected via $L^1$ to a carbonyl-N($R^1$)-phenyl group bearing $Y$—$L^2$—$R^2$]

wherein each symbol is as defined in the description, or a salt thereof.

11 Claims, No Drawings

(56) References Cited

U.S. PATENT DOCUMENTS

| | | |
|---|---|---|
| 2006/0276393 A1 | 12/2006 | Milburn et al. |
| 2006/0292099 A1 | 12/2006 | Milburn et al. |
| 2007/0014833 A1 | 1/2007 | Milburn et al. |
| 2007/0149466 A1 | 6/2007 | Milburn et al. |
| 2007/0173498 A1 | 7/2007 | Kato et al. |
| 2008/0249137 A1 | 10/2008 | Lin et al. |
| 2010/0016272 A1 | 1/2010 | Strobel et al. |
| 2010/0016337 A1 | 1/2010 | Strobel et al. |
| 2010/0113536 A1 | 5/2010 | Petersen et al. |
| 2013/0296276 A2 * | 11/2013 | Ujikawa et al. ............ 514/89 |

FOREIGN PATENT DOCUMENTS

| | | |
|---|---|---|
| WO | 02/28835 | 4/2002 |
| WO | 02/50091 | 6/2002 |
| WO | 2004/039764 | 5/2004 |
| WO | 2004/041256 | 5/2004 |
| WO | 2005/063239 | 7/2005 |
| WO | 2005/069834 | 8/2005 |
| WO | 2006/090756 | 8/2006 |
| WO | 2007/008548 | 1/2007 |
| WO | 2007/030567 | 3/2007 |
| WO | 2008/021388 | 2/2008 |
| WO | 2008/074413 | 6/2008 |
| WO | 2008/077507 | 7/2008 |

OTHER PUBLICATIONS

B.A. Chabner et al., Chemotherapy of Neoplastic Diseases, Neoplastic Agents in, Goodman & Gilman's: The Pharmacological Basis of Therapeutics 1315-1403, 1315 (L.L. Brunton et al., eds., 11th ed., 2006).*

International Search Report issued Sep. 20, 2011 in International (PCT) Application No. PCT/JP2011/066153.

Seok Won Park, et al., "*Decreased Muscle Strength and Quality in Older Adults with Type 2 Diabetes*", The Health, Aging, and Body Composition Study, Diabetes, vol. 55, Jun. 2006, pp. 1813-1818.

Maria Pedersen et al., "*Circulating levels of TNF-alpha and IL-6-relation to truncal fat mass and muscle mass in healthy elderly individuals and in patients with type-2 diabetes*", Mechanisms of Ageing and Development, 2003, vol. 124, pp. 495-502.

Registered compounds list, STN Search, 2010.

Supplementary European Search Report isued Aug. 16, 2013 in corresponding European Application No. 11 80 6879.

* cited by examiner

HETEROCYCLIC RING COMPOUND HAVING MUSCLE CELL OR ADIPOCYTE DIFFERENTIATION REGULATING ACTION

TECHNICAL FIELD

The present invention relates to a novel heterocyclic compound having superior properties as a medicament and use thereof. More particularly, the present invention relates to a heterocyclic compound having a muscle cell or adipocyte differentiation regulating action, and various pharmacological actions based on promotion of myoblast differentiation, suppression of adipocyte differentiation, or inhibition of NF-kB activation, and useful as an agent for the prophylaxis or treatment of diseases associated with the differentiation regulation of muscle cell or adipocyte, such as diabetes, obesity, dyslipidemia and the like, or a salt thereof, or a prodrug thereof, and use thereof and the like.

BACKGROUND OF THE INVENTION

Myoblast differentiation, adipocyte differentiation and NF-kB activation are considered to play an important role in various diseases. For example, in diseases such as diabetes, obesity, dyslipidemia and the like, it is considered that suppression of myoblast differentiation, promotion of adipocyte differentiation, or promotion of NF-kB activation is involved in the onset and aggravation of the diseases. In fact, obesity wherein adipose tissue amount has increased is a risk factor of diabetes, hypertension, dyslipidemia and the like, and it has been reported that muscle mass decreases in diabetes and obesity. Diabetes (2006)55, 1813-1818 (non-patent document 1) describes that type 2 diabetes patients show decreased muscle mass, and Mechanisms of Ageing and Development (2003)124, 495-502 (non-patent document 2) teaches that obesity of body trunk and decrease of muscle mass are related. It has also been reported that the muscle mass increases when NF-kB pathway is suppressed by a proteasome inhibitor.

Skeletal muscles, which are present in human in not less than 600, are tissues occupying the largest proportion of the body weight, and consume sugar by insulin stimulation. On the other hand, obesity is a condition showing an increased amount of adipose tissue, and it is considered that metabolic disorder or organ damage occur due to insulin resistance caused by decreased adiponectin secretion and promoted secretion of inflammatory cytokines such as TNF-α and the like from obese adipocyte, and the like, and the like. Therefrom, increase of muscle mass and suppression of adipocyte differentiation are considered to be useful for the improvement of glycolipid metabolism.

Steroid hormone is known to increase the muscle mass. However, steroid hormone is also known to cause various side effects. While use of a myostatin antibody and a soluble receptor of activin, which is a myostatin receptor, to increase the muscle mass is being studied, it has not been put to practical use. In addition, an adipocyte differentiation suppressive action of a steroid hormone, a myostatin antibody or a soluble receptor of activin has not been reported.

There is still a high need for an agent for the prophylaxis or treatment of diabetes, obesity, dyslipidemia and the like, and the development of a strong therapeutic drug with fewer side effects is desired.

U.S. 2005/0277638 (patent document 1) and U.S. 2005/0137243 (patent document 2) disclose that a compound represented by the following formula

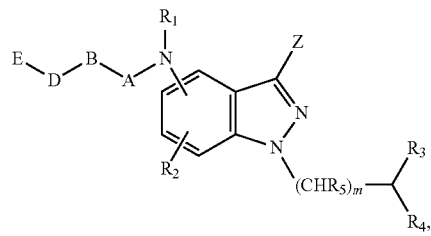

wherein A is selected from the group consisting of —C(O)—, —S(O)—, —S(O)$_2$—, —C(=NRa)— and —C(=S)—;
B is selected from the group consisting of alkylene, alkenyl, carbonylalkyl, cycloalkyl, —NRb— and —NRb-alkyl;
D is a bond or selected from the group consisting of alkylene, aryl, arylalkyl, heterocyclyl and heterocyclylalkyl;
E is selected from the group consisting of alkyl, alkyl-C(O)—, alkyl-C(O)—NH—, alkyl-NH—, alkyl-NH—C(O)—, alkyl-NH—S(O)$_2$—, alkoxy, alkyl-S—, alkyl-S(O)$_2$—, alkyl-S(O)$_2$—NH—, aryl, aryl-C(O)—, aryl-C(O)—NH—, aryl-C=N—O—, aryl-NH—, aryl-NH—C(O)—, aryl-NH—S(O)$_2$—, aryloxy, aryl-S—, aryl-S-alkyl-C(O)—, aryl-S(O)$_2$—, aryl-S(O)$_2$—NH—, arylalkyl-C(O)—, arylalkyl-C(O)—NH—, arylalkyl-NH—, arylalkyl-NH—C(O)—, arylalkyl-NH—S(O)$_2$—, arylalkoxy, arylalkyl-S—, arylalkyl-S(O)$_2$—, arylalkyl-S(O)$_2$—NH—, cycloalkyl, cycloalkyl-C(O)—, cycloalkyl-C(O)—NH—, cycloalkyl-NH—, cycloalkyl-NH—C(O)—, cycloalkyl-NH—S(O)$_2$—, cycloalkoxy, cycloalkyl-S—, cycloalkyl-S(O)$_2$—, cycloalkyl-S(O)$_2$—NH—, cycloalkenyl, cycloalkenylalkyl, cycloalkenyl-C(O)—, cycloalkenyl-C(O)—NH—, cycloalkenyl-NH—, cycloalkenyl-NH—C(O)—, cycloalkenyl-NH—S(O)$_2$—, cycloalkenyloxy, cycloalkenyl-S—, cycloalkenyl-S(O)$_2$—, cycloalkenyl-S(O)$_2$—NH—, heterocyclyl, heterocyclyl-C(O)—, heterocyclyl-C(O)—NH—, heterocyclyl-NH—, heterocyclyl-NH—C(O)—, heterocyclyl-NH—S(O)$_2$—, heterocyclyl-O—, heterocyclyl-S—, heterocyclyl-S(O)$_2$—, heterocyclyl-S(O)$_2$—NH—, heterocyclylalkyl-C(O)—, heterocyclylalkyl-C(O)—NH—, heterocyclylalkyl-NH—, heterocyclylalkyl-NH—C(O)—, heterocyclylalkyl-NH—S(O)$_2$—, heterocyclylalkyl-O—, heterocyclylalkyl-S—, heterocyclylalkyl-S(O)$_2$— and heterocyclylalkyl-S(O)$_2$—NH—;
$R_1$ is selected from the group consisting of hydrogen and alkyl;
$R_2$ is selected from the group consisting of hydrogen, halogen, alkyl and alkoxy;
$R_3$ is $R_c R_d R$—;
$R_4$ is selected from the group consisting of hydrogen and alkyl;
$R_4$ and $R_c$ are optionally bonded to each other to form a heterocycle;
$R_5$ are each independently selected from the group consisting of hydrogen and alkyl;
$R_a$ is selected from the group consisting of hydrogen and alkyl;
$R_b$ is selected from the group consisting of hydrogen and alkyl;
$R_b$ and $R_1$ are optionally bonded to each other to form a heterocycle;
$R_c$ and $R_d$ are each selected from the group consisting of hydrogen atom, alkyl, aryl, arylalkyl, cycloalkyl, cycloalkenylalkyl, heterocyclyl, heterocyclylalkyl and hydroxyalkyl, or $R_c$ and $R_d$ are optionally bonded to each other to form a heterocycle;

Z is selected from the group consisting of hydrogen, alkyl and halogen;
m is 1, 2 or 3, provided when B is —NR$_b$— or —NR$_b$-alkyl, then D is selected from the group consisting of alkylene, aryl, arylalkyl, heterocyclyl and heterocyclylalkyl,
and the like have prophylactic or treatment use for eating disorder, obesity, reproductive abnormality, mental diseases and the like, as melanin concentrating hormone antagonists.

In addition, WO 02/50091 (patent document 3) discloses that a compound represented by the following formula

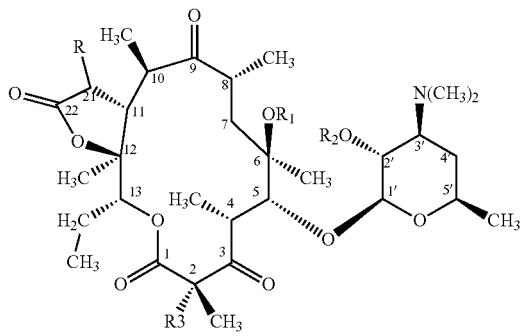

wherein R is hydrogen, cyano, (CH$_2$)nA-X—R$_4$ or (CH$_2$)nR$_5$;
A is —N(R$_6$)—, —N[C(O)R$_6$]—, —N(R$_6$)C(O)—, —N(R$_6$)S(O)$_2$—, —N(R$_6$)C(O)O—, —N═C(R$_6$)— or —N(R$_6$)C(Y)N(R$_7$)—;
R$_1$ is C$_{1-6}$ alkyl or C$_{3-6}$ alkenyl;
R$_2$ is hydrogen or a hydroxyl-protecting group;
R$_3$ is hydrogen or halogen;
X is a bond, a C$_{1-10}$ alkylene chain, a C$_{2-10}$ alkenylene chain or a C$_{2-10}$ alkynylene chain, wherein these chains are (i) optionally interrupted by a divalent group selected from —O—, —N(R$_8$)—, —C(O)—, —N(R$_8$)C(Y)N(R$_9$)—, —S(O)m-, —N(R$_8$)C(O)—, —C(O)N(R$_8$)—, —N(R$_8$)C(O)C(O)—, —C(O)O— and —C(NOR$_6$)—, and/or (ii) optionally substituted by C$_{1-4}$ alkyl, oxo, C$_{1-4}$ alkoxy, halogen, cyano, phenoxy, hydroxy, NR$_8$R$_9$, N(R$_8$)C(O)R$_9$, ═NOR$_6$, NR$_8$C(Y)NR$_9$ or optionally substituted phenyl;
R$_4$ is hydrogen,
optionally substituted phenyl,
optionally substituted C$_{3-7}$ cycloalkyl,
optionally substituted 9- or 10-membered fused bicyclic carbocyclyl,
optionally substituted 5- or 6-membered heteroaryl wherein the 5-membered heteroaryl contains at least one hetero atom from oxygen atom, sulfur atom and nitrogen atom, and the 6-membered heteroaryl contains 1 to 3 nitrogen atoms,
optionally substituted 5- or 6-membered heterocyclyl, or
R$_4$ is optionally substituted 9- or 10-membered fused bicyclic heterocyclyl containing at least one hetero atom from oxygen atom, sulfur atom and nitrogen atom;
R$_5$ is 5- or 6-membered heterocyclyl containing at least one nitrogen atom, which is optionally substituted by 1 or 2 substituents selected from oxo group and 9- or 10-membered fused bicyclic heterocyclyl containing at least one hetero atom selected from or oxygen atom, sulfur atom and nitrogen atom;
R$_6$ and R$_7$ are each independently a hydrogen atom, C$_{1-4}$ alkyl, or phenyl optionally substituted by 1 or 2 C$_{1-4}$ alkyl;
R$_8$ and R$_9$ are each independently hydrogen, phenyl (optionally substituted by 1 or 2 C$_{1-4}$ alkyl), or R$_8$ and R$_9$ are each independently C$_{1-4}$ alkyl optionally substituted by 1 or 2 substituents selected from phenyl, C$_{1-4}$ alkoxy, cyano, 5-membered heteroaryl containing 1 or 2 hetero atoms selected from oxygen atom, sulfur atom and nitrogen atom, 6-membered heteroaryl containing 1 to 3 nitrogen atoms, hydroxy, oxo and carboxy;
Y is an oxygen atom or a sulfur atom;
n is an integer of 0 or 1 to 3; and
m is 0, 1 or 2,
and the like is applicable to prophylactic or therapeutic use for systemic or topical bacterial infection and the like.

DOCUMENT LIST

Patent Document

Patent Document 1: U.S. 2005/0277638
Patent Document 2: U.S. 2005/0137243
Patent Document 3: WO 02/50091

Non-Patent Document

Non-Patent Document 1: Diabetes (2006)55, 1813-1818
Non-Patent Document 2: Mechanisms of Ageing and Development (2003)124, 495-502

SUMMARY OF THE INVENTION

Problems to be Solved by the Invention

An object of the present invention is to provide a compound useful for the prophylaxis or treatment of diseases associated with the differentiation regulation of muscle cell or adipocyte, such as diabetes, obesity, dyslipidemia and the like, and superior in pharmacological action, physicochemical properties and the like.

Means of Solving the Problems

The present inventors have found for the first time that a compound represented by the formula (I):

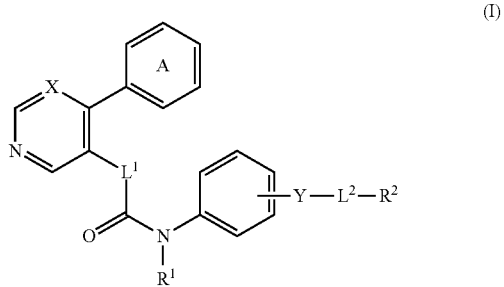

wherein
A is an optionally substituted benzene ring,
X is CH or N,
Y is a bond, —O— or —S—,
L$^1$ is a C$_{1-6}$ alkylene group, a C$_{2-6}$ alkenylene group or a C$_{2-6}$ alkynylene group,
L$^2$ is a C$_{1-6}$ alkylene group, a C$_{2-6}$ alkenylene group or a C$_{2-6}$ alkynylene group,
R$^1$ is a hydrogen atom or a C$_{1-6}$ alkyl group,
R$^2$ is (1) a 5- or 6-membered heterocyclic group optionally substituted by 1 to 3 substituents selected from a halogen atom, a C$_{1-6}$ alkyl group and a C$_{1-6}$ alkoxy group, (2) a fused heterocyclic group of a benzene ring and a 5- or 6-membered heterocycle, wherein the fused heterocyclic group is optionally substituted by 1 to 3 substituents selected from a halogen atom, a $C_{1-6}$ alkyl group and a $C_{1-6}$ alkoxy group, (3) —PO(OR³)₂ or (4) —S(O)$_m$R⁴,
R³ is a $C_{1-6}$ alkyl group,
R⁴ is a $C_{1-6}$ alkyl group, and
m is 0, 1 or 2,
or a salt thereof [hereinafter sometimes to be referred to as compound (I)] has a muscle cell or adipocyte differentiation regulating action, shows various pharmacological actions based on promotion of myoblast differentiation, suppression of adipocyte differentiation, or/and inhibition of NF-kB activation, and is useful for the prophylaxis or treatment of diseases associated with the differentiation regulation of muscle cell or adipocyte, such as diabetes, obesity, dyslipidemia and the like. The present inventors have conducted intensive studies based on these findings and completed the present invention.

Accordingly, the present invention relates to (1) compound (I);
(2) the compound or salt of the above-mentioned (1), wherein L¹ is a $C_{2-6}$ alkenylene group;
(3) the compound or salt of the above-mentioned (1) or (2), wherein L² is a $C_{1-6}$ alkylene group;
(4) the compound or salt of the above-mentioned (1), (2) or (3), wherein A is a benzene ring optionally substituted by 1 to 3 substituents selected from a $C_{1-6}$ alkoxy group and a halogen atom;
(5) the compound or salt of the above-mentioned (1), (2), (3) or (4), wherein Y is a bond or —O—;
(6) the compound or salt of the above-mentioned (1), (2), (3), (4) or (5), wherein R² is
(1) imidazolyl, oxadiazolyl or morpholinyl, each of which is optionally substituted by 1 to 3 $C_{1-6}$ alkyl groups,
(2) benzimidazolyl optionally substituted by 1 to 3 $C_{1-6}$ alkyl groups,
(3) —PO(OCH₃)₂ or —PO(OC₂H₅)₂ or
(4) —S(O)₂CH₃;
(6A) the compound or salt of the above-mentioned (1), (2), (3), (4), (5) or (6), wherein R² is imidazolyl, benzimidazolyl, oxadiazolyl or morpholinyl, each of which is optionally substituted by 1 to 3 $C_{1-6}$ alkyl groups;
(7) the compound or salt of the above-mentioned (1), (2), (3), (4), (5) or (6), wherein R² is imidazol-1-yl, benzimidazol-1-yl, 1,3,4-oxadiazol-2-yl or morpholin-4-yl, each of which is optionally substituted by $C_{1-6}$ alkyl group(s);
(7A) the compound or salt of the above-mentioned (1), (2), (3), (4), (5) or (6), wherein R² is —PO(OCH₃)₂, —PO(OC₂H₅)₂ or —S(O)₂CH₃;
(7B) the compound or salt of the above-mentioned (1), (2), (3), (4), (5) or (6), wherein R² is imidazol-1-yl, benzimidazol-1-yl, 1,3,4-oxadiazol-2-yl or morpholin-4-yl, each of which is optionally substituted by 1 to 3 $C_{1-6}$ alkyl groups;
(8) the compound or salt of the above-mentioned (1), which is represented by the formula (II):

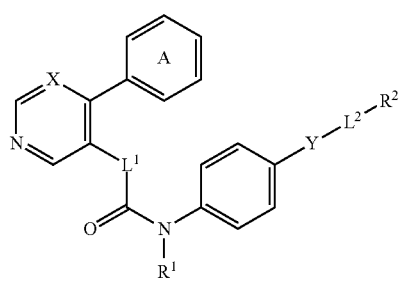

(II)

wherein each symbol is as defined in the above-mentioned (1), (2), (3), (4), (5), (6), (6A), (7), (7A) or (7B);

(9) the compound or salt of the above-mentioned (1), (2), (3), (4), (5) or (6), which is represented by the formula (II):

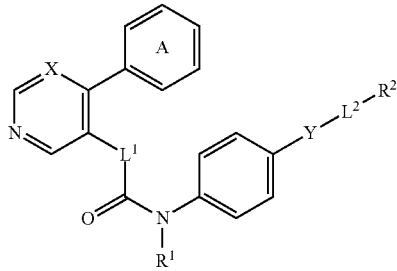

(II)

wherein
A is a benzene ring optionally substituted by 1 to 3 substituents selected from a $C_{1-6}$ alkoxy group and a halogen atom,
X is CH or N,
Y is a bond or —O—,
L¹ is a $C_{2-6}$ alkenylene group,
L² is a $C_{1-6}$ alkylene group,
R¹ is a hydrogen atom, and
R² is
(1) imidazol-1-yl, 1,3,4-oxadiazol-2-yl or morpholin-4-yl, each of which is optionally substituted by 1 to 3 $C_{1-6}$ alkyl groups,
(2) benzimidazol-1-yl optionally substituted by 1 to 3 $C_{1-6}$ alkyl groups,
(3) —PO(OCH₃)₂ or —PO(OC₂H₅)₂, or
(4) —S(O)₂CH₃;
(10) (2E)-3-[4-(4-fluorophenyl)pyridin-3-yl]-N-{4-[2-(1,3,4-oxadiazol-2-yl)ethyl]phenyl}prop-2-enamide or a salt thereof;
(11) (2E)-3-[4-(4-fluorophenyl)pyrimidin-5-yl]-N-{4-[2-(1,3,4-oxadiazol-2-yl)ethyl]phenyl}prop-2-enamide or a salt thereof;
(11A) a prodrug of the compound or salt of the above-mentioned (1), (2), (3), (4), (5), (6), (6A), (7), (7A), (7B), (8), (9), (10) or (11);
(12) a medicament comprising the compound or salt of the above-mentioned (1), (2), (3), (4), (5), (6), (6A), (7), (7A), (7B), (8), (9), (10), (11) or (11A) or a prodrug thereof;
(13) the medicament of the above-mentioned (12), which is a muscle cell or adipocyte differentiation regulating agent;
(14) the medicament of the above-mentioned (12), which is an agent for the prophylaxis or treatment of a muscle cell or adipocyte differentiation-associated disease;
(15) the medicament of the above-mentioned (12), which is an agent for the prophylaxis or treatment of diabetes, obesity or dyslipidemia;
(16) a method for the prophylaxis or treatment of diabetes, obesity or dyslipidemia in a mammal, comprising administering an effective amount of the compound or salt of the above-mentioned (1), (2), (3), (4), (5), (6), (6A), (7), (7A), (7B), (8), (9), (10) or (11) or a prodrug thereof to the mammal;
(17) use of the compound or salt of the above-mentioned (1), (2), (3), (4), (5), (6), (6A), (7), (7A), (7B), (8), (9), (10) or (11) or a prodrug thereof for the production of an agent for the prophylaxis or treatment of diabetes, obesity or dyslipidemia;
(18) the compound or salt of the above-mentioned (1), (2), (3), (4), (5), (6), (6A), (7), (7A), (7B), (8), (9), (10) or (11)

or a prodrug thereof for use in the prophylaxis or treatment of diabetes, obesity or dyslipidemia;
and the like.

Effect of the Invention

Compound (I) has a muscle cell or/and adipocyte differentiation regulating action, is useful for the prophylaxis or treatment of diabetes, obesity or dyslipidemia and the like, and has superior efficacy.

DETAILED DESCRIPTION OF THE INVENTION

The definition of each symbol in the formula (I) is explained in detail in the following.

Unless otherwise specified, the "halogen atom" in the present specification means a fluorine atom, a chlorine atom, a bromine atom or an iodine atom.

Unless otherwise specified, the "$C_{1-6}$ alkyl group" in the present specification means methyl, ethyl, propyl, isopropyl, butyl, isobutyl, sec-butyl, tert-butyl, pentyl, isopentyl, neopentyl, 1-ethylpropyl, hexyl, isohexyl, 1,1-dimethylbutyl, 2,2-dimethylbutyl, 3,3-dimethylbutyl, 2-ethylbutyl or the like.

Unless otherwise specified, the "$C_{1-6}$ alkoxy group" in the present specification means methoxy, ethoxy, propoxy, isopropoxy, butoxy, isobutoxy, sec-butoxy, tert-butoxy or the like.

Unless otherwise specified, the "$C_{1-6}$ alkoxy-carbonyl group" in the present specification means methoxycarbonyl, ethoxycarbonyl, propoxycarbonyl, isopropoxycarbonyl, tert-butoxycarbonyl or the like.

Unless otherwise specified, the "$C_{1-6}$ alkylene group" in the present specification, means methylene (—$CH_2$—); ethylene (—$(CH_2)_2$—);
—$(CH_2)_3$—, —$CH(CH_3)CH_2$—, —$CH_2CH(CH_3)$—;
—$(CH_2)_4$—, —$CH(CH_3)(CH_2)_2$—, —$(CH_2)_2CH(CH_3)$—, —$C(CH_3)_2CH_2$—, —$CH_2C(CH_3)_2$—;
—$(CH_2)_5$—, —$CH(CH_3)(CH_2)_3$—, —$(CH_2)_3CH(CH_3)$—, —$CH(C_2H_5)(CH_2)_2$—, —$(CH_2)_2CH(C_2H_5)$—, —$CH_2CH(CH_3)(CH_2)_2$—, —$(CH_2)_2CH(CH_3)CH_2$—, —$CH_2CH(C_2H_5)CH_2$—, —$C(CH_3)_2(CH_2)_2$—, —$(CH_2)_2C(CH_3)_2$—, —$CH_2C(CH_3)_2CH_2$—;
—$(CH_2)_6$—, —$CH(CH_3)(CH_2)_4$—, —$(CH_2)_4CH(CH_3)$—, —$CH(C_2H_5)(CH_2)_3$—, —$CH_2CH(CH_3)(CH_2)_3$—, —$(CH_2)_3CH(CH_3)CH_2$—, —$(CH_2)_2CH(CH_3)(CH_2)_2$—, —$(CH_2)_3CH(C_2H_5)$—, —$C(CH_3)_2(CH_2)_3$—, —$(CH_2)_3C(CH_3)_2$—, —$CH_2C(CH_3)_2(CH_2)_2$—, —$(CH_2)_2C(CH_3)_2CH_2$—, —$C(CH_3)_2C(CH_3)_2$—;
or the like.

Unless otherwise specified, the "$C_{2-6}$ alkenylene group" in the present specification means
—CH=CH—;
—CH=CH—$CH_2$—, —$CH_2$—CH=CH—;
—CH=CH—$CH_2$—$CH_2$—, —$CH_2$—CH=CH—$CH_2$—, —$CH_2$—$CH_2$—CH=CH—, —CH=CH—CH=CH—, —$C(CH_3)$=CH—$CH_2$—, —CH=$C(CH_3)$—$CH_2$—, —CH=CH—$CH(CH_3)$—, —$CH(CH_3)$—CH=CH—, —$CH_2$—$C(CH_3)$=CH—, —$CH_2$—CH=$C(CH_3)$—;
—CH=CH—$CH_2$—$CH_2$—$CH_2$—, —$CH_2$—CH=CH—$CH_2$—$CH_2$—, —$CH_2$—$CH_2$—CH=CH—$CH_2$—, —$CH_2$—$CH_2$—$CH_2$—CH=CH—;
—CH=CH—$CH_2$—$CH_2$—$CH_2$—$CH_2$—, —$CH_2$—CH=CH—$CH_2$—$CH_2$—$CH_2$—, —$CH_2$—$CH_2$—CH=CH—$CH_2$—$CH_2$—, —$CH_2$—$CH_2$—$CH_2$—CH=CH—$CH_2$—, —$CH_2$—$CH_2$—$CH_2$—$CH_2$—CH=CH—;
or the like.

Unless otherwise specified, the "$C_{2-6}$ alkynylene group" in the present specification means
—C≡C—;
—C≡C—$CH_2$—, —$CH_2$—C≡C—;
—C≡C—$CH_2$—$CH_2$—, —$CH_2$—C≡C—$CH_2$—, —$CH_2$—$CH_2$—C≡C—;
—C≡C—$CH_2$—$CH_2$—$CH_2$—, —$CH_2$—C≡C—$CH_2$—$CH_2$—, —$CH_2$—$CH_2$—C≡C—$CH_2$—, —$CH_2$—$CH_2$—$CH_2$—C≡C—;
—C≡C—$CH_2$—$CH_2$—$CH_2$—$CH_2$—, —$CH_2$—C≡C—$CH_2$—$CH_2$—$CH_2$—, —$CH_2$—$CH_2$—C≡C—$CH_2$—$CH_2$—, —$CH_2$—$CH_2$—$CH_2$—C≡C—$CH_2$—, —$CH_2$—$CH_2$—$CH_2$—$CH_2$—C≡C—;
or the like.

Unless otherwise specified, the "$C_{1-6}$ alkyl-carbonyl group" in the present specification means acetyl, propanoyl, butanoyl, 2-methylpropanoyl, pentaoyl, 2-methylbutanoyl, pivaloyl, hexanoyl or the like.

Ring A is an optionally substituted benzene ring.

The "benzene ring" of the "optionally substituted benzene ring" for ring A optionally has 1 to 3 substituents at substitutable positions.

Examples of the substituent include
(1) a $C_{3-10}$ cycloalkyl group (e.g., cyclopropyl, cyclohexyl);
(2) a $C_{6-14}$ aryl group (e.g., phenyl, naphthyl) optionally substituted by 1 to 3 substituents selected from
   (a) a $C_{1-6}$ alkyl group optionally substituted by 1 to 3 halogen atoms,
   (b) a hydroxy group,
   (c) a $C_{1-6}$ alkoxy group optionally substituted by 1 to 3 halogen atoms, and
   (d) a halogen atom;
(3) a 4- to 7-membered aromatic heterocyclic group (e.g., thienyl, furyl, pyridyl, pyrazolyl, imidazolyl, tetrazolyl, oxazolyl, thiazolyl, oxadiazolyl, thiadiazolyl) optionally substituted by 1 to 3 substituents selected from
   (a) a $C_{1-6}$ alkyl group optionally substituted by 1 to 3 halogen atoms,
   (b) a hydroxy group,
   (c) a $C_{1-6}$ alkoxy group optionally substituted by 1 to 3 halogen atoms, and
   (d) a halogen atom;
(4) a 4- to 7-membered non-aromatic heterocyclic group (e.g., tetrahydrofuryl, morpholinyl, thiomorpholinyl, piperidyl, pyrrolidinyl, piperazinyl) optionally substituted by 1 to 3 substituents selected from
   (a) a $C_{1-6}$ alkyl group optionally substituted by 1 to 3 halogen atoms,
   (b) a hydroxy group,
   (c) a $C_{1-6}$ alkoxy group optionally substituted by 1 to 3 halogen atoms,
   (d) a halogen atom, and
   (e) an oxo group;
(5) an amino group optionally mono- or di-substituted by substituent(s) selected from
   (a) a $C_{1-6}$ alkyl group optionally substituted by 1 to 3 halogen atoms,
   (b) a $C_{1-6}$ alkyl-carbonyl group optionally substituted by 1 to 3 halogen atoms,
   (c) a $C_{1-6}$ alkoxy-carbonyl group optionally substituted by 1 to 3 halogen atoms,
   (d) a $C_{1-6}$ alkylsulfonyl (e.g., methylsulfonyl) group optionally substituted by 1 to 3 halogen atoms,
   (e) a carbamoyl group optionally mono- or di-substituted by $C_{1-6}$ alkyl group(s) optionally substituted by 1 to 3 halogen atoms, and (f) a 4- to 7-membered aromatic heterocyclic group (e.g., thienyl, furyl, pyridyl, pyrazolyl, imidazolyl, tetrazolyl, oxazolyl, thiazolyl, oxadiazolyl, thiadiazolyl);

(6) a $C_{1-6}$ alkyl-carbonyl group optionally substituted by 1 to 3 halogen atoms;

(7) a $C_{1-6}$ alkoxy-carbonyl group (e.g., methoxycarbonyl) optionally substituted by 1 to 3 substituents selected from
(a) a halogen atom,
(b) a $C_{1-6}$ alkoxy group,
(c) a $C_{6-14}$ aryl group (e.g., phenyl), and
(d) a 4- to 7-membered heterocyclic group (e.g., tetrahydrofuryl);

(8) a $C_{1-6}$ alkylsulfonyl group (e.g., methylsulfonyl, ethylsulfonyl, isopropylsulfonyl) optionally substituted by 1 to 3 halogen atoms;

(9) a carbamoyl group optionally mono- or di-substituted by $C_{1-6}$ alkyl group(s) optionally substituted by 1 to 3 halogen atoms;

(10) a thiocarbamoyl group optionally mono- or di-substituted by $C_{1-6}$ alkyl group(s) optionally substituted by 1 to 3 halogen atoms;

(11) a sulfamoyl group optionally mono- or di-substituted by $C_{1-6}$ alkyl group(s) optionally substituted by 1 to 3 halogen atoms;

(12) a carboxy group;

(13) a hydroxy group;

(14) a $C_{1-6}$ alkoxy group optionally substituted by 1 to 3 substituents selected from
(a) a halogen atom,
(b) a carboxy group,
(c) a $C_{1-6}$ alkoxy group,
(d) a $C_{1-6}$ alkoxy-carbonyl group optionally substituted by 1 to 3 $C_{6-14}$ aryl groups (e.g., phenyl),
(e) an amino group optionally mono- or di-substituted by substituent(s) selected from a $C_{1-6}$ alkyl group and a $C_{1-6}$ alkoxy-carbonyl group,
(f) a 4- to 7-membered heterocyclic group (e.g., tetrahydrofuryl), and
(g) a $C_{3-10}$ cycloalkyl group;

(15) a $C_{2-6}$ alkenyloxy group (e.g., ethenyloxy) optionally substituted by 1 to 3 halogen atoms;

(16) a $C_{7-13}$ aralkyloxy group (e.g., benzyloxy);

(17) a $C_{6-14}$ aryloxy group (e.g., phenyloxy, naphthyloxy);

(18) a $C_{1-6}$ alkyl-carbonyloxy group (e.g., acetyloxy, tert-butylcarbonyloxy);

(19) a $C_{6-14}$ aryl-carbonyl group (e.g., benzoyl) optionally substituted by 1 to 3 substituents selected from
(a) a halogen atom, and
(b) a $C_{1-6}$ alkyl group optionally substituted by 1 to 3 halogen atoms;

(20) a 4- to 7-membered non-aromatic heterocyclylcarbonyl group (e.g., pyrrolidinylcarbonyl, morpholinylcarbonyl) optionally substituted by 1 to 3 substituents selected from a $C_{1-6}$ alkyl group optionally substituted by 1 to 3 halogen atoms;

(21) a mercapto group;

(22) a $C_{1-6}$ alkylthio group (e.g., methylthio, ethylthio) optionally substituted by 1 to 3 substituents selected from
(a) a halogen atom, and
(b) a $C_{1-6}$ alkoxy-carbonyl group;

(23) a $C_{7-13}$ aralkylthio group (e.g., benzylthio);

(24) a $C_{6-14}$ arylthio group (e.g., phenylthio, naphthylthio);

(25) a cyano group;

(26) a nitro group;

(27) a halogen atom (e.g., a fluorine atom, a chlorine atom, a bromine atom);

(28) a $C_{1-3}$ alkylenedioxy group;

(29) a $C_{1-3}$ alkyleneoxy group (e.g., methyleneoxy, ethyleneoxy);

(30) a 4- to 7-membered aromatic heterocyclylcarbonyl group (e.g., pyrazolylcarbonyl, pyrazinylcarbonyl, isoxazolylcarbonyl, pyridylcarbonyl, thiazolylcarbonyl) optionally substituted by 1 to 3 substituents selected from a $C_{1-6}$ alkyl group optionally substituted by 1 to 3 halogen atoms;

(31) a $C_{3-10}$ cycloalkoxy group (e.g., cyclopropoxy, cyclopentyloxy) optionally substituted by 1 to 3 substituents selected from
(a) a halogen atom (e.g., a fluorine atom), and
(b) a $C_{1-6}$ alkoxy group (e.g., methoxy);

(32) a $C_{1-6}$ alkyl group optionally substituted by 1 to 3 substituents selected from
(a) a halogen atom,
(b) a carboxy group,
(c) a hydroxy group,
(d) a $C_{1-6}$ alkoxy-carbonyl group,
(e) a $C_{1-6}$ alkoxy group, and
(f) an amino group optionally mono- or di-substituted by $C_{1-6}$ alkyl group(s);

(33) a $C_{2-6}$ alkenyl group (e.g., ethenyl, 1-propenyl) optionally substituted by 1 to 3 substituents selected from
(a) a halogen atom,
(b) a carboxy group,
(c) a hydroxy group,
(d) a $C_{1-6}$ alkoxy-carbonyl group,
(e) a $C_{1-6}$ alkoxy group, and
(f) an amino group optionally mono- or di-substituted by $C_{1-6}$ alkyl group(s);

(34) a $C_{7-12}$ aralkyl group (e.g., benzyl) optionally substituted by 1 to 3 substituents selected from
(a) a $C_{1-6}$ alkyl group optionally substituted by 1 to 3 halogen atoms,
(b) a hydroxy group,
(c) a $C_{1-6}$ alkoxy group, and
(d) a halogen atom;

and the like. When the substituents are two or more, the respective substituents may be the same or different.

A is preferably a benzene ring optionally substituted by 1 to 3 substituents selected from
(1) a $C_{1-6}$ alkoxy group (e.g., methoxy);
(2) a halogen atom (e.g., a fluorine atom, a chlorine atom, a bromine atom);
and the like.

A is more preferably a benzene ring optionally substituted by 1 to 3 halogen atoms (e.g., a fluorine atom).

X is CH or N.

Y is a bond, —O— or —S—.

Y is preferably a bond or —O—.

Y is more preferably a bond.

$L^1$ is a $C_{1-6}$ alkylene group, a $C_{2-6}$ alkenylene group or a $C_{2-6}$ alkynylene group.

$L^1$ is preferably a $C_{2-6}$ alkenylene group.

$L^1$ is more preferably —CH=CH—.

$L^2$ is a $C_{1-6}$ alkylene group, a $C_{2-6}$ alkenylene group or a $C_{2-6}$ alkynylene group.

$L^2$ is preferably a $C_{1-6}$ alkylene group.

$L^2$ is more preferably methylene or ethylene.

$L^2$ is still more preferably ethylene.

$R^1$ is a hydrogen atom or a $C_{1-6}$ alkyl group.

$R^1$ is preferably a hydrogen atom.

$R^2$ is (1) a 5- or 6-membered heterocyclic group optionally substituted by 1 to 3 substituents selected from a halogen atom, a $C_{1-6}$ alkyl group and a $C_{1-6}$ alkoxy group, (2) a fused heterocyclic group of a benzene ring and a 5- or 6-membered heterocyclic group, wherein the fused heterocyclic group is optionally substituted by 1 to 3 substituents selected from a halogen atom, a $C_{1-6}$ alkyl group and a $C_{1-6}$ alkoxy group, (3) —PO(OR$^3$)$_2$ or (4) —S(O)$_m$R$^4$.

Examples of the "5- or 6-membered heterocyclic group" of the "5- or 6-membered heterocyclic group optionally substituted by 1 to 3 substituents selected from a halogen atom, a $C_{1-6}$ alkyl group and a $C_{1-6}$ alkoxy group" for R$^2$ include a 5- or 6-membered aromatic heterocyclic group, a 5- or 6-membered non-aromatic heterocyclic group and the like.

Examples of the 5- or 6-membered aromatic heterocyclic group include a 5- or 6-membered aromatic heterocyclic group containing, as a ring-constituting atom besides carbon atom, 1 to 4 hetero atoms selected from an oxygen atom, a sulfur atom and a nitrogen atom.

Preferable examples of the 5- or 6-membered aromatic heterocyclic group include monocyclic aromatic heterocyclic groups such as furyl (e.g., 2-furyl, 3-furyl), thienyl (e.g., 2-thienyl, 3-thienyl), pyridyl (e.g., 2-pyridyl, 3-pyridyl, 4-pyridyl), pyrimidinyl (e.g., 2-pyrimidinyl, 4-pyrimidinyl, 5-pyrimidinyl), pyridazinyl (e.g., 3-pyridazinyl, 4-pyridazinyl), pyrazinyl (e.g., 2-pyrazinyl), pyrrolyl (e.g., 1-pyrrolyl, 2-pyrrolyl, 3-pyrrolyl), imidazolyl (e.g., imidazol-1-yl, imidazol-2-yl, imidazol-4-yl, imidazol-5-yl), pyrazolyl (e.g., 1-pyrazolyl, 3-pyrazolyl, 4-pyrazolyl), thiazolyl (e.g., 2-thiazolyl, 4-thiazolyl, 5-thiazolyl), isothiazolyl (e.g., 3-isothiazolyl, 4-isothiazolyl, 5-isothiazolyl), oxazolyl (e.g., 2-oxazolyl, 4-oxazolyl, 5-oxazolyl), isoxazolyl (e.g., 3-isoxazolyl, 4-isoxazolyl, 5-isoxazolyl), oxadiazolyl (e.g., 1,3,4-oxadiazol-2-yl, 1,2,4-oxadiazol-3-yl, 1,2,4-oxadiazol-5-yl), thiadiazolyl (e.g., 1,3,4-thiadiazol-2-yl), triazolyl (e.g., 1,2,4-triazol-1-yl, 1,2,4-triazol-3-yl, 1,2,3-triazol-1-yl, 1,2,3-triazol-2-yl, 1,2,3-triazol-4-yl), tetrazolyl (e.g., tetrazol-1-yl, tetrazol-5-yl), triazinyl (e.g., 1,2,4-triazin-1-yl, 1,2,4-triazin-3-yl) and the like, and the like.

Examples of the 5- or 6-membered non-aromatic heterocyclic group include a 5- or 6-membered non-aromatic heterocyclic group containing, as a ring constituting atom m besides carbon atom, 1 to 4 hetero atoms selected from an oxygen atom, a sulfur atom and a nitrogen atom.

Preferable examples of the 5- or 6-membered non-aromatic heterocyclic group include monocyclic non-aromatic heterocyclic groups such as pyrrolidinyl (e.g., 1-pyrrolidinyl, 2-pyrrolidinyl), piperidyl (e.g., piperidino, 2-piperidyl, 3-piperidyl, 4-piperidyl), morpholinyl (e.g., morpholin-4-yl), thiomorpholinyl (e.g., thiomorpholin-4-yl), piperazinyl (e.g., 1-piperazinyl, 2-piperazinyl, 3-piperazinyl), hexamethyleniminyl (e.g., hexamethylenimin-1-yl), oxazolidinyl (e.g., oxazolidin-2-yl), thiazolidinyl (e.g., thiazolidin-2-yl), imidazolidinyl (e.g., imidazolidin-2-yl, imidazolidin-3-yl), oxazolinyl (e.g., oxazolin-2-yl), thiazolinyl (e.g., thiazolin-2-yl), imidazolinyl (e.g., imidazolin-2-yl, imidazolin-3-yl), dioxolyl (e.g., 1,3-dioxol-4-yl), dioxolanyl (e.g., 1,3-dioxolan-4-yl), dihydrooxadiazolyl (e.g., 4,5-dihydro-1,2,4-oxadiazol-3-yl), pyranyl (e.g., 4-pyranyl), tetrahydropyranyl (e.g., 2-tetrahydropyranyl, 3-tetrahydropyranyl, 4-tetrahydropyranyl), thiopyranyl (e.g., 4-thiopyranyl), tetrahydrothiopyranyl (e.g., 2-tetrahydrothiopyranyl, 3-tetrahydrothiopyranyl, 4-tetrahydrothiopyranyl), tetrahydrofuryl (e.g., tetrahydrofuran-3-yl, tetrahydrofuran-2-yl), pyrazolidinyl (e.g., pyrazolidin-1-yl, pyrazolidin-3-yl), pyrazolinyl (e.g., pyrazolin-1-yl), tetrahydropyrimidinyl (e.g., tetrahydropyrimidin-1-yl), dihydrotriazolyl (e.g., 2,3-dihydro-1H-1,2,3-triazol-1-yl), tetrahydrotriazolyl (e.g., 2,3,4,5-tetrahydro-1H-1,2,3-triazol-1-yl) and the like, and the like.

The "5- or 6-membered heterocyclic group" of the "5- or 6-membered heterocyclic group optionally substituted by 1 to 3 substituents selected from a halogen atom, a $C_{1-6}$ alkyl group and a $C_{1-6}$ alkoxy group" for R$^2$ is preferably imidazolyl, oxadiazolyl or morpholinyl (preferably oxadiazolyl or morpholinyl, more preferably oxadiazolyl), more preferably imidazol-1-yl, 1,3,4-oxadiazol-2-yl or morpholin-4-yl (preferably 1,3,4-oxadiazol-2-yl or morpholin-4-yl, more preferably 1,3,4-oxadiazol-2-yl).

The "5- or 6-membered heterocyclic group optionally substituted by 1 to 3 substituents selected from a halogen atom, a $C_{1-6}$ alkyl group and a $C_{1-6}$ alkoxy group" for R$^2$ is preferably imidazolyl, oxadiazolyl or morpholinyl (preferably oxadiazolyl or morpholinyl, more preferably oxadiazolyl), each of which is optionally substituted by 1 to 3 $C_{1-6}$ alkyl groups (e.g., methyl), more preferably imidazol-1-yl, 1,3,4-oxadiazol-2-yl or morpholin-4-yl (preferably 1,3,4-oxadiazol-2-yl or morpholin-4-yl, more preferably 1,3,4-oxadiazol-2-yl), each of which is optionally substituted by 1 to 3 $C_{1-6}$ alkyl groups (e.g., methyl).

Examples of the "fused heterocyclic group" of the "fused heterocyclic group of a benzene ring and a 5- or 6-membered heterocycle, wherein the fused heterocyclic group is optionally substituted by 1 to 3 substituents selected from a halogen atom, a $C_{1-6}$ alkyl group and a $C_{1-6}$ alkoxy group" for R$^2$ include fused heterocyclic groups such as quinolyl (e.g., 2-quinolyl, 3-quinolyl, 4-quinolyl, 6-quinolyl), isoquinolyl (e.g., 3-isoquinolyl), quinazolyl (e.g., 2-quinazolyl, 4-quinazolyl), quinoxalyl (e.g., 2-quinoxalyl, 6-quinoxalyl), benzofuranyl (e.g., 2-benzofuranyl, 3-benzofuranyl), benzothienyl (e.g., 2-benzothienyl, 3-benzothienyl), benzoxazolyl (e.g., 2-benzoxazolyl), benzisoxazolyl (e.g., 7-benzisoxazolyl), benzothiazolyl (e.g., 2-benzothiazolyl), benzimidazolyl (e.g., benzimidazol-1-yl, benzimidazol-2-yl, benzimidazol-5-yl), benzotriazolyl (e.g., 1H-1,2,3-benzotriazol-5-yl), indolyl (e.g., indol-1-yl, indol-2-yl, indol-3-yl, indol-5-yl), indazolyl (e.g., 1H-indazol-3-yl), dihydrobenzofuranyl (e.g., 2,3-dihydro-1-benzofuran-5-yl), dihydrobenzodioxinyl (e.g., 2,3-dihydro-1,4-benzodioxinyl), dihydrobenzodioxepinyl (e.g., 3,4-dihydro-2H-1,5-benzodioxepinyl), tetrahydrobenzofuranyl (e.g., 4,5,6,7-tetrahydro-1-benzofuran-3-yl), chromenyl (e.g., 4H-chromen-2-yl, 2H-chromen-3-yl), dihydrochromenyl (e.g., 3,4-dihydro-2H-chromen-2-yl), dihydroquinolyl (e.g., 1,2-dihydroquinolin-4-yl), tetrahydroquinolyl (e.g., 1,2,3,4-tetrahydroquinolin-4-yl), dihydroisoquinolyl (e.g., 1,2-dihydroisoquinolin-4-yl), tetrahydroisoquinolyl (e.g., 1,2,3,4-tetrahydroisoquinolin-4-yl) and the like.

The "fused heterocyclic group" of the "fused heterocyclic group of a benzene ring and a 5- or 6-membered heterocycle, wherein the fused heterocyclic group is optionally substituted by 1 to 3 substituents selected from a halogen atom, a $C_{1-6}$ alkyl group and a $C_{1-6}$ alkoxy group" for R$^2$ is preferably benzimidazolyl, more preferably benzimidazol-1-yl.

The "fused heterocyclic group" of the "fused heterocyclic group of a benzene ring and a 5- or 6-membered heterocycle, wherein the fused heterocyclic group is optionally substituted by 1 to 3 substituents selected from a halogen atom, a $C_{1-6}$ alkyl group and a $C_{1-6}$ alkoxy group" for R$^2$ is preferably benzimidazolyl optionally substituted by 1 to 3 $C_{1-6}$ alkyl groups (e.g., methyl), more preferably benzimidazol-1-yl optionally substituted by 1 to 3 $C_{1-6}$ alkyl groups (e.g., methyl).

R$^3$ of "—PO(OR$^3$)$_2$" for R$^2$ are the same or different and each is a $C_{1-6}$ alkyl group.

R$^3$ is preferably methyl or ethyl.

R$^4$ of "—S(O)$_m$R$^4$" for R$^2$ is a $C_{1-6}$ alkyl group.

R$^4$ is preferably methyl.

m of "—S(O)$_m$R$^4$" for R$^2$ is 0, 1 or 2.

m is preferably 2.

R$^2$ is preferably (1) imidazolyl, oxadiazolyl or morpholinyl, each of which is optionally substituted by 1 to 3 $C_{1-6}$ alkyl groups (e.g., methyl);

(2) benzimidazolyl optionally substituted by 1 to 3 $C_{1-6}$ alkyl groups (e.g., methyl);
(3) —PO(OCH$_3$)$_2$ or —PO(OC$_2$H$_5$)$_2$;
(4) —S(O)$_2$CH$_3$;
or the like.

$R^2$ is more preferably
(1) imidazol-1-yl, 1,3,4-oxadiazol-2-yl or morpholin-4-yl, each of which is optionally substituted by 1 to 3 $C_{1-6}$ alkyl groups (e.g., methyl);
(2) benzimidazol-1-yl optionally substituted by 1 to 3 $C_{1-6}$ alkyl groups (e.g., methyl);
(3) —PO(OCH$_3$)$_2$ or —PO(OC$_2$H$_5$)$_2$;
(4) —S(O)$_2$CH$_3$;
or the like.

$R^2$ is more preferably imidazol-1-yl, benzimidazol-1-yl, 1,3,4-oxadiazol-2-yl or morpholin-4-yl, each of which is optionally substituted by $C_{1-6}$ alkyl group(s) (e.g., methyl).

$R^2$ is further more preferably imidazol-1-yl, benzimidazol-1-yl, 1,3,4-oxadiazol-2-yl or morpholin-4-yl, each of which is optionally substituted by 1 to 3 $C_{1-6}$ alkyl groups (e.g., methyl).

$R^2$ is still more preferably 1,3,4-oxadiazol-2-yl or morpholin-4-yl, each of which is optionally substituted by 1 to 3 $C_{1-6}$ alkyl groups (e.g., methyl).

$R^2$ is particularly preferably 1,3,4-oxadiazol-2-yl optionally substituted by 1 to 3 $C_{1-6}$ alkyl groups (e.g., methyl).

In the formula (I), the substitutable position of the substituent, —Y-L$^2$-R$^2$, is preferably para-position, that is,

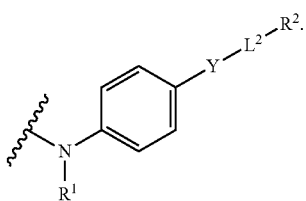

Preferable examples of compound (I) are the following compounds.

[Compound A]
A compound represented by the formula:

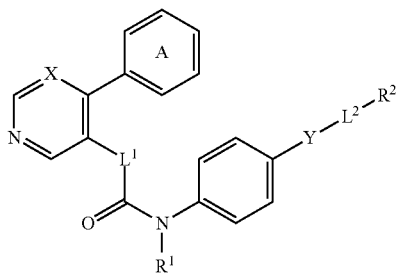

wherein
A is a benzene ring optionally substituted by 1 to 3 substituents selected from
  (1) a $C_{1-6}$ alkoxy group (e.g., methoxy), and
  (2) a halogen atom (e.g., a fluorine atom, a chlorine atom, a bromine atom),
X is CH or N,
Y is a bond or —O—,
L$^1$ is a $C_{2-6}$ alkenylene group (e.g., —CH═CH—),
L$^2$ is a $C_{1-6}$ alkylene group (e.g., methylene, ethylene),
R$^1$ is a hydrogen atom, and
R$^2$ is
(1) imidazol-1-yl, 1,3,4-oxadiazol-2-yl or morpholin-4-yl, each of which is optionally substituted by 1 to 3 $C_{1-6}$ alkyl groups (e.g., methyl),
(2) benzimidazol-1-yl optionally substituted by 1 to 3 $C_{1-6}$ alkyl groups (e.g., methyl),
(3) —PO(OCH$_3$)$_2$ or —PO(OC$_2$H$_5$)$_2$, or
(4) —S(O)$_2$CH$_3$
or a salt thereof.

[Compound B]
A compound represented by the formula:

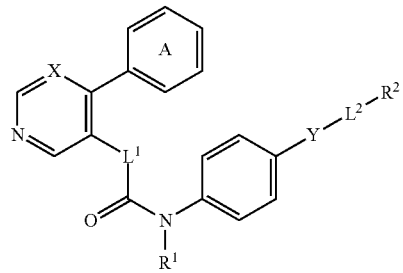

wherein
A is a benzene ring optionally substituted by 1 to 3 substituents selected from
  (1) a $C_{1-6}$ alkoxy group (e.g., methoxy), and
  (2) a halogen atom (e.g., a fluorine atom, a chlorine atom, a bromine atom),
X is CH or N,
Y is a bond,
L$^1$ is a $C_{2-6}$ alkenylene group (e.g., —CH═CH—),
L$^2$ is a $C_{1-6}$ alkylene group (e.g., methylene, ethylene),
R$^1$ is a hydrogen atom, and
R$^2$ is 1,3,4-oxadiazol-2-yl or morpholin-4-yl, each of which is optionally substituted by 1 to 3 $C_{1-6}$ alkyl groups (e.g., methyl),
or a salt thereof.

[Compound C]
(2E)-3-[4-(4-fluorophenyl)pyridin-3-yl]-N-[4-[2-(1,3,4-oxadiazol-2-yl)ethyl]phenyl}prop-2-enamide or a salt thereof.

(2E)-3-[4-(4-methoxyphenyl)pyridin-3-yl]-N-{4-[2-(1,3,4-oxadiazol-2-yl)ethyl]phenyl}prop-2-enamide or a salt thereof.

(2E)-3-[4-(4-fluorophenyl)pyridin-3-yl]-N-{4-[2-(5-methyl-1,3,4-oxadiazol-2-yl)ethyl]phenyl}prop-2-enamide or a salt thereof.

(2E)-3-[4-(4-fluorophenyl)pyrimidin-5-yl]-N-{4-[2-(1,3,4-oxadiazol-2-yl)ethyl]phenyl}prop-2-enamide or a salt thereof.

(2E)-3-[4-(4-methoxyphenyl)pyrimidin-5-yl]-N-{4-[2-(1,3,4-oxadiazol-2-yl)ethyl]phenyl}prop-2-enamide or a salt thereof.

(2E)-3-[4-(4-fluorophenyl)pyridin-3-yl]-N-[4-(morpholin-4-ylmethyl)phenyl]prop-2-enamide or a salt thereof.

[Compound D]
(2E)-3-[4-(4-fluorophenyl)pyridin-3-yl]-N-{4-[2-(1,3,4-oxadiazol-2-yl)ethyl]phenyl}prop-2-enamide or a salt thereof.

(2E)-3-[4-(4-fluorophenyl)pyrimidin-5-yl]-N-{4-[2-(1,3,4-oxadiazol-2-yl)ethyl]phenyl}prop-2-enamide or a salt thereof.

As a salt of the compound represented by the formula (I), a pharmacologically acceptable salt is preferable. Examples of such salt include salts with inorganic bases, salts with organic bases, salts with inorganic acids, salts with organic acids, salts with basic or acidic amino acids, and the like.

Preferable examples of the salts with inorganic bases include alkali metal salts such as sodium salt, potassium salt and the like; alkaline earth metal salts such as calcium salts, magnesium salts and the like; aluminum salts; ammonium salts, and the like.

Preferable examples of the salts with organic bases include salts with trimethylamine, triethylamine, pyridine, picoline, ethanolamine, diethanolamine, triethanolamine, tromethamine[tris(hydroxymethyl)methylamine], tert-butylamine, cyclohexylamine, benzylamine, dicyclohexylamine, N,N-dibenzylethylenediamine and the like.

Preferable examples of the salts with inorganic acids include salts with hydrochloric acid, hydrobromic acid, nitric acid, sulfuric acid, phosphoric acid and the like.

Preferable examples of the salts with organic acids include salts with formic acid, acetic acid, trifluoroacetic acid, phthalic acid, fumaric acid, oxalic acid, tartaric acid, maleic acid, citric acid, succinic acid, malic acid, methanesulfonic acid, benzenesulfonic acid, p-toluenesulfonic acid and the like.

Preferable examples of the salts with basic amino acids include salts with arginine, lysine, ornithine and the like.

Preferable examples of the salts with acidic amino acids include salts with aspartic acid, glutamic acid and the like.

Compound (I) may be labeled with an isotope (e.g., $^3$H, $^{11}$C, $^{14}$C, $^{18}$F, $^{35}$S, $^{125}$I) and the like.

Compound (I) may be a non-solvate (e.g., anhydride) or a solvate (e.g., hydrate).

Furthermore, a deuterated form wherein $^1$H is converted to $^2$H(D) is also encompassed in compound (I).

A prodrug of compound (I) means a compound which is converted to compound (I) with a reaction due to an enzyme or an gastric acid, etc. under the physiological condition in the living body, that is, a compound which is converted to compound (I) with enzymatic oxidation, reduction, hydrolysis and the like; a compound which is converted to compound (I) by hydrolysis and the like due to gastric acid and the like.

A prodrug of compound (I) may be a compound obtained by subjecting an amino group in compound (I) to an acylation, alkylation or phosphorylation (e.g., a compound obtained by subjecting an amino group in compound (I) to an eicosanoylation, alanylation, pentylaminocarbonylation, (5-methyl-2-oxo-1,3-dioxolen-4-yl)methoxycarbonylation, tetrahydrofuranylation, pyrrolidylmethylation, pivaloyloxymethylation or tert-butylation); a compound obtained by subjecting a hydroxy group in compound (I) to an acylation, alkylation, phosphorylation or boration (e.g., a compound obtained by subjecting an hydroxy group in compound (I) to an acetylation, palmitoylation, propanoylation, pivaloylation, succinylation, fumarylation, alanylation or dimethylaminomethylcarbonylation); a compound obtained by subjecting a carboxy group in compound (I) to an esterification or amidation (e.g., a compound obtained by subjecting a carboxy group in compound (I) to an ethyl esterification, phenyl esterification, carboxymethyl esterification, dimethylaminomethyl esterification, pivaloyloxymethyl esterification, ethoxycarbonyloxyethyl esterification, phthalidyl esterification, (5-methyl-2-oxo-1,3-dioxolen-4-yl)methyl esterification, cyclohexyloxycarbonylethyl esterification or methylamidation) and the like. These compounds can be produced from compound (I) according to a method known per se.

A prodrug of compound (I) may also be one which is converted into compound (I) under a physiological condition, such as those described in IYAKUHIN NO KAIHATSU (Development of Pharmaceuticals), Vol. 7, Design of Molecules, pp. 163-198, Published by HIROKAWA SHOTEN (1990).

The production methods of compound (I) are explained in the following.

Compound (I) of the present invention can be produced, for example, by the method shown in the following Reaction Scheme 1. In the following reaction schemes, each starting compound may form a salt as long as it does not inhibit the reaction, and examples of the salt include those exemplified as the salts of the compound represented by the aforementioned formula (I) can be used.

The starting compounds without indication of specific production method are easily commercially available, or can be produced according to a method known per se or a method analogous thereto.

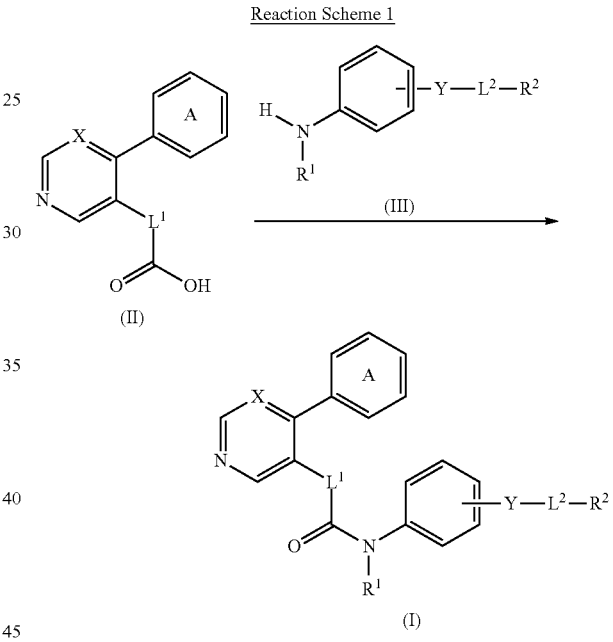

wherein each symbol is as defined above.

In this method, compound (I) can be produced by subjecting compound (II) to an amidation reaction. This reaction is performed by a method known per se, for example, a method of directly condensing compound (II) with compound (III), a method of reacting a reactive derivative of compound (II) with compound (III), and the like.

The method of directly condensing compound (II) with compound (III) is generally performed in the presence of a condensing agent in a solvent that does not adversely influence the reaction.

Examples of the condensing agent include carbodiimide condensing agents such as dicyclohexylcarbodiimide, diisopropylcarbodiimide, 1-ethyl-3-(3-dimethylaminopropyl)carbodiimide and hydrochloride thereof, and the like; phosphoric acid condensing agents such as diethyl cyanophosphate, diphenylphosphoryl azide, bis(2-oxo-3-oxazolidinyl)phosphinic chloride and the like; conventionally-used condensing agents such as carbonyldiimidazole, 2-chloro-1,3-dimethylimidazolium tetrafluoroborate and the like; and the like.

Examples of the solvent that does not adversely influence the reaction include amides such as N,N-dimethylformamide, N,N-dimethylacetamide and the like; halogenated hydrocarbons such as chloroform, dichloromethane and the like; aromatic hydrocarbons such as benzene, toluene and the like; ethers such as tetrahydrofuran, dioxane, diethyl ether and the like; esters such as ethyl acetate and the like; nitriles such as acetonitrile and the like; sulfoxides such as dimethyl sulfoxide and the like; water and the like. Two or more kinds of these solvents may be mixed at an appropriate ratio for use.

The amount of compound (III) to be used is generally 1-10 mol, preferably 1-3 mol, per 1 mol of compound (II).

The amount of the condensing agent to be used is generally 1-10 mol, preferably 1-3 mol, per 1 mol of compound (II).

When the above-mentioned carbodiimide condensing agent is used as a condensing agent, the reaction efficiency can be improved by using a suitable condensation promoter (e.g., 1-hydroxy-1H-1,2,3-benzotriazole, 1-hydroxy-1H-1,2,3-benzotriazole hydrate, 1-hydroxy-7-azabenzotriazole, N-hydroxysuccinimide, N-hydroxyphthalimide etc.) as necessary. When the above-mentioned phosphoric acid condensing agent is used as a condensing agent, the reaction efficiency can be generally improved by adding an organic amine base such as triethylamine and the like.

The amount of the above-mentioned condensation promoter or organic amine base to be used is generally 1-10 mol, preferably 1-3 mol, per 1 mol of compound (II).

The reaction temperature is generally −30-100° C.

The reaction time is generally 0.5-60 hr.

Examples of the aforementioned reactive derivative of compound (II) include acid anhydrides, acid halides (acid chlorides, acid bromides), imidazolides, mixed acid anhydrides (for example, anhydrides with methyl carbonate, ethyl carbonate, isobutyl carbonate etc.) and the like.

For example, when an acid anhydride or an acid halide is used as a reactive derivative, the reaction is generally performed in the presence of a base in a solvent that does not adversely influence the reaction.

Examples of the base include triethylamine, diisopropylethylamine, pyridine, N-methylmorpholine, N,N-dimethylaniline, 4-dimethylaminopyridine, lithium hydroxide, sodium hydroxide, potassium hydroxide, sodium hydrogen carbonate, sodium carbonate, potassium carbonate, cesium carbonate and the like.

Examples of the solvent that does not adversely influence the reaction include amides such as N,N-dimethylformamide, N,N-dimethylacetamide and the like; halogenated hydrocarbons such as chloroform, dichloromethane and the like; aromatic hydrocarbons such as benzene, toluene and the like; ethers such as tetrahydrofuran, dioxane, diethyl ether and the like; esters such as ethyl acetate and the like; nitriles such as acetonitrile and the like; water, and the like. Two or more kinds of these solvents may be mixed at an appropriate ratio for use. When the above-mentioned amide is used as a solvent that does not adversely influence the reaction, the reaction can also be performed in the absence of a base.

The amount of compound (III) to be used is generally 1-10 mol, preferably 1-3 mol, per 1 mol of the reactive derivative of compound (II).

The amount of the base to be used is generally 1-10 equivalents, preferably 1-3 equivalents, relative to the reactive derivative of compound (II).

The reaction temperature is generally −30 to 100° C.

The reaction time is generally 0.5 to 20 hr.

When a mixed acid anhydride is used as a reactive derivative, compound (II) is reacted with a chlorocarbonate in the presence of a base, and then further reacted with compound (III).

Examples of the chlorocarbonate include methyl chlorocarbonate, ethyl chlorocarbonate, isobutyl chlorocarbonate and the like.

Examples of the base include triethylamine, aniline, N-methylmorpholine, N,N-dimethylaniline, 4-dimethylaminopyridine, sodium hydroxide, potassium hydroxide, lithium hydroxide, sodium hydrogen carbonate, sodium carbonate, potassium carbonate, cesium carbonate and the like.

The amount of compound (III) to be used is generally 1-10 mol, preferably 1-3 mol, per 1 mol of compound (II).

The amount of the chlorocarbonate to be used is generally 1-10 mol, preferably 1-3 mol, per 1 mol of compound (II).

The amount of the base to be used is generally 1-10 equivalents, preferably 1-3 equivalents, relative to compound (II).

The reaction temperature is generally −20-100° C.

The reaction time is generally 0.5-20 hr.

The thus-obtained compound (I) can be isolated and purified by a known separation and purification means, for example, concentration, concentration under reduced pressure, solvent extraction, crystallization, recrystallization, phase transfer, chromatography and the like.

Compound (III) used as a starting compound in the above-mentioned Reaction Scheme 1 can be produced by a method known per se, for example, the method described in I L Farmaco, 1992, vol. 47, page 335, Journal of Medicinal Chemistry, 1975, vol. 18, page 833, Journal of Medicinal Chemistry, 2000, vol. 43, page 2049, WO 2003/106416, WO 2004/39365 and the like or a method analogous thereto.

Compound (II) or a salt thereof can be produced by a method shown in the following Reaction Scheme 2.

Reaction Scheme 2 wherein $R^{20}$ is an optionally substituted $C_{1-6}$ alkyl group, and other symbols are as defined above.

In this method, compound (II) can be produced by subjecting compound (IV) or compound (V) to hydrolysis. This reaction is performed by a method known per se in the presence of an acid or a base in a solvent containing water.

Examples of the acid include hydrochloric acid, sulfuric acid, acetic acid, hydrobromic acid and the like.

Examples of the base include alkali metal carbonates such as potassium carbonate, sodium carbonate, cesium carbonate and the like; alkaline earth metal carbonates such as barium carbonate, calcium carbonate and the like; alkali metal alkoxides such as sodium methoxide; alkali metal hydroxides such as potassium hydroxide, sodium hydroxide, lithium hydroxide and the like; alkaline earth metal hydroxides such as barium hydroxide, calcium hydroxide and the like; and the like.

The amount of the acid or base to be used is generally an excess amount relative to compound (IV) or compound (V). Preferably, the amount of the acid to be used is about 2- about 50 equivalents relative to compound (IV) or compound (V), and the amount of the base to be used is about 1.2- about 10 equivalents relative to compound (IV) or compound (V).

Examples of the water-containing solvent include a mixed solvent of water and one or more kinds of solvents selected from alcohols such as methanol, ethanol and the like; ethers such as tetrahydrofuran, dioxane, diethyl ether and the like; sulfoxides such as dimethyl sulfoxide and the like; ketones such as acetone and the like; and the like. When the hydrolysis is performed using an acid, an excess acid may be used as a solvent.

The reaction temperature is generally about −20- about 150° C., preferably about −10- about 100° C.

The reaction time is generally about 0.1- about 20 hr.

The thus-obtained compound (II) can be isolated and purified by a known separation and purification means, for example, concentration, concentration under reduced pressure, solvent extraction, crystallization, recrystallization, phase transfer, chromatography and the like.

Compound (II-1), which is compound (II) or salt thereof wherein $L^1$ is —CH=CH—, can also be produced by the method shown in the following Reaction Scheme 3.

nopyridine, N,N-dimethylaniline, N-methylpiperidine, N-methylpyrrolidine, N-methylmorpholine and the like; and the like.

Preferable examples of the solvent that does not adversely influence the reaction include ethers such as diethyl ether, diisopropyl ether, diphenyl ether, tetrahydrofuran, 1,4-dioxane, 1,2-dimethoxyethane and the like; aromatic hydrocarbons such as benzene, toluene and the like; saturated hydrocarbons such as cyclohexane, hexane and the like; amides such as N,N-dimethylformamide, N,N-dimethylacetamide, hexamethylphosphoric triamide and the like; halogenated hydrocarbons such as dichloromethane, chloroform, carbon tetrachloride, 1,2-dichloroethane and the like; nitriles such as acetonitrile, propionitrile and the like; esters such as methyl acetate, ethyl acetate, butyl acetate and the like; sulfoxides such as dimethyl sulfoxide and the like; alcohols such as methanol, ethanol and the like; water; mixed solvents thereof; and the like.

The amount of the malonic acid to be used is generally 1-10 mol, preferably 1-3 mol, per 1 mol of compound (VI).

The amount of the base to be used is generally 0.01-10 equivalents, preferably 0.1-1 equivalents, relative to compound (VI).

The reaction temperature is generally −30° C.-100° C.

The reaction time is generally 0.5-20 hr.

The thus-obtained compound (II-1) can be isolated and purified by a known separation and purification means, for example, concentration, concentration under reduced pressure, solvent extraction, crystallization, recrystallization, phase transfer, chromatography and the like.

Compound (IV) to be used as a starting compound in Reaction Scheme 2 can be produced by a method known per se. For example, compound (IV-1), which are compound (IV) or a salt thereof wherein $L^1$ is —CH=CH—, and compound (IV-2), which are compound (IV) or a salt thereof wherein $L^1$ is —CH$_2$CH$_2$—, can be produced by the method shown in the following Reaction Scheme 4.

Reaction Scheme 3

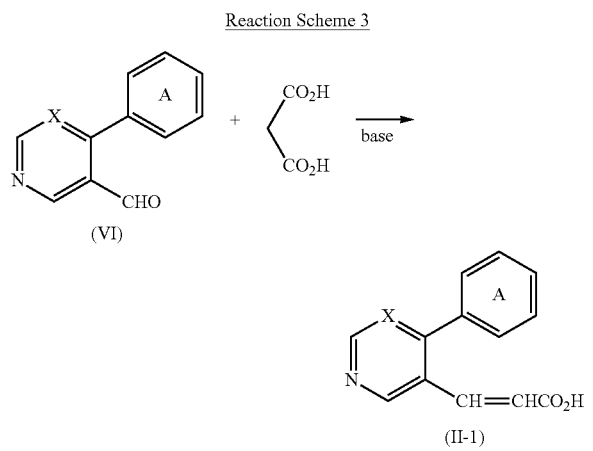

Reaction Scheme 4

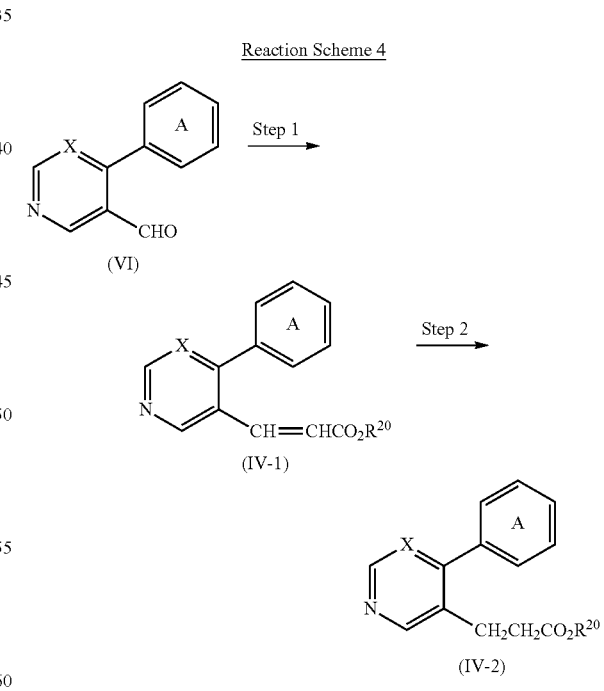

wherein each symbol is as defined above.

Compound (II-1) can be produced by subjecting compound (VI) to a Knoevenagel condensation reaction [Organic Reactions, 1942, vol 1. page 210 or Organic Reactions, 1967, vol. 15, page 204] or a method analogous thereto.

This reaction is performed by reacting compound (VI) with malonic acid in the presence of a base in a solvent that does not adversely influence the reaction.

Examples of the base include aromatic amines such as pyridine, lutidine and the like; secondary amines such as diethylamine, dipropylamine, dibutylamine, piperidine, pyrrolidine, morpholine and the like; tertiary amines such as triethylamine, tripropylamine, tributylamine, N-ethyldiisopropylamine, cyclohexyldimethylamine, 4-dimethylamiwherein each symbol is as defined above.

(Step 1) Homolongation Reaction

In this step, compound (IV-1) can be produced by reacting compound (VI) with an organic phosphorus reagent in the presence of a base in a solvent that does not adversely influence the reaction.

Examples of the organic phosphorus reagent include methyl dimethylphosphonoacetate, ethyl diethylphosphonoacetate, ethyl dimethylphosphonoacetate and the like.

The amount of the organic phosphorus reagent to be used is preferably about 1-10 mol per 1 mol of compound (VI).

Examples of the base include alkali metal salts such as potassium hydroxide, sodium hydroxide, sodium hydrogen carbonate, potassium carbonate and the like; alkaline earth metal salts such as barium carbonate, calcium carbonate, barium hydroxide, calcium hydroxide and the like; amines such as pyridine, triethylamine, N,N-dimethylaniline, 1,8-diazabicyclo[5.4.0]undec-7-ene and the like; metal hydrides such as potassium hydride, sodium hydride and the like; alkali metal alkoxides such as sodium methoxide, sodium ethoxide, potassium tert-butoxide and the like; and the like.

The amount of the base to be used is preferably about 1- about 5 equivalents relative to compound (VI).

Examples of the solvent that does not adversely influence the reaction include aromatic hydrocarbons such as benzene, toluene, xylene and the like; ethers such as tetrahydrofuran, dioxane, diethyl ether and the like; halogenated hydrocarbons such as chloroform, dichloromethane and the like; amides such as N,N-dimethylformamide and the like; nitriles such as acetonitrile and the like; sulfoxides such as dimethyl sulfoxide and the like; and the like. Two or more kinds of these solvents may be mixed at an appropriate ratio for use.

The reaction temperature is generally about −50- about 150° C., preferably about −10- about 100° C.

The reaction time is generally about 0.5- about 20 hr.

The thus-obtained compound (IV-1) can be isolated and purified by a known separation and purification means, for example, concentration, concentration under reduced pressure, solvent extraction, crystallization, recrystallization, phase transfer, chromatography and the like. In addition, a reaction mixture containing compound (IV-1) without separation and purification of compound (IV-1) may be used as a starting material of the next reaction.

(Step 2) Hydrogenation Reaction

This reaction is performed by a method known per se under a hydrogen atmosphere or in the presence of a hydrogen source such as formic acid and the like, and in the presence of a metal catalyst, in a solvent that does not adversely influence the reaction.

Examples of the metal catalyst include transition metal catalysts such as palladium-carbon, palladium-barium carbonate, palladium black, platinum oxide, platinum-carbon, Raney-nickel, Wilkinson's catalyst and the like; and the like.

The amount of the metal catalyst to be used is preferably about 0.01- about 10 mol per 1 mol of compound (IV-1).

Examples of the solvent that does not adversely influence the reaction include aromatic hydrocarbons such as benzene, toluene, xylene and the like; ethers such as tetrahydrofuran, dioxane, diethyl ether and the like; halogenated hydrocarbons such as chloroform, dichloromethane and the like; amides such as N,N-dimethylformamide and the like; alcohols such as methanol, ethanol, isopropanol and the like; and the like. Two or more kinds of these solvents may be mixed at an appropriate ratio for use.

The reaction temperature is generally about −50- about 150° C., preferably about −10- about 100° C.

The reaction time is generally about 0.5- about 20 hr.

The thus-obtained compound (IV-2) can be isolated and purified by a known separation and purification means, for example, concentration, concentration under reduced pressure, solvent extraction, crystallization, recrystallization, phase transfer, chromatography and the like.

Compound (VI) to be used as a starting compound in the above-mentioned Reaction Schemes 3 and 4 can be produced by a method known per se, for example, the method described in Heterocycles, 1980, vol. 14, page 2583, Journal of Chemical Society, Perkin Transaction 1, 2001, page 2583, Bioorganic and Medicinal Chemistry Letters, 2007, vol. 17, page 662, Organic Letters, 2005, vol. 7, page 4673, Chemical and Pharmaceutical Bulletin, 1993, vol. 41, page 139, WO 2004/48365, US 2006/142576, U.S. Pat. No. 6,509,329, WO 2005/75458 and the like, or a method analogous thereto.

Compound (V) or a salt thereof can be produced by a method shown in the following Reaction Scheme 5.

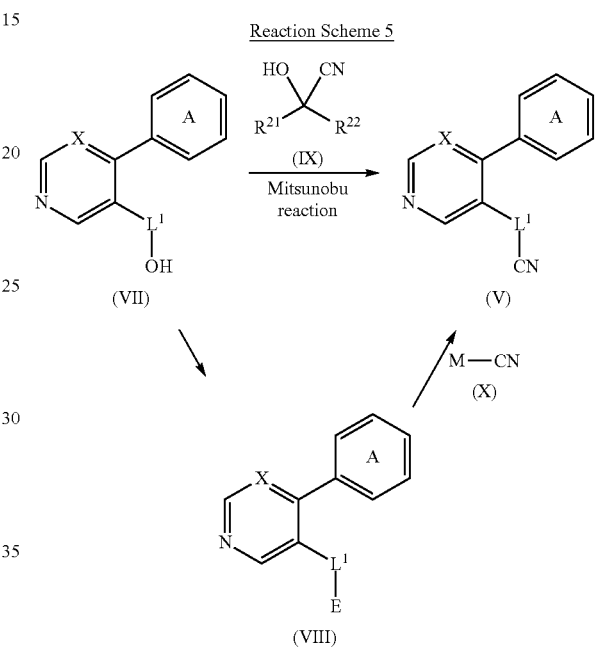

wherein $R^{21}$ and $R^{22}$ are each independently an optionally substituted $C_{1-6}$ alkyl group, E is a leaving group (e.g., a halogen atom, an alkylsulfonyloxy group, an arylsulfonyloxy group or the like), M is a metal (e.g., potassium, sodium, lithium, magnesium, calcium, copper, mercury, zinc or the like, which may be complexed), and each symbol is as defined above.

Compound (V) can be produced, for example, by subjecting compound (VII) to a Mitsunobu reaction with compound (IX).

This reaction is performed by a method known per se in the presence of a phosphine compound and an azo compound in a solvent that does not adversely influence the reaction.

Examples of the phosphine compound include trimethylphosphine, triethylphosphine, tributylphosphine, triphenylphosphine, diphenylpyridylphosphine, cyanomethylenetributylphosphorane and the like.

Examples of the azo compound include diethyl azodicarboxylate, diisopropyl azodicarboxylate, azodicarbonyldipiperidine and the like.

The amount of compound (IX) to be used is generally 1-20 equivalents, preferably 1-10 equivalents, per 1 mol of compound (VII).

The amount of the phosphine compound and azo compound to be used is generally 1-50 equivalents, preferably 1-10 equivalents, per 1 mol of compound (VII), respectively.

Examples of the solvent that does not adversely influence the reaction include aromatic hydrocarbons such as benzene, toluene, xylene and the like; ethers such as tetrahydrofuran, dioxane, diethyl ether and the like; halogenated hydrocarbons such as chloroform, dichloromethane and the like; amides such as N,N-dimethylformamide and the like; and the like. Two or more kinds of these solvents may be mixed at an appropriate ratio for use.

The reaction temperature is generally about −20- about 150° C., preferably about −10- about 100° C.

The reaction time is generally about 0.1- about 20 hr.

The thus-obtained compound (V) can be isolated and purified by a known separation and purification means, for example, concentration, concentration under reduced pressure, solvent extraction, crystallization, recrystallization, phase transfer, chromatography and the like.

Compound (V) can also be produced by converting compound (VII) to compound (VIII), which is a reactive derivative thereof, and reacting compound (VIII) with metal cyanide (X).

Compound (VIII) can be produced by reacting compound (VII) with a suitable activating reagent in the presence of a base as necessary, in a solvent that does not adversely influence the reaction.

As the activating reagent, a reagent corresponding to the aforementioned leaving group E can be used. Specific examples of the activating reagent include thionyl chloride, methanesulfonyl chloride, benzenesulfonyl chloride, p-toluenesulfonyl chloride and the like.

The amount of the activating reagent to be used is preferably about 1- about 10 mol per 1 mol of compound (VII).

Examples of the base include alkali metal salts such as potassium hydroxide, sodium hydroxide, sodium hydrogen carbonate, potassium carbonate and the like; alkaline earth metal salts such as barium carbonate, calcium carbonate, barium hydroxide, calcium hydroxide and the like; amines such as pyridine, triethylamine, N,N-dimethylaniline, 1,8-diazabicyclo[5.4.0]undec-7-ene and the like; metal hydrides such as potassium hydride, sodium hydride and the like; alkali metal alkoxides such as sodium methoxide, sodium ethoxide, potassium tert-butoxide and the like; and the like.

The amount of the base to be used is preferably about 1- about 10 equivalents relative to compound (VII).

Examples of the solvent that does not adversely influence the reaction include aromatic hydrocarbons such as benzene, toluene, xylene and the like; ethers such as tetrahydrofuran, dioxane, diethyl ether and the like; halogenated hydrocarbons such as chloroform, dichloromethane and the like; amides such as N,N-dimethylformamide and the like; nitriles such as acetonitrile and the like; and the like. Two or more kinds of these solvents may be mixed at an appropriate ratio for use.

The reaction temperature is generally about −20- about 150° C., preferably about −10- about 100° C.

The reaction time is generally about 0.1- about 20 hr.

The thus-obtained compound (VIII) can be isolated and purified by a known separation and purification means, for example, concentration, concentration under reduced pressure, solvent extraction, crystallization, recrystallization, phase transfer, chromatography and the like. In addition, a reaction mixture containing compound (VIII) without separation and purification of compound (VIII) may be used as a starting material of the next reaction.

The reaction of compound (VIII) with metal cyanide (X) is performed in a solvent that does not adversely influence the reaction.

Examples of the solvent that does not adversely influence the reaction include aromatic hydrocarbons such as benzene, toluene, xylene and the like; ethers such as tetrahydrofuran, dioxane, diethyl ether and the like; halogenated hydrocarbons such as chloroform, dichloromethane and the like; alcohols such as methanol, ethanol and the like; amides such as N,N-dimethylformamide and the like; nitriles such as acetonitrile and the like; sulfoxides such as dimethyl sulfoxide and the like; and the like. Two or more kinds of these solvents may be mixed at an appropriate ratio for use, or may be mixed with water. When the aforementioned solvent is in a mixture with water, the mixing ratio of water is, for example, 0.1-1000%, preferably 1-100%, relative to the solvent in volume ratio.

The amount of metal cyanide (X) to be used is generally 1-20 equivalents, preferably 1-10 equivalents, per 1 mol of compound (VIII).

The reaction temperature is generally about −20- about 150° C., preferably about −10- about 100° C.

The reaction time is generally about 0.1- about 20 hr.

The thus-obtained compound (V) can be isolated and purified by a known separation and purification means, for example, concentration, concentration under reduced pressure, solvent extraction, crystallization, recrystallization, phase transfer, chromatography and the like.

Compound (VII) to be used as a starting compound in the above-mentioned Reaction Scheme 5 can be produced by a method known per se or a method analogous thereto.

For example, compound (VII-1) which is compound (VII) wherein $L^1$ is —$CH_2$—, compound (VII-2) which is compound (VII) wherein $L^1$ is —CH=$CHCH_2$—, and compound (VII-3) which is compound (VII) wherein $L^1$ is —$CH_2CH_2CH_2$— can be produced by subjecting compound (VI), compound (IV-1) or compound (IV-2) shown in the above-mentioned Reaction Scheme 4 to a reduction reaction known per se or a method analogous thereto, respectively.

In the above-mentioned reactions, when the starting compound has an amino group, a carboxy group, a hydroxy group, a carbonyl group or a mercapto group as a substituent, a protecting group generally used in peptide chemistry and the like may be introduced into these groups. By removing the protecting group as necessary after the reaction, the objective compound can be obtained.

Examples of the amino-protecting group include a formyl group, a $C_{1-6}$ alkyl-carbonyl group, a $C_{1-6}$ alkoxy-carbonyl group, a benzoyl group, a $C_{7-10}$ aralkyl-carbonyl group (e.g., benzylcarbonyl), a $C_{7-14}$ aralkyloxy-carbonyl group (e.g., benzyloxycarbonyl, a 9-fluorenylmethoxycarbonyl), a trityl group, a phthaloyl group, an N,N-dimethylaminomethylene group, a substituted silyl group (e.g., trimethylsilyl, triethylsilyl, dimethylphenylsilyl, tert-butyldimethylsilyl, tert-butyldiethylsilyl), a $C_{2-6}$ alkenyl group (e.g., 1-allyl) and the like. These protecting groups are optionally substituted by 1 to 3 substituents selected from a halogen atom, a $C_{1-6}$ alkoxy group and a nitro group.

Examples of the carboxy-protecting group include a $C_{1-6}$ alkyl group, a $C_{7-11}$ aralkyl group (e.g., benzyl), a phenyl group, a trityl group, a substituted silyl group (e.g., trimethylsilyl, triethylsilyl, dimethylphenylsilyl, tert-butyldimethylsilyl, tert-butyldiethylsilyl), a $C_{2-6}$ alkenyl group (e.g., 1-allyl) and the like. These protecting groups are optionally substituted by 1 to 3 substituents selected from a halogen atom, a $C_{1-6}$ alkoxy group and a nitro group.

Examples of the hydroxy-protecting group include a $C_{1-6}$ alkyl group, a phenyl group, a trityl group, a $C_{7-10}$ aralkyl group (e.g., benzyl), a formyl group, a $C_{1-6}$ alkyl-carbonyl group, a benzoyl group, a $C_{7-10}$ aralkyl-carbonyl group (e.g., benzylcarbonyl), a 2-tetrahydropyranyl group, a 2-tetrahydrofuranyl group, a substituted silyl group (e.g., trimethylsilyl, triethylsilyl, dimethylphenylsilyl, tert-butyldimethylsilyl, tert-butyldiethylsilyl), a $C_{2-6}$ alkenyl group (e.g., 1-allyl) and the like. These protecting-groups are optionally substituted by 1 to 3 substituents selected from a halogen atom, a $C_{1-6}$ alkyl group, a $C_{1-6}$ alkoxy group and a nitro group.

Examples of the protected carbonyl group include a cyclic acetal (e.g., 1,3-dioxane), an acyclic acetal (e.g., di-$C_{1-6}$ alkyl acetal) and the like.

Examples of the mercapto-protecting group include a $C_{1-6}$ alkyl group, a phenyl group, a trityl group, a $C_{7-10}$ aralkyl group (e.g., benzyl), a $C_{1-6}$ alkyl-carbonyl group, a benzoyl group, a $C_{7-10}$ aralkyl-carbonyl group (e.g., benzylcarbonyl), a $C_{1-6}$ alkoxy-carbonyl group, a $C_{6-14}$ aryloxy-carbonyl group (e.g., phenyloxycarbonyl), a $C_{7-14}$ aralkyloxy-carbonyl group (e.g., benzyloxycarbonyl, 9-fluorenylmethoxycarbonyl), a 2-tetrahydropyranyl group, a $C_{1-6}$ alkylamino-carbonyl group (e.g., methylaminocarbonyl, ethylaminocarbonyl) and the like. These protecting groups are optionally substituted by 1 to 3 substituents selected from a halogen atom, a $C_{1-6}$ alkyl group, a $C_{1-6}$ alkoxy group and a nitro group.

Examples of the method for removing the above-mentioned protecting group include a method known per se, for example, the method described in Protective Groups in Organic Synthesis, John Wiley and Sons (1980) and the like. Specifically, a method using acid, base, ultraviolet rays, hydrazine, phenylhydrazine, sodium N-methyldithiocarbamate, tetrabutylammonium fluoride, palladium acetate, trialkylsilyl halide (e.g., trimethylsilyl iodide, trimethylsilyl bromide) and the like, a reduction method and the like.

Compound (I) obtained by each of the above-mentioned production methods can be isolated and purified by a known means such as concentration, concentration under reduced pressure, solvent extraction, crystallization, recrystallization, phase transfer, chromatography and the like. Each starting compound obtained by each of the above-mentioned production methods can be isolated and purified by a known means similar to those mentioned above. In addition, these starting compounds may be used without isolation as a reaction mixture and as a starting material of the next reaction.

When compound (I) contains an optical isomer, a stereoisomer, a positional isomer and a rotamer, these are also included in compound (I), as well as each can be obtained as a single product by a synthesis method or separation method known per se. For example, when compound (I) contains an optical isomer, an optical isomer resolved from the compound is also encompassed in compound (I).

Compound (I) may also be a crystal.

The crystal of compound (I) (hereinafter sometimes to be abbreviated as the crystal of the present invention) can be produced by crystallizing compound (I) by applying a crystallization method known per se.

In the present specification, the melting point means, for example, a melting point measured by a trace melting point measurement device (YANACO, MP-500D type or Buchi, B-545 type) or DSC (Differential scanning calorimetry) apparatus (SEIKO, EXSTAR6000) and the like.

Generally, the melting point sometimes varies depending on the measurement device, measurement condition and the like. The crystal in the present specification may be a crystal showing a melting point different from the values described in the present specification as long as the difference is within a general error range.

Compound (I) may be a pharmaceutically acceptable cocrystal or cocrystal salt. Here, the cocrystal or cocrystal salt means a crystalline substance constituted by two or more kinds of special solids each having different physical properties (e.g., structure, melting point, melting heat and the like) at room temperature. The cocrystal or cocrystal salt can be produced by a cocrystallization method known per se.

The crystal of the present invention is superior in the physicochemical properties (e.g., melting point, solubility, stability) and biological properties (e.g., pharmacokinetics (absorbability, distribution, metabolism, excretion), efficacy expression) and extremely useful as a medicament.

Compound (I) or a prodrug thereof (hereinafter sometimes to be abbreviated as the compound of the present invention) shows low toxicity and can be used as an agent for the prophylaxis or treatment of various diseases to be mentioned later for mammals (e.g., humans, mice, rats, rabbits, dogs, cats, bovines, horses, pigs, monkeys) as they are or by admixing with a pharmacologically acceptable carrier and the like to give a pharmaceutical composition.

Here, various organic or inorganic carriers conventionally used as materials for pharmaceutical preparations are used as a pharmacologically acceptable carrier, which are added as excipient, lubricant, binder and disintegrant for solid preparations; solvent, solubilizing agent, suspending agent, isotonicity agent, buffer and soothing agent for liquid preparations, and the like. Where necessary, an additive for pharmaceutical preparations such as preservative, antioxidant, colorant, sweetening agent and the like can be used.

Preferable examples of the excipient include lactose, sucrose, D-mannitol, D-sorbitol, starch, pregelatinized starch, dextrin, microcrystalline cellulose, low-substituted hydroxypropyl cellulose, sodium carboxymethylcellulose, gum arabic, pullulan, light anhydrous silicic acid, synthetic aluminum silicate and magnesium aluminate metasilicate.

Preferred examples of the lubricant include magnesium stearate, calcium stearate, talc and colloidal silica.

Preferable examples of the binder include pregelatinized starch, saccharose, gelatin, gum arabic, methylcellulose, carboxymethylcellulose, sodium carboxymethylcellulose, microcrystalline cellulose, sucrose, D-mannitol, trehalose, dextrin, pullulan, hydroxypropyl cellulose, hydroxypropyl methylcellulose and polyvinylpyrrolidone.

Preferable examples of the disintegrant include lactose, sucrose, starch, carboxymethylcellulose, calcium carboxymethylcellulose, croscarmellose sodium, sodium carboxymethyl starch, light anhydrous silicic acid and low-substituted hydroxypropyl cellulose.

Preferable examples of the solvent include water for injection, physiological saline, Ringer's solution, alcohol, propylene glycol, polyethylene glycol, sesame oil, corn oil, olive oil and cottonseed oil.

Preferred examples of the solubilizing agent include polyethylene glycol, propylene glycol, D-mannitol, trehalose, benzyl benzoate, ethanol, tris(hydroxymethyl)aminomethane, cholesterol, triethanolamine, sodium carbonate, sodium citrate, sodium salicylate and sodium acetate.

Preferred examples of the suspending agent include surfactants such as stearyltriethanolamine, sodium lauryl sulfate, laurylaminopropionic acid, lecithin, benzalkonium chloride, benzethonium chloride, glyceryl monostearate and the like; hydrophilic polymers such as polyvinyl alcohol, polyvinylpyrrolidone, sodium carboxymethylcellulose, methylcellulose, hydroxymethyl cellulose, hydroxyethyl cellulose, hydroxypropyl cellulose and the like; polysorbates; and polyoxyethylene hydrogenated castor oil.

Preferred examples of the isotonicity agent include sodium chloride, glycerol, D-mannitol, D-sorbitol and glucose.

Preferred examples of the buffer include buffers such as phosphates, acetates, carbonates and citrates.

Preferred examples of the soothing agent include benzyl alcohol.

Preferred examples of the preservative include p-hydroxybenzoate, chlorobutanol, benzyl alcohol, phenethyl alcohol, dehydroacetic acid and sorbic acid.

Preferred examples of the antioxidant include sulfites and ascorbates.

Preferable examples of the colorant include water-soluble edible tar pigments (e.g., food colors such as Food Color Red Nos. 2 and 3, Food Color Yellow Nos. 4 and 5, Food Color Blue Nos. 1 and 2 and the like), water insoluble lake pigments (e.g., aluminum salts of the aforementioned water-soluble edible tar pigment), and natural pigments (e.g., beta-carotene, chlorophyll, red iron oxide).

Preferable examples of the sweetening agent include saccharin sodium, dipotassium glycyrrhizinate, aspartame and stevia.

The medicament containing the compound of the present invention can be safely administered solely or by mixing with a pharmacologically acceptable carrier according to a method known per se (e.g., the method described in the Japanese Pharmacopoeia etc.) as a production method of a pharmaceutical preparation, and in the form of, for example, tablet (including sugar-coated tablet, film-coated tablet, sublingual tablet, orally disintegrating tablet, buccal and the like), pill, powder, granule, capsule (including soft capsule, microcapsule), troche, syrup, liquid, emulsion, suspension, release control preparation (e.g., immediate-release preparation, sustained-release preparation, sustained-release microcapsule), aerosol, film (e.g., orally disintegrating film, oral mucosa-adhesive film), injection (e.g., subcutaneous injection, intravenous injection, intramuscular injection, intraperitoneal injection), drip infusion, transdermal absorption preparation, ointment, lotion, adhesive preparation, suppository (e.g., rectal suppository, vaginal suppository), pellet, nasal preparation, pulmonary preparation (inhalation), eye drop and the like, orally or parenterally (e.g., intravenous, intramuscular, subcutaneous, intraorgan, intranasal, intradermal, instillation, intracerebral, intrarectal, intravaginal, intraperitoneal and intratumor administrations, administration to the vicinity of tumor, and direct administration to the lesion).

A pharmaceutical composition can be produced by a method conventionally used in the technical field of pharmaceutical preparation, for example, the method described in the Japanese Pharmacopoeia and the like.

While the content of the compound of the present invention in the pharmaceutical composition varies depending on the dosage form, dose of the compound of the present invention, and the like, it is, for example, about 0.1 to 100 wt %.

During production of an oral preparation, coating may be applied as necessary for the purpose of masking of taste, enteric property or durability.

Examples of the coating base to be used for coating include sugar coating base, aqueous film coating base, enteric film coating base and sustained-release film coating base.

As the sugar coating base, sucrose is used. Moreover, one or more kinds selected from talc, precipitated calcium carbonate, gelatin, gum arabic, pullulan, carnauba wax and the like may be used in combination.

Examples of the aqueous film coating base include cellulose polymers such as hydroxypropyl cellulose, hydroxypropyl methyl cellulose, hydroxyethyl cellulose, methylhydroxyethyl cellulose and the like; synthetic polymers such as polyvinylacetal diethylaminoacetate, aminoalkyl methacrylate copolymer E [Eudragit E (trade name)], polyvinylpyrrolidone and the like; and polysaccharides such as pullulan and the like.

Examples of the enteric film coating base include cellulose polymers such as hydroxypropyl methyl cellulose phthalate, hydroxypropyl methyl cellulose acetate succinate, carboxymethylethyl cellulose, cellulose acetate phthalate and the like; acrylic polymers such as methacrylic acid copolymer L [Eudragit L (trade name)], methacrylic acid copolymer LD [Eudragit L-30D55 (trade name)], methacrylic acid copolymer S [Eudragit S (trade name)] and the like; and naturally occurring substances such as shellac and the like.

Examples of the sustained-release film coating base include cellulose polymers such as ethyl cellulose and the like; and acrylic polymers such as aminoalkyl methacrylate copolymer RS [Eudragit RS (trade name)], ethyl acrylate-methyl methacrylate copolymer suspension [Eudragit NE (trade name)] and the like.

The above-mentioned coating bases may be used after mixing with two or more kinds thereof at appropriate ratios. For coating, for example, a light shielding agent such as titanium oxide, red ferric oxide and the like can be used.

The compound of the present invention shows low toxicity (e.g., acute toxicity, chronic toxicity, genetic toxicity, reproductive toxicity, cardiotoxicity, carcinogenicity and the like) and a few side effects. Therefore, it can be used as an agent for the prophylaxis or treatment or a diagnostic of various diseases in a mammal (e.g., human, bovine, horse, dog, cat, monkey, mouse, rat).

Since the compound of the present invention has a muscle cell differentiation promoting activity, it is useful as an agent for the prophylaxis or treatment of diseases developed by or whose development is promoted by the suppression of muscle differentiation or a factor induced by the suppression of muscle differentiation.

Examples of the disease developed by or whose development is promoted by the suppression of muscle differentiation or a factor induced by the suppression of muscle differentiation include diabetes, glucose tolerance disorders, ketosis, acidosis, diabetic complications [e.g., neuropathy, nephropathy, retinopathy, cataract, macroangiopathy, osteopenia, diabetic hyperosmolar coma, infections (e.g., respiratory infection, urinary tract infection, gastrointestinal infection, skin and soft tissue infections, foot infection), diabetic gangrene, xerostomia, hypacusis, cerebrovascular disorder, peripheral circulatory failure], obesity and complications of obesity, sleep apnea syndrome, osteoporosis, cachexia (e.g., cancerous cachexia, tuberculous cachexia, diabetic cachexia, hemopathic cachexia, endocrinopathic cachexia, infectious cachexia or cachexia induced by acquired immunodeficiency syndrome etc.), fatty liver, non-alcoholic steatohepatitis, hypertension, polycystic ovary syndrome, renal disease (e.g., diabetic nephropathy, glomerulonephritis, glomerulosclerosis, nephrotic syndrome, hypertensive nephrosclerosis, end-stage renal disorder etc.), myogenic muscular atrophy (muscular dystrophy, myotonic dystrophy, myopathy etc.), neurogenic muscular atrophy (amyotrophic lateral sclerosis, spinobulbar muscular atrophy, spinal muscular atrophy, hereditary neuropathy etc.), disuse muscular atrophy, sarcopenia, myocardial infarction, angina pectoris, cardiac failure, cerebrovascular disorder (e.g., cerebral infarction, cerebral apoplexy etc.), insulin resistance syndrome, syndrome X, metabolic syndrome (pathology involving not less than three selected from hypertriglycerid(TG)emia, low HDL cholesterol(HDL-C)emia, hypertension, abdominal obesity and impaired glucose tolerance), hyperinsulinemia, perception disorder in hyperinsulinemia, tumor (e.g., leukemia, breast cancer, prostate cancer, skin cancer etc.), irritable bowel syndrome, acute or chronic diarrhea, inflammatory disease (e.g., arteriosclerosis (e.g., atherosclerosis etc.), rheumatoid arthritis, spondylitis deformans, osteoarthritis, lumbago, gout, hyperuricemia, postoperative or post-traumatic inflammation, swelling, neuralgia, pharyngolaryngitis, bladder inflammation, hepatitis (including nonalcoholic steatohepatitis), pneumonia, pancreatitis, inflammatory colitis, ulcerative colitis etc.), visceral fat syndrome, macular edema, dyslipidemia, sexual dysfunction, muscular atrophy, dermatic diseases, arthropathy, osteopenia, arteriosclerosis, thrombotic disease, dyspepsia, memory and learning disabilities, depression, manic-depressive illness, schizophrenia, Attention Deficit hyperactivity disorder, vision disorder, appetite regulation disorder (e.g., hyperorexia etc.), hypoglycemia, edema, insulin resistance, unstable diabetes, fatty atrophy, insulin allergy, insulinoma, lipotoxicity, cancer (e.g., breast cancer etc.), immune diseases (e.g., immunodeficiency etc.), multiple sclerosis, acute renal failure and the like. Here, diabetes includes type 1 diabetes, type 2 diabetes, gestational diabetes and obese diabetes. Dyslipidemia includes hypertriglyceridemia, hypercholesterolemia, hypo-HDL-emia, postprandial hyperlipemia and the like.

For diagnostic criteria of diabetes, Japan Diabetes Society reported new diagnostic criteria in 1999.

According to this report, diabetes is a condition showing any of a fasting blood glucose level (glucose concentration of intravenous plasma) of not less than 126 mg/dl, a 75 g oral glucose tolerance test (75 g OGTT) 2 h level (glucose concentration of intravenous plasma) of not less than 200 mg/dl, and a non-fasting blood glucose level (glucose concentration of intravenous plasma) of not less than 200 mg/dl. A condition not falling under the above-mentioned diabetes and different from "a condition showing a fasting blood glucose level (glucose concentration of intravenous plasma) of less than 110 mg/dl or a 75 g oral glucose tolerance test (75 g OGTT) 2 h level (glucose concentration of intravenous plasma) of less than 140 mg/dl" (normal type) is called a "borderline type".

In addition, ADA (American Diabetes Association) and WHO reported diagnostic criteria of diabetes.

According to these reports, diabetes is a condition showing a fasting blood glucose level (glucose concentration of intravenous plasma) of not less than 126 mg/dl, or a 75 g oral glucose tolerance test 2 h level (glucose concentration of intravenous plasma) of not less than 200 mg/dl.

According to the above-mentioned reports by ADA and WHO, impaired glucose tolerance is a condition showing a 75 g oral glucose tolerance test 2 h level (glucose concentration of intravenous plasma) of not less than 140 mg/dl and less than 200 mg/dl. According to the report of ADA, a condition showing a fasting blood glucose level (glucose concentration of intravenous plasma) of not less than 110 mg/dl and less than 126 mg/dl is called IFG (Impaired Fasting Glucose). According to the report of WHO, among the IFG (Impaired Fasting Glucose), a condition showing a 75 g oral glucose tolerance test 2 h level (glucose concentration of intravenous plasma) of not less than 110 mg/dl and less than 126 mg/dl is called IFG (Impaired Fasting Glycemia).

The compound of the present invention can also be used as an agent for the prophylaxis or treatment of diabetes, borderline type, abnormal glucose tolerance, IFG (Impaired Fasting Glucose) and IFG (Impaired Fasting Glycemia), as determined according to the above-mentioned diagnostic criteria. Moreover, the compound of the present invention can prevent progress of borderline type, abnormal glucose tolerance, IFG (Impaired Fasting Glucose) or IFG (Impaired Fasting Glycemia) into diabetes.

Since the compound of the present invention has a suppressive activity for adipocyte differentiation, it is useful as an agent for the prophylaxis or treatment of diseases developed by or whose development depends on promoted adipocyte differentiation or a factor induced by promoted adipocyte differentiation.

Examples of the disease developed by or whose development depends on promoted adipocyte differentiation or a factor induced by promoted adipocyte differentiation include obesity complications, sleep apnea syndrome, osteoporosis, cachexia (e.g., cancerous cachexia, tuberculous cachexia, diabetic cachexia, hemopathic cachexia, endocrinopathic cachexia, infectious cachexia or cachexia induced by acquired immunodeficiency syndrome etc.), fatty liver, hypertension, polycystic ovary syndrome, muscular dystrophy, sarcopenic obesity, cerebrovascular disorder (e.g., cerebral infarction, cerebral apoplexy etc.), metabolic syndrome (pathology involving not less than three selected from hypertriglycerid(TG)emia, low HDL cholesterol(HDL-C)emia, hypertension, abdominal obesity and impaired glucose tolerance), hyperinsulinemia, perception disorder in hyperinsulinemia, irritable bowel syndrome, acute or chronic diarrhea, swelling, neuralgia, hepatitis (including nonalcoholic steatohepatitis), cardiac disease (e.g., cardiac hypertrophy, acute cardiac failure and chronic cardiac failure including congestive cardiac failure, cardiomyopathy, angina pectoris, myocarditis, arrhythmia, tachycardia, myocardial infarction etc.), myocardial ischemia, venous insufficiency, transition to cardiac failure after myocardial infarction, hypertension, cor pulmonale, arteriosclerosis including atherosclerosis (e.g., aneurysm, coronary arteriosclerosis, cerebral arteriosclerosis, peripheral arteriosclerosis etc.), vascular hypertrophy, intervention (e.g., percutaneous transluminal coronary angioplasty, stenting, coronary angioscopy, intravascular ultrasound, intracoronary thrombolysis etc.) and vascular hypertrophy or obstruction and organ damage after heart transplantation, vascular reocclusion•restenosis after bypass surgery, respiratory diseases (e.g., cold syndrome, pneumonia, asthma, pulmonary hypertension, pulmonary thrombosis, pulmonary embolism etc.), bone disease (e.g., bone fracture, bone refracture, bone deformation, spondylosis deformans, osteosarcoma, myeloma, dysosteogenesis, nonmetabolic bone diseases such as lateral curvature and the like, bone defect, osteoporosis, osteomalacia, rickets, osteitis fibrosis, renal osteodystrophy, Paget's disease of bone, ankylosing spondylitis, rheumatoid arthritis, gonarthrosis and destruction of articular tissue in diseases similar thereto etc.), inflammatory disease (e.g., retinopathy, nephropathy, neuropathy, rheumatoid arthritis, osteoarthritis, rheumatoid spondylitis, arthritis such as periostitis and the like, postoperative or post-traumatic inflammation, relief of swelling, pharyngitis, bladder inflammation, atopic dermatitis, inflammatory bowel disease such as Crohn's disease, ulcerative colitis and the like, meningitis, inflammatory ocular disease, inflammatory pulmonary diseases such as pneumonia•silicosis•lung sarcoidosis•pulmonary tuberculosis and the like, etc.), allergic disease (e.g., allergic rhinitis, conjunctivitis, gastrointestinal allergy, pollinosis, anaphylaxis etc.), drug dependence, neurodegenerative disease (e.g., Alzheimer's disease, Parkinson's disease, amyotrophic lateral sclerosis, AIDS encephalopathy etc.), central nervous disorders (e.g., disorders such as cerebral hemorrhage and cerebral infarction and the like and sequelae•complications thereof, head trauma, spinal injury, brain edema etc.), dementia, memory disorders, disturbance of consciousness, amnesia, anxiety, tension symptom, anxious mental state, mental diseases (e.g., depression, epilepsy, alcohol dependence etc.), ischemic peripheral circulatory disorder, deep vein thrombosis, obstructive peripheral circulatory disorder, arteriosclerosis obliterans, thromboangiitis obliterans, diabetes (e.g., type 1 diabetes, type 2 diabetes, type 1.5 diabetes (LADA (Latent Autoimmune Diabetes in Adults)), gestational diabetes, impaired insulin secretion diabetes, obese diabetes, impaired glucose tolerance (IGT (Impaired Glucose Tolerance)), IFG (Impaired Fasting Glucose), IFG (Impaired Fasting Glycemia) etc.), diabetic complications [e.g., neuropathy, nephropathy, retinopathy, cataract, macroangiopathy, osteopenia, diabetic hyperosmolar coma, infections (e.g., respiratory infection, urinary tract infection, gastrointestinal infection, skin and soft tissue infections, foot infection etc.), diabetic gangrene, xerostomia, hypacusis, cerebrovascular disorder, peripheral circulatory failure etc.], urinary incontinence, disorder of metabolism and nutrition (e.g., obesity (e.g., malignant mastocytosis, exogenous obesity, hyperinsulinar obesity, hyperplasmic obesity, hypophyseal adiposity, hypoplasmic obesity, hypothyroid obesity, hypothalamic obesity, symptomatic obesity, infantile obesity, upper body obesity, alimentary obesity, hypogonadal obesity, systemic mastocytosis, simple obesity, central obesity etc.), hyperphagia etc.), hyperlipemia, hypercholesterolemia, impaired glucose tolerance etc.), insulin resistance syndrome, syndrome X, visceral fat syndrome, male or female sexual dysfunction, cerebrovascular disorder (e.g., asymptomatic cerebrovascular damage, transient cerebral ischemic attack, cerebral apoplexy, cerebrovascular dementia, hypertensive encephalopathy, cerebral infarction etc.), brain edema, brain circulation disorder, recurrence and sequelae of cerebrovascular disorder (e.g., neural symptoms, mental symptoms, subjective symptoms, activities of daily living impairment etc.), renal diseases (e.g., nephritis, glomerulonephritis, glomerulosclerosis, renal failure, thrombotic microangiopathy, diabetic nephropathy, nephrotic syndrome, hypertensive nephrosclerosis, dialysis complications, organ damage including nephropathy due to radiation etc.), ophthalmic diseases (e.g., glaucoma, ocular hypertension disease etc.), thrombosis, multiple organ failure, endothelial dysfunction, and other circulatory diseases (e.g., ischemic cerebral circulatory disorder, Raynaud's disease, Buerger's disease etc.), chronic obstructive pulmonary diseases, interstitial pneumonia, carinii pneumonia, collagen disease (e.g., systemic lupus erythematosus, scleroderma, polyarteritis etc.), liver disease (e.g., hepatitis including chronic one, cirrhosis etc.), digestive tract diseases (e.g., gastritis, gastric ulcer, gastric cancer, postgastrectomy disturbances, dyspepsia, esophageal ulcer, pancreatitis, colon polyp, cholelithiasis, hemorrhoids, variceal ruptures of esophagus or stomach etc.), blood and hematopoietic disease (e.g., polycythemia, vascular purpura, autoimmune hemolytic anemia, disseminated intravascular coagulation syndrome, multiple myelosis etc.), solid tumor, tumor (e.g., malignant melanoma, malignant lymphoma, gastrointestinal (e.g., stomach, intestine etc.) cancer etc.), cancer and cachexia associated therewith, cancer metastasis, endocrine diseases (e.g., Addison's disease, Cushing's syndrome, melanocytoma, primary aldosteronism etc.), urinary organs and male genital disease (e.g., bladder inflammation, prostate hypertrophy, prostate cancer, sexually-transmitted diseases etc.), gynecological diseases (e.g., climacteric disorder, gestational toxicosis, endometriosis, hysteromyoma, ovarian disease, mammary gland disease, sexually-transmitted diseases etc.), infections (e.g., virus infections such as cytomegalovirus, influenza virus, herpes virus and the like, rickettsial infections, bacterial infections etc.), toxemia (e.g., sepsis, septic shock, endotoxin shock, gram negative sepsis, toxic shock syndrome etc.), dermatic diseases (e.g., keloid, hemangioma, psoriasis etc.) and the like. The compound of the present invention is desirably used particularly for the prophylaxis or treatment of diabetes, obesity, dyslipidemia and the like.

Furthermore, since the compound of the present invention has an action to suppress NF-kB activation, it is useful as an agent for the prophylaxis or treatment of diseases developed by or whose development is promoted by NF-kB activation or a factor induced by NF-kB activation.

Examples of diseases developed by or whose development is promoted by NF-kB activation or a factor induced by NF-kB activation include various inflammatory diseases. Examples of such inflammatory disease include arthritis (e.g., rheumatoid arthritis, spondylitis deformans, osteoarthritis, lumbago, rheumatoid spondylitis, gouty arthritis, synovitis etc.), asthma, pharyngolaryngitis, bladder inflammation, hepatitis, pneumonia, allergic disease, arteriosclerosis including atherosclerosis (e.g., aneurysm, coronary arteriosclerosis, cerebral arteriosclerosis, peripheral arteriosclerosis etc.), gastric mucosal injury (including gastric mucosal injury caused by aspirin), digestive tract diseases such as inflammatory bowel disease and the like (e.g., Crohn's disease, ulcerative colitis etc.), diabetic complications (e.g., retinopathy, nephropathy, diabetic neuropathy, diabetic vascular disorder etc.), atopic dermatitis, chronic obstructive pulmonary diseases, systemic lupus erythematosus, visceral inflammatory disease (e.g., nephritis, hepatitis, nonalcoholic steatohepatitis etc.), autoimmune hemolytic anemia, psoriasis, neurodegenerative disease (e.g., Alzheimer's disease, Parkinson's disease, amyotrophic lateral sclerosis, AIDS encephalopathy etc.), central nervous disorders (e.g., cerebrovascular disorder such as cerebral hemorrhage and cerebral infarction and the like, head trauma, spinal damage, brain edema, multiple sclerosis etc.), meningitis, myocarditis, cardiomyopathy, ischemic cardiac diseases, angina pectoris, myocardial infarction, congestive cardiac failure, vascular hypertrophy or obstruction and organ damage after intervention (e.g., percutaneous transluminal coronary angioplasty, stenting, coronary angioscopy, intravascular ultrasound, intracoronary thrombolysis etc.), reocclusion•restenosis after bypass operation, endothelial functional disorder, other circulatory diseases (e.g., intermittent claudication, obstructive peripheral circulatory disorder, arteriosclerosis obliterans, thromboangiitis obliterans, ischemic cerebral circulatory disorder, Raynaud's disease, Buerger's disease etc.), inflammatory ocular disease, pulmonary sarcoidosis (e.g., chronic pneumonia, silicosis, lung sarcoidosis, pulmonary tuberculosis etc.), endometriosis, toxemia (e.g., sepsis, septic shock, endotoxin shock, gram negative sepsis, toxin shock syndrome etc.), cachexia (e.g., cachexia due to infection, cancerous cachexia, cachexia induced by acquired immunodeficiency syndrome etc.), cancer, Addison's disease, Creutzfeldt-Jakob disease, virus infection (e.g., virus infection etc. such as cytomegalovirus, influenza virus, herpes virus and the like), disseminated intravascular coagulation and the like.

Since the compound of the present invention has a suppressive activity for inhibiting body weight gain, it can be used as a body weight gain suppressor to mammals. Target mammals may be any mammals of which body weight gain is to be avoided. The mammals may have a risk of body weight gain genetically or may be suffering from lifestyle-related diseases such as diabetes, hypertension and/or hyperlipemia and the like. The body weight gain may be caused by excessive feeding or diet without nutrient balance, or may be derived from concomitant drug (e.g., insulin sensitizers having PPARγ-agonistic-like activity such as troglitazone, rosiglitazone, englitazone, ciglitazone, pioglitazone and the like). In addition, body weight gain may be preliminary to obesity, or may be body weight gain of obesity patients. Here, obesity is defined that BMI (body mass index; body weight (kg)/[height (m)]$^2$) is not less than 25 for Japanese (criterion by Japan Society for the Study of Obesity), or not less than 30 for westerner (criterion by WHO).

The compound of the present invention is also useful as an agent for the prophylaxis or treatment of metabolic syndrome. Because patients with metabolic syndrome have an extreme high incidence of cardiovascular diseases as compared to patients with single lifestyle-related disease, the prophylaxis or treatment of metabolic syndrome is quite important to prevent cardiovascular diseases.

Criteria for diagnosis of metabolic syndrome are announced by WHO in 1999, and by NCEP in 2001. According to the criterion of WHO, patients with at least two of abdominal obesity, dyslipidemia (high TG or low HDL) and hypertension in addition to hyperinsulinemia or impaired glucose tolerance are diagnosed as metabolic syndrome (World Health Organization: Definition, Diagnosis and Classification of Diabetes Mellitus and Its Complications. Part I: Diagnosis and Classification of Diabetes Mellitus, World Health Organization, Geneva, 1999). According to the criterion of Adult Treatment Panel III of National Cholesterol Education Program, that is an indicator for managing ischemic heart diseases in America, patients with at least three of abdominal obesity, high triglycerides, low HDL cholesterol, hypertension and impaired glucose tolerance are diagnosed as metabolic syndrome (National Cholesterol Education Program: Executive Summary of the Third Report of National Cholesterol Education Program (NCEP) Expert Panel on Detection, Evaluation, and Treatment of High Blood Cholesterol in Adults (Adults Treatment Panel III). The Journal of the American Medical Association, Vol. 285, 2486-2497, 2001).

The dose of the compound of the present invention can be appropriately selected according to the subject of administration, administration route, target disease, symptom and the like. For example, the dose of the compound of the present invention for oral administration to an adult patient with diabetes, obesity, dyslipidemia, steatohepatitis, cachexia, or muscular atrophy is generally about 0.001-50 mg/kg body weight, preferably about 0.01-45 mg/kg body weight, more preferably about 0.1-2 mg/kg, as a single dose of the active ingredient "compound (I)". This amount is desirably administered 1-3 times per day.

Moreover, the compound of the present invention can be used in combination with a drug other than the compound of the present invention.

Examples of the drug that can be used in combination with the compound of the present invention (hereinafter sometimes to be abbreviated as concomitant drug) include another therapeutic agents for diabetes, a therapeutic agent for diabetic complications, a therapeutic agent for hyperlipemia, an antihypertensive agent, an antiobestic agent, a diuretic, a chemotherapeutic agent, an immunotherapeutic agent, an anti-inflammatory agent, an antithrombotic agent, a therapeutic agent for osteoporosis, a vitamin drug, an antidementia agent, a therapeutic agent for pollakiuria or urinary incontinence, a therapeutic agent for dysuria and the like.

A concomitant drug for the compound of the present invention specifically includes the following.

Examples of another therapeutic agents for diabetes include insulin preparations (e.g., animal insulin preparations extracted from pancreas of bovine or swine; human insulin preparations genetically synthesized using *Escherichia coli*, yeast; insulin zinc; protamine zinc insulin; fragment or derivative of insulin (e.g., INS-1), oral insulin preparation etc.), insulin sensitizers (e.g., pioglitazone or a salt thereof (preferably hydrochloride), rosiglitazone or a salt thereof (preferably maleate), Metaglidasen, AMG-131, Balaglitazone, MBX-2044, Rivoglitazone, Aleglitazar, Chiglitazar, Lobeglitazone, PLX-204, PN-2034, GFT-505, THR-0921, compound described in WO 2007/013694, WO 2007/018314, WO 2008/093639 or WO 2008/099794, etc.), α-glucosidase inhibitors (e.g., voglibose, acarbose, miglitol, emiglitate etc.), biguanides (e.g., metformin, buformin or a salt thereof (e.g., hydrochloride, fumarate, succinate etc.) etc.), insulin secretagogues [sulfonylureas (e.g., tolbutamide, glibenclamide, gliclazide, chlorpropamide, tolazamide, acetohexamide, glyclopyramide, glimepiride, glipizide, glybuzole etc.), repaglinide, nateglinide, mitiglinide or a calcium salt hydrate thereof etc.], dipeptidyl peptidase IV inhibitors (e.g., Alogliptin or a salt thereof (preferably benzoate), Vildagliptin, Sitagliptin, Saxagliptin, BI1356, GRC8200, MP-513, PF-00734200, PHX1149, SK-0403, ALS2-0426, TA-6666, TS-021, KRP-104, 2-[[6-[(3R)-3-amino-1-piperidyl]-3,4-dihydro-3-methyl-2,4-dioxo-1(2H)-pyrimidinyl]methyl]-4-fluorobenzonitrile or a salt thereof etc.), β3 agonists (e.g., N-5984 etc.), GPR40 agonists (e.g., compound described in WO 2004/041266, WO 2004/106276, WO 2005/063729, WO 2005/063725, WO 2005/087710, WO 2005/095338, WO 2007/013689 or WO 2008/001931, etc.), GLP-1 receptor agonists [e.g., GLP-1, GLP-1MR preparation, Liraglutide, Exenatide, AVE-0010, BIM-51077, Aib(8,35)hGLP-1(7,37) NH$_2$, CJC-1131, Albiglutide etc.], amylin agonists (e.g., pramlintide etc.), phosphotyrosine phosphatase inhibitors (e.g., sodium vanadate etc.), gluconeogenesis inhibitors (e.g., glycogen phosphorylase inhibitors, glucose-6-phosphatase inhibitors, glucagon antagonists, FBPase inhibitors etc.), SGLT2 (sodium-glucose cotransporter 2) inhibitors (e.g., Depagliflozin, AVE2268, TS-033, YM543, TA-7284, Remogliflozin, ASP1941 etc.), SGLT1 inhibitors, 11β-hydroxysteroid dehydrogenase inhibitors (e.g., BVT-3498, INCB-13739 etc.), adiponectin or an agonist thereof, IKK inhibitors (e.g., AS-2868 etc.), leptin resistance improving drugs, somatostatin receptor agonists, glucokinase activators (e.g., Piragliatin, AZD1656, AZD6370, TTP-355, compound described in WO 2006/112549, WO 2007/028135, WO 2008/047821, WO 2008/050821, WO 2008/136428 or WO 2008/156757, etc.), GIP (Glucose-dependent insulinotropic peptide), GPR119 agonists (e.g., PSN821, MBX-2982, APD597 etc.), FGF21, FGF analogs and the like.

Examples of the therapeutic agents for diabetic complications include aldose reductase inhibitors (e.g., tolrestat, epalrestat, zopolrestat, fidarestat, CT-112, ranirestat (AS-3201), lidorestat etc.), neurotrophic factor and increasing drugs thereof (e.g., NGF, NT-3, BDNF, neurotrophin production/secretion promoters (e.g., 4-(4-chlorophenyl)-2-(2-methyl-1-imidazolyl)-5-[3-(2-methylphenoxy)propyl]oxazole etc.) described in WO 01/14372, a compound described in WO 2004/039365, etc.), PKC inhibitors (e.g., ruboxistaurin mesylate etc.), AGE inhibitors (e.g., ALT946, N-phenacylthiazolium bromide (ALT766), EXO-226, Pyridorin, pyridoxamine etc.), GABA receptor agonists (e.g., gabapentine, Pregabalin etc.), serotonin and noradrenaline reuptake inhibitors (e.g., duloxetine etc.), sodium channel inhibitors (e.g., lacosamide etc.), reactive oxygen scavengers (e.g., thioctic acid etc.), cerebral vasodilators (e.g., tiapride, mexiletine etc.), somatostatin receptor agonists (e.g., BIM23190 etc.), apoptosis signal-regulating kinase-1 (ASK-1) inhibitors and the like.

Examples of the therapeutic agent for hyperlipemia include HMG-CoA reductase inhibitors (e.g., pravastatin, simvastatin, lovastatin, atorvastatin, fluvastatin, rosuvastatin, pitavastatin or a salt thereof (e.g., sodium salt, calcium salt etc.) etc.), squalene synthase inhibitors (e.g., a compound described in WO 97/10224, for example, N-[[(3R,5S)-1-(3-acetoxy-2,2-dimethylpropyl)-7-chloro-5-(2,3-dimethoxyphenyl)-2-oxo-1,2,3,5-tetrahydro-4,1-benzoxazepin-3-yl] acetyl]piperidine-4-acetic acid etc.), fibrate compounds (e.g., bezafibrate, clofibrate, simfibrate, clinofibrate etc.), anion exchange resins (e.g., cholestyramine etc.), probucol, nicotinic acid drugs (e.g., nicomol, niceritrol, niaspan etc.), ethyl icosapentate, phytosterols (e.g., soysterol, γ-oryzanol etc.), cholesterol absorption inhibitors (e.g., zachia etc.), CETP inhibitors (e.g., dalcetrapib, anacetrapib etc.), ω-3 fatty acid preparations (e.g., ω-3-acid ethyl esters 90 etc.) and the like.

Examples of the antihypertensive agent include angiotensin converting enzyme inhibitors (e.g., captopril, enalapril, delapril etc.), angiotensin II antagonists (e.g., candesartan cilexetil, candesartan, losartan, losartan potassium, eprosartan, valsartan, telmisartan, irbesartan, tasosartan, olmesartan, olmesartan medoxomil, azilsartan, azilsartan medoxomil etc.), calcium antagonists (e.g., manidipine, nifedipine, amlodipine, efonidipine, nicardipine, cilnidipine and the like), β (e.g., metoprolol, atenolol, propranolol, carvedilol, pindolol etc.), clonidine and the like.

Examples of the anti-obestic agent include monoamine uptake inhibitors (e.g., phentermine, sibutramine, mazindol, fluoxetine, tesofensine etc.), serotonin 2C receptor agonists (e.g., lorcaserin etc.), serotonin 6 receptor antagonists, histamine H3 receptor modulators, GABA modulators (e.g., topiramate etc.), neuropeptide Y antagonists (e.g., velneperit etc.), cannabinoid receptor antagonists (e.g., rimonabant, taranabant etc.), ghrelin antagonists, ghrelin receptor antagonists, ghrelin O-acyltransferase inhibitors, opioid receptor antagonists (e.g., GSK-1521498 etc.), orexin receptor antagonists, melanocortin 4 receptor agonists, 11β-hydroxysteroid dehydrogenase inhibitors (e.g., AZD-4017 etc.), pancreatic lipase inhibitors (e.g., orlistat, cetilistat etc.), β3 agonists (e.g., N-5984 etc.), diacylglycerol acyltransferase 1 (DGAT1) inhibitors, acetyl-CoA carboxylase (ACC) inhibitors, stearoyl-CoA desaturated enzyme inhibitors, microsomal triglyceride transfer protein inhibitors (e.g., R-256918 etc.), sodium-glucose cotransporter inhibitors (e.g., JNJ-28431754, remogliflozin etc.), NFκ inhibitors (e.g., HE-3286 etc.), PPAR agonists (e.g., GFT-505, DRF-11605 etc.), phosphotyrosine phosphatase inhibitors (e.g., sodium vanadate, Trodusquemine etc.), GPR119 agonists (e.g., PSN-821 etc.), glucokinase activators (e.g., AZD-1656 etc.), leptin, leptin derivatives (e.g., metreleptin etc.), CNTF (ciliary neurotrophic factor), BDNF (brain-derived neurotrophic factor), cholecystokinin agonists, glucagon-like peptide-1 (GLP-1) preparations (e.g., animal GLP-1 preparations extracted from the pancreas of bovine and pig; human GLP-1 preparations genetically synthesized using Escherichia coli or yeast; fragments or derivatives of GLP-1 (e.g., exenatide, liraglutide etc.) etc.), amylin preparations (e.g., pramlintide, AC-2307 etc.), neuropeptide Y agonists (e.g., PYY3-36, derivatives of PYY3-36, obinepitide, TM-30339, TM-30335 etc.), oxyntomodulin preparations: FGF21 preparations (e.g., animal FGF21 preparations extracted from the pancreas of bovine and pig; human FGF21 preparations genetically synthesized using Escherichia coli or yeast; fragments or derivatives of FGF21 etc.), anorexigenic agents (e.g., P-57 etc.) and the like.

Examples of the diuretics include xanthine derivatives (e.g., theobromine sodium salicylate, theobromine calcium salicylate etc.), thiazide preparations (e.g., ethiazide, cyclopenthiazide, trichlormethiazide, hydrochlorothiazide, hydroflumethiazide, benzylhydrochlorothiazide, penflutizide, polythiazide, methyclothiazide etc.), antialdosterone preparations (e.g., spironolactone, triamterene etc.), carbonic anhydrase inhibitors (e.g., acetazolamide etc.), chlorobenzenesulfonamide preparations (e.g., chlorthalidone, mefruside, indapamide etc.), azosemide, isosorbide, ethacrynic acid, piretanide, bumetanide, furosemide and the like.

Examples of the chemotherapeutic agents include alkylating agents (e.g., cyclophosphamide, ifosfamide etc.), metabolic antagonists (e.g., methotrexate, 5-fluorouracil etc.), antitumor antibiotics (e.g., mitomycin, adriamycin etc.), plant-derived antitumor agents (e.g., vincristine, vindesine, Taxol etc.), cisplatin, carboplatin, etoposide and the like. Of these, Furtulon or NeoFurtulon, which are 5-fluorouracil derivatives, and the like are preferable.

Examples of the immunotherapeutic agents include microorganism or bacterial components (e.g., muramyl dipeptide derivatives, Picibanil etc.), polysaccharides having immunostimulating activity (e.g., lentinan, schizophyllan, krestin etc.), cytokines obtained by genetic engineering techniques (e.g., interferon, interleukin (IL) etc.), colony stimulating factors (e.g., granulocyte colony stimulating factor, erythropoietin etc.) and the like, with preference given to interleukins such as IL-1, IL-2, IL-12 and the like.

Examples of the anti-inflammatory agent include non-steroidal anti-inflammatory drugs such as aspirin, acetaminophen, indomethacin and the like, and the like.

Examples of the antithrombotic agent include heparins (e.g., heparin sodium, heparin calcium, enoxaparin sodium, dalteparin sodium etc.), warfarins (e.g., warfarin potassium etc.), antithrombin drugs (e.g., argatroban, dabigatran etc.), FXa inhibitors (e.g., rivaroxaban, apixaban, edoxaban, YM150, compound described in WO 02/06234, WO 2004/048363, WO 2005/030740, WO 2005/058823 or WO 2005/113504, etc.) and the like, thrombolytic agents (e.g., urokinase, tisokinase, alteplase, nateplase, monteplase, pamiteplase etc.), antiplatelet aggregation drugs (e.g., ticlopidine hydrochloride, clopidogrel, prasugrel, E5555, SHC530348, cilostazol, ethyl icosapentate, beraprost sodium, sarpogrelate hydrochloride etc.) and the like.

Examples of the therapeutic agents for osteoporosis include alfacalcidol, calcitriol, elcatonin, calcitonin salmon, estriol, ipriflavone, pamidronate disodium, alendronate sodium hydrate, incadronate disodium, risedronate disodium and the like.

Examples of the vitamin drugs include vitamin $B_1$, vitamin $B_{12}$ and the like.

Examples of the antidementia agents include tacrine, donepezil, rivastigmine, galanthamine and the like.

Examples of the therapeutic agents for pollakiuria or urinary incontinence include flavoxate hydrochloride, oxybutynin hydrochloride, propiverine hydrochloride and the like.

Examples of the therapeutic agents for dysuria include acetylcholine esterase inhibitors (e.g., distigmine etc.) and the like.

Furthermore, drugs having a cachexia-improving action established in animal models and clinical use, such as cyclooxygenase inhibitors (e.g., indomethacin etc.), progesterone derivatives (e.g., megestrol acetate etc.), glucosteroids (e.g., dexamethasone etc.), metoclopramide agents, tetrahydrocannabinol agents, fat metabolism improving agents (e.g., eicosapentanoic acid etc.), growth hormones, IGF-1, or antibodies to a cachexia-inducing factor such as TNF-α, LIF, IL-6, oncostatin M and the like, can be used in combination with the compound of the present invention.

Furthermore, glycosylation inhibitors (e.g., ALT-711 etc.), nerve regeneration promoters (e.g., Y-128, VX853, prosaptide etc.), antidepressant (e.g., desipramine, amitriptyline, imipramine etc.), antiepileptic drugs (e.g., lamotrigine, Trileptal, Keppra, Zonegran, Pregabalin, Harkoseride, carbamazepine etc.), antiarrhythmic agents (e.g., mexiletine etc.), acetylcholine receptor ligand (e.g., ABT-594 etc.), endothelin receptor antagonist (e.g., ABT-627 etc.), monoamine uptake inhibitors (e.g., tramadol etc.), narcotic analgesics (e.g., morphine etc.), GABA receptor agonists (e.g., gabapentin, gabapentin MR agent etc.), α2 receptor agonist (e.g., clonidine etc.), topical analgesic (e.g., capsaicin etc.), antianxiety drug (e.g., benzothiazepine etc.), phosphodiesterase inhibitor (e.g., sildenafil etc.), dopamine receptor agonist (e.g., apomorphine etc.), midazolam, ketoconazole and the like can also be used in combination with the compound of the present invention.

The administration time of the compound of the present invention and the concomitant drug is not restricted, and these can be administered to an administration subject simultaneously, or may be administered in a staggered manner.

The administration mode is not particularly limited, and the compound of the present invention and the concomitant drug only need to be combined.

Examples of such administration mode include the following:
(1) administration of a single preparation obtained by simultaneously processing the compound of the present invention and the concomitant drug,
(2) simultaneous administration of two kinds of preparations of the compound of the present invention and the concomitant drug, which have been separately produced, by the same administration route,
(3) administration of two kinds of preparations of the compound of the present invention and the concomitant drug, which have been separately produced, by the same administration route in a staggered manner,
(4) simultaneous administration of two kinds of preparations of the compound of the present invention and the concomitant drug, which have been separately produced, by different administration routes,
(5) administration of two kinds of preparations of the compound of the present invention and the concomitant drug, which have been separately produced, by different administration routes in a staggered manner (e.g., administration in the order of the compound of the present invention and the concomitant drug, or in the reverse order) and the like.

The dose of the concomitant drug can be determined as appropriate based on the dose clinically employed. The proportion of the compound of the present invention and the concomitant drug can be appropriately determined depending on the administration subject, administration route, target disease, condition, combination and the like. When, for example, the administration subject is human, the concomitant drug is used in an amount of 0.01-100 parts by weight per 1 part by weight of the compound of the present invention.

By combining the compound of the present invention and a concomitant drug, a superior effect such as
(1) the dose can be reduced as compared to single administration of the compound of the present invention or a concomitant drug,
(2) the period of treatment can be set longer by selecting a concomitant drug having different action and mechanism from the compound of the present invention,
(3) a sustained treatment effect can be designed by selecting a concomitant drug having different action and mechanism from the compound of the present invention,
(4) a synergistic effect can be afforded by a combined use of the compound of the present invention and a concomitant drug, and the like, can be achieved.

EXAMPLES

The present invention is explained in more detail by referring to the following Examples, Experimental Examples and Formulation Examples, which do not limit the present invention and may be changed as long as they do not deviate from the scope of the present invention.

In the following Examples, the "room temperature" generally shows about 10° C. to about 35° C.

The solvent used for chromatography is in % by volume, and others are in wt %.

In proton NMR spectrum, peaks that cannot be confirmed by broad such as OH, NH proton and the like are not described in the data.

SD means standard deviation.

Other abbreviations used herein mean the following.
s: singlet
d: doublet
t: triplet
q: quartet
m: multiplet
br: broad
J: coupling constant
Hz: hertz
$CDCl_3$: deuterated chloroform
DMSO-$d_6$: deuterated dimethyl sulfoxide
$^1$H NMR: proton nuclear magnetic resonance In the following Examples, the melting point, nuclear magnetic resonance spectrum (NMR) and mass spectrum (MS) were measured under the following conditions.

melting point instrument: Yanaco micro melting point apparatus, or Buchi melting point apparatus B-545 type.
NMR instrument: Varian, Varian Gemini 300 (300 MHz), Bruker Bio Spin AVANCE 300.
MS instrument: Waters ZQ2000, column: SHISEIDO CAPCELLPAK C18 UG120 1.5 mm I.D.×35 mm S-3 μm, solvent: solution A 0.05% trifluoroacetic acid-containing water, solution B 0.04% trifluoroacetic acid-containing acetonitrile, gradient cycle: 0.00 min (solution A/solution B=90/10), 0.01 min (solution A/solution B=90/10), 2.00 min (solution A/solution B=5/95), 2.75 min (solution A/solution B=5/95), 2.76 min (solution A/solution B=90/10), 3.45 min (solution A/solution B=90/10), flow rate: 0.5 mL/min, detection method: UV 220 nm, ionization method: ESI positive. Alternatively, MS instrument: Agilent G6100, column: ZORBAX Extend-C18 Rapid Resolution HT 3.0×30 mm 1.8 micron 600 bar, solvent: solution A 0.01 M ammonium acetate-containing water, solution B 0.01 M ammonium acetate-containing acetonitrile, gradient cycle: 0.00 min (solution A/solution B=90/10), 0.20 min (solution A/solution B=90/10), 1.50 min (solution A/solution B=0/100), 2.00 min (solution A/solution B=90/10), flow rate: 1.2 mL/min, detection method: UV 220 nm, ionization method: ESI positive or ESI negative. The data described show actual data. Generally, a molecular ion peak is observed; however, when the compound has a tert-butoxycarbonyl group (-Boc), a peak after dissociation of tert-butoxycarbonyl group or tert-butyl group may also be observed as a fragment ion. When the compound has a hydroxyl group (—OH), a peak after dissociation of $H_2O$ may also be observed as a fragment ion. In the case of a salt, generally, a molecular ion peak or fragment ion peak of a free form is observed.

Purification by preparative HPLC in the Examples was performed under the following conditions.
instrument: Waters preparative HPLC system, column: SunFire Prep C18 OBD5 μm 30×50 mm Column, solvent:

solution A 0.1% trifluoroacetic acid-containing water, solution B 0.1% trifluoroacetic acid-containing acetonitrile, gradient cycle: 0.00 min (solution A/solution B=90/10), 1.20 min (solution A/solution B=90/10), 5.20 min (solution A/solution B=0/100), 7.00 min (solution A/solution B=0/100), 7.01 min (solution A/solution B=90/10), 8.50 min (solution A/solution B=90/10), flow rate: 70 mL/min, detection method: UV 220 nm. Alternatively, instrument: Waters preparative HPLC system, column: YMC CombiPrep ODS-A (50×20 mm. I.D S-5 µm, 12 nm), solvent: solution A 0.1% trifluoroacetic acid-containing water, solution B 0.1% trifluoroacetic acid-containing acetonitrile, gradient cycle: 0.00 min (solution A/solution B=90/10), 0.20 min (solution A/solution B=90/10), 4.20 min (solution A/solution B=0/100), 6.30 min (solution A/solution B=0/100), 6.31 min (solution A/solution B=90/10), flow rate: 25 mL/min, detection method: UV 220 nm.

Example 1

(2E)-3-[4-(4-fluorophenyl)pyridin-3-yl]-N-{4-[2-(1,3,4-oxadiazol-2-yl)ethyl]phenyl}prop-2-enamide A) 4-(4-fluorophenyl)pyridine-3-carbaldehyde A mixture of 4-chloropyridine-3-carbaldehyde (33.44 g), (4-fluorophenyl)boronic acid (39.1 g), tetrakis(triphenylphosphine)palladium (6.73 g), 2 M aqueous potassium carbonate solution (314.4 mL) and 1,2-dimethoxyethane (500 mL) was heated under reflux for 6 hr. The reaction mixture was allowed to be cooled to room temperature, water was added thereof, and the mixture was extracted with ethyl acetate. The extract was dried over anhydrous magnesium sulfate, and the solvent was evaporated under reduced pressure. The residue was purified by silica gel column chromatography (hexane/ethyl acetate) to give the title compound (28.04 g).

$^1$H NMR (500 MHz, CDCl$_3$) δ 7.24 (2H, m), 7.37 (1H, d, J=5.5 Hz), 7.40 (2H, m), 8.82 (1H, d, J=5.5 Hz), 9.16 (1H, s), 10.08 (1H, s).

B) (2E)-3-[4-(4-fluorophenyl)pyridin-3-yl]prop-2-enoic acid

To a solution of sodium hydride (55% in oil, 16.23 g) in dry tetrahydrofuran (1 L) was slowly added triethyl phosphonoacetate (83.39 g) while maintaining the mixture at 15° C. or lower, and the mixture was stirred for 1 hr. To the reaction mixture was slowly added a solution of 4-(4-fluorophenyl)pyridine-3-carbaldehyde (57.57 g) in dry tetrahydrofuran (500 mL) while maintaining the mixture at 0° C. or lower, and the mixture was stirred at room temperature for 18 hr. To the reaction mixture was added saturated aqueous ammonium chloride solution, and the mixture was extracted with ethyl acetate. The extract was dried over anhydrous magnesium sulfate. The solvent was evaporated under reduced pressure to give a yellow solid (91.6 g). The pH of the aqueous layer after extraction was adjusted to 4-5 with 1 M hydrochloric acid, and the precipitated solid was collected by filtration, washed with water and a small amount of ethyl acetate, and dried to give the title compound as a crude solid (5.79 g).

The above-mentioned yellow solid (91.6 g) was suspended in concentrated hydrochloric acid (1.3 L), and the suspension was heated under reflux for 6 hr. The reaction mixture was cooled to 10° C. or lower, and the pH of the reaction mixture was adjusted to 4-5 with 48% aqueous sodium hydroxide solution. The precipitated solid was collected by filtration, washed with water and dried to give the title compound as a crude solid (62.33 g). It was combined with the crude solid (5.79 g) of the above-mentioned title compound, and the solid was recrystallized with ethanol to give the title compound (43.65 g).

$^1$H NMR (500 MHz, DMSO-d$_6$) δ 6.64 (1H, d, J=16.0 Hz), 7.43 (6H, m), 8.63 (1H, d, J=5.5 Hz), 9.04 (1H, s), 12.57 (1H, brs).

C) (2E)-3-[4-(4-fluorophenyl)pyridin-3-yl]-N-{4-[2-(1,3,4-oxadiazol-2-yl)ethyl]phenyl}prop-2-enamide A mixture of (2E)-3-[4-(4-fluorophenyl)pyridin-3-yl]prop-2-enoic acid (18.0 g), 4-[2-(1,3,4-oxadiazol-2-yl)ethyl]aniline (14.0 g), triethylamine (14.97 g), bis(2-oxo-3-oxazolidinyl)phosphinic chloride (18.84 g) and dichloromethane (2.5 L) was stirred at room temperature for 17 hr. The reaction mixture was washed successively with water and 1 M aqueous sodium hydroxide solution. Methanol (600 mL) was added thereof, and the mixture was dried over anhydrous magnesium sulfate. The solvent was evaporated under reduced pressure to give a solid. The obtained solid was recrystallized with ethanol to give the title compound (25.0 g).

$^1$H NMR (500 MHz, DMSO-d$_6$) δ 3.00 (2H, t, J=7.5 Hz), 3.18 (2H, t, J=15.5 Hz), 6.89 (1H, d, J=15.5 Hz), 7.19 (2H, d, J=8.5 Hz), 7.44 (6H, m), 7.57 (2H, d, J=8.5 Hz), 8.63 (1H, d, J=5.0 Hz), 8.92 (1H, s), 9.12 (1H, s), 10.24 (1H, brs).

Example 2

(2E)-3-[4-(4-methoxyphenyl)pyridin-3-yl]-N-{4-[2-(1,3,4-oxadiazol-2-yl)ethyl]phenyl}prop-2-enamide A) ethyl (2E)-3-[4-(4-methoxyphenyl)pyridin-3-yl]prop-2-enoate To a mixture of sodium hydride (60% in oil, 0.71 g) and dry tetrahydrofuran (25 mL) was slowly added triethyl phosphonoacetate (3.63 g) under ice-cooling, and the mixture was stirred until completion of the generation of hydrogen gas. To the reaction mixture was slowly added a solution of 4-(4-methoxyphenyl)pyridine-3-carbaldehyde (2.88 g) in dry tetrahydrofuran (5 mL) under ice-cooling, and the mixture was stirred for 1 hr. To the reaction mixture was added water, and the mixture was extracted with ethyl acetate. The extract was washed with saturated brine, and dried over anhydrous magnesium sulfate. The solvent was evaporated under reduced pressure. The residue was purified by silica gel column chromatography (NH, ethyl acetate) to give the title compound (2.85 g).

MS (ESI+): [M+H]$^+$284.2

B) (2E)-3-[4-(4-methoxyphenyl)pyridin-3-yl]prop-2-enoic acid

A mixture of ethyl (2E)-3-[4-(4-methoxyphenyl)pyridin-3-yl]prop-2-enoate (2.75 g), 2M aqueous sodium hydroxide solution (7.3 mL), tetrahydrofuran (15 mL) and methanol (15 mL) was stirred at room temperature for 5 hr. To the reaction mixture was added water. The solvent was evaporated under reduced pressure, and the pH of the residue was adjusted to 5-6 with 10% aqueous citric acid solution. The precipitated solid was collected by filtration, washed with water and dried. The obtained solid was suspended in hot ethanol, and the suspension was stirred, and slowly cooled to room temperature. The suspension was filtered, and the obtained solid was washed with ethanol, and dried to give the title compound (2.12 g).

MS (ESI+): [M+H]$^+$256.2

C) (2E)-3-[4-(4-methoxyphenyl)pyridin-3-yl]-N-{4-[2-(1,3,4-oxadiazol-2-yl)ethyl]phenyl}prop-2-enamide To a mixture (2E)-3-[4-(4-methoxyphenyl)pyridin-3-yl] prop-2-enoic acid (0.30 g), oxalyl chloride (0.12 mL) and dry tetrahydrofuran (10 mL) was added N,N-dimethylformamide (2 drops) under ice-cooling, and the mixture was stirred at room temperature for 30 min. The solvent was evaporated under reduced pressure. The residue was added to a solution of 4-[2-(1,3,4-oxadiazol-2-yl)ethyl]aniline (0.25 g) in N,N-dimethylacetamide (10 mL) under ice-cooling. The reaction mixture was stirred at room temperature for 1 hr, water was added thereof, and the mixture was neutralized with saturated aqueous sodium hydrogen carbonate solution. The precipitated solid was collected by filtration, washed with water and dried. The obtained solid was recrystallized from ethanol to give the title compound (0.37 g).

$^1$H NMR (300 MHz, CDCl$_3$) δ 3.08-3.23 (4H, m), 3.86 (3H, s), 6.68 (1H, d, J=15.5 Hz), 6.98-7.03 (2H, m), 7.15-7.21 (2H, m), 7.28-7.34 (3H, m), 7.60 (2H, d, J=8.1 Hz), 7.81 (1H, d, J=15.5 Hz), 8.34 (1H, s), 8.41 (1H, brs), 8.59 (1H, d, J=5.1 Hz), 8.91 (1H, s).

Example 3

(2E)-3-[4-(4-fluorophenyl)pyridin-3-yl]-N-{4-[2-(5-methyl-1,3,4-oxadiazol-2-yl)ethyl]phenyl}prop-2-enamide

A) 2-methyl-5-[(E)-2-(4-nitrophenyl)ethenyl]-1,3,4-oxadiazole

To a mixture of (2E)-3-(4-nitrophenyl)prop-2-enoic acid (5.46 g), N-methylmorpholine (3.404 g) and tetrahydrofuran (100 mL) was added dropwise isobutyl chloroformate (4.72 mL) at 0° C., and the mixture was stirred at the same temperature for 30 min. The reaction mixture was filtered, and the filtrate was added dropwise to a mixture of hydrazine monohydrate (6.478 g) and tetrahydrofuran (100 mL) at 0° C. The mixture was stirred at 0° C. for 2 hr, saturated aqueous ammonium chloride solution (100 mL) was added thereof, and the mixture was extracted with ethyl acetate. The extract was concentrated under reduced pressure. The obtained residue was dissolved in a mixed solvent of tetrahydrofuran and ethyl acetate, and the solution was washed with water, and dried over anhydrous sodium sulfate. The solvent was evaporated under reduced pressure. A mixture of the obtained residue and 1,1,1-triethoxyethane (13.76 g), methanesulfonic acid (0.37 mL) and tetrahydrofuran (100 mL) was heated under reflux for 9 hr. The reaction mixture was allowed to be cooled to room temperature, saturated aqueous sodium hydrogen carbonate solution was added thereto, and the mixture was extracted with ethyl acetate. The extract was washed with saturated aqueous sodium hydrogen carbonate solution, and dried over anhydrous sodium sulfate. The solvent was evaporated under reduced pressure. The residue was suspended in diisopropyl ether, and the solid was collected by filtration, washed with diisopropyl ether, and dried to give the title compound (5.776 g).

$^1$H NMR (300 MHz, CDCl$_3$) δ 2.61 (3H, s), 7.15 (1H, d, J=16.6 Hz), 7.55 (1H, d, J=16.6 Hz), 7.69 (2H, d, J=8.7 Hz), 8.28 (2H, d, J=9.0 Hz).

B) 4-[2-(5-methyl-1,3,4-oxadiazol-2-yl)ethyl]aniline

To a mixture of 2-methyl-5-[(E)-2-(4-nitrophenyl)ethenyl]-1,3,4-oxadiazole (2.00 g), tetrahydrofuran (75 mL) and methanol (75 mL) was added palladium-carbon (Pd: 10%, 50% in water, 200 mg), and the mixture was stirred under a hydrogen atmosphere at room temperature for 6 hr. The reaction mixture was filtered, and the filtrate was concentrated under reduced pressure to give the title compound (1.807 g).

$^1$H NMR (300 MHz, CDCl$_3$) δ 2.49 (3H, s), 2.92-3.12 (4H, m), 3.59 (2H, brs), 6.63 (2H, d, J=8.7 Hz), 7.00 (2H, d, J=8.3 Hz).

C) (2E)-3-[4-(4-fluorophenyl)pyridin-3-yl]-N-{4-[2-(5-methyl-1,3,4-oxadiazol-2-yl)ethyl]phenyl}prop-2-enamide A mixture of (2E)-3-[4-(4-fluorophenyl)pyridin-3-yl] prop-2-enoic acid (730 mg), 4-[2-(5-methyl-1,3,4-oxadiazol-2-yl)ethyl]aniline (640 mg), 1-hydroxy-1H-1,2,3-benzotriazole monohydrate (505 mg), 1-ethyl-3-(3-dimethylaminopropyl)carbodiimide hydrochloride (733 mg) and N,N-dimethylformamide (15 mL) was stirred at room temperature for 21 hr. To the reaction mixture was added water, and the mixture was extracted with ethyl acetate. The extract was washed with saturated brine, and dried over anhydrous sodium sulfate. The solvent was evaporated under reduced pressure. The residue was purified by silica gel column chromatography (ethyl acetate/methanol), and the obtained solid was recrystallized from water-containing ethanol to give the title compound (941 mg).

$^1$H NMR (300 MHz, CDCl$_3$) δ 2.50 (3H, s), 3.10 (4H, s), 6.59 (1H, d, J=15.4 Hz), 7.12-7.23 (4H, m), 7.27-7.39 (3H, m), 7.44-7.60 (3H, m), 7.74 (1H, d, J=15.4 Hz), 8.62 (1H, d, J=4.9 Hz), 8.91 (1H, s).

Example 4

(2E)-3-[4-(4-fluorophenyl)pyrimidin-5-yl]-N-{4-[2-(1,3,4-oxadiazol-2-yl)ethyl]phenyl}prop-2-enamide

A) ethyl 4-(4-fluorophenyl)-2-(methylsulfanyl)pyrimidine-5-carboxylate

A mixture of ethyl 3-(4-fluorophenyl)-3-oxopropanoate (16.7 g), 1,1-dimethoxy-N,N-dimethylmethanamine (14.9 g) and toluene (250 mL) was heated under reflux overnight, and the solvent was evaporated under reduced pressure to give an oil (21.0 g).

To a solution of S-methylisothiourea sulfate (13.2 g) in ethanol (350 mL) was slowly added sodium ethoxide (20% ethanol solution, 6.47 g) at 0° C., and the mixture was stirred at room temperature for 15 min. The precipitate was filtered off, and the filtrate was added to a solution of the above-mentioned oil (21.0 g) in tetrahydrofuran (250 mL). The reaction mixture was heated under reflux for 3 hr, and the solvent was evaporated under reduced pressure. To the residue was added water, and the mixture was extracted with ethyl acetate. The extract was washed with saturated brine, and dried over anhydrous sodium sulfate, and the solvent was evaporated under reduced pressure. The residue was purified by silica gel column chromatography (petroleum ether/ethyl acetate) to give the title compound (21.0 g).

¹H NMR (400 MHz, CDCl₃) δ 1.20 (3H, t, J=7.2 Hz), 2.65 (3H, s), 4.26 (2H, q, J=7.2 Hz), 7.14-7.18 (2H, m), 7.61-7.65 (2H, m), 8.94 (1H, s).

B) [4-(4-fluorophenyl)-2-(methylsulfanyl)pyrimidin-5-yl]methanol

To a solution of ethyl 4-(4-fluorophenyl)-2-(methylsulfanyl)pyrimidine-5-carboxylate (21.0 g) in toluene (500 mL) was added diisobutylaluminum hydride (15% toluene solution, 124 mL) at −78° C. The reaction mixture was stirred at −78° C. for 1.5 hr, and the reaction was quenched with acetic acid. The reaction mixture was extracted with ethyl acetate, and the extract was washed successively with saturated aqueous sodium carbonate solution and saturated brine, and dried over anhydrous sodium sulfate. The solvent was evaporated under reduced pressure to give the title compound (10.3 g).

¹H NMR (400 MHz, CDCl₃) δ 2.63 (3H, s), 4.69 (2H, s), 7.18-7.23 (2H, m), 7.81-7.85 (2H, m), 8.66 (1H, s).

C) [4-(4-fluorophenyl)pyrimidin-5-yl]methanol

A mixture of [4-(4-fluorophenyl)-2-(methylsulfanyl)pyrimidin-5-yl]methanol (10.3 g), Raney-nickel (77 g) and ethanol (500 mL) was heated under reflux for 2 hr. The reaction mixture was filtered, and the filtrate was concentrated under reduced pressure. The residue was purified by silica gel column chromatography (petroleum ether/ethyl acetate) to give the title compound (4.8 g).

¹H NMR (400 MHz, CDCl₃) δ 4.77 (2H, s), 7.19-7.26 (2H, m), 7.74-7.78 (2H, m), 8.91 (1H, s), 9.22 (1H, s).

D) 4-(4-fluorophenyl)pyrimidine-5-carbaldehyde

A mixture of [4-(4-fluorophenyl)pyrimidin-5-yl]methanol (4.8 g), manganese dioxide (28 g) and tetrahydrofuran (300 mL) was stirred overnight at room temperature. The reaction mixture was filtered, and the filtrate was concentrated under reduced pressure to give the title compound (3.6 g).

¹H NMR (400 MHz, CDCl₃) δ 7.29-7.34 (2H, m), 7.71-7.75 (2H, m), 9.27 (1H, s), 9.44 (1H, s), 10.17 (1H, s).

E) (2E)-3-[4-(4-fluorophenyl)pyrimidin-5-yl]prop-2-enoic acid

To a mixture of sodium hydride (60% in oil, 1.14 g) and N,N-dimethylformamide (150 mL) was slowly added triethyl phosphonoacetate (6.4 g) under ice-cooling, and the mixture was stirred until completion of the generation of hydrogen gas. To the reaction mixture was slowly added a solution of 4-(4-fluorophenyl)pyrimidine-5-carbaldehyde (5.25 g) in N,N-dimethylformamide (50 mL) under ice-cooling, and the mixture was stirred for 1 hr. To the reaction mixture was added a saturated aqueous ammonium chloride solution (50 mL), and the mixture was extracted with ethyl acetate. The extract was washed with saturated brine, and dried over anhydrous sodium sulfate, and the solvent was evaporated under reduced pressure. A mixture of the obtained residue, lithium hydroxide monohydrate (4.0 g), water (30 mL), tetrahydrofuran (100 mL) and ethanol (100 mL) was stirred at room temperature for 30 min. The pH of the reaction mixture was adjusted to 3 with 1 M hydrochloric acid. The solvent was evaporated under reduced pressure. To the residue was added water, and the mixture was extracted with ethyl acetate. The extract was washed with saturated brine, and dried over anhydrous sodium sulfate, and the solvent was evaporated under reduced pressure. The obtained solid was recrystallized from ethyl acetate/petroleum ether to give the title compound (4.16 g).

¹H NMR (400 MHz, DMSO-d₆) δ 6.75 (1H, d, J=16.0 Hz), 7.43-7.50 (3H, m), 7.69-7.71 (2H, m), 9.24 (2H, s).

F) (2E)-3-[4-(4-fluorophenyl)pyrimidin-5-yl]-N-{4-[2-(1,3,4-oxadiazol-2-yl)ethyl]phenyl}prop-2-enamide To a mixture of (2E)-3-[4-(4-fluorophenyl)pyrimidin-5-yl]prop-2-enoic acid (977 mg), N,N-dimethylformamide (1 drop) and tetrahydrofuran (20 mL) was added oxalyl chloride (0.51 mL), and the mixture was stirred at room temperature for 4 hr. The reaction mixture was concentrated under reduced pressure, to the residue was added toluene, and the mixture was concentrated under reduced pressure. The residue was dissolved in N,N-dimethylformamide (20 mL), triethylamine (0.61 mL) and 4-[2-(1,3,4-oxadiazol-2-yl)ethyl]aniline (833 mg) were added thereto, and the mixture was stirred at room temperature 1.5 hr. To the reaction mixture was added saturated aqueous sodium hydrogen carbonate solution, and the mixture was extracted with ethyl acetate. The extract was washed with saturated brine, and dried over anhydrous sodium sulfate. The solvent was evaporated under reduced pressure. The residue was purified by silica gel column chromatography (ethyl acetate/methanol). The obtained solid was recrystallized from water-containing ethanol to give the title compound (924 mg).

¹H NMR (300 MHz, CDCl₃) δ 3.08-3.26 (4H, m), 6.61 (1H, d, J=15.8 Hz), 7.22 (4H, t, J=8.7 Hz), 7.34 (1H, s), 7.55 (2H, d, J=7.9 Hz), 7.70 (2H, dd, J=8.7, 5.3 Hz), 7.82 (1H, d, J=15.4 Hz), 8.33 (1H, s), 8.95 (1H, s), 9.24 (1H, s).

Example 5

(2E)-3-[4-(4-methoxyphenyl)pyrimidin-5-yl]-N-{4-[2-(1,3,4-oxadiazol-2-yl)ethyl]phenyl}prop-2-enamide A) ethyl 4-(4-methoxyphenyl)-2-(methylsulfanyl)pyrimidine-5-carboxylate A mixture of ethyl 3-(4-methoxyphenyl)-3-oxopropanoate (22.8 g), 1,1-dimethoxy-N,N-dimethylmethanamine (19.3 g) and toluene (350 mL) was heated under reflux overnight. The solvent was evaporated under reduced pressure to give an oil (28.5 g).

To a solution of S-methylisothiourea sulfate (18.6 g) in ethanol (350 mL) was slowly added sodium ethoxide (20% ethanol solution, 9.04 g) at 0° C., and the mixture was stirred at room temperature for 15 min. The precipitate was filtered off, and the filtrate was added to a solution of the above-mentioned oil (28.5 g) in tetrahydrofuran (250 mL). The reaction mixture was heated under reflux for 3 hr, and the solvent was evaporated under reduced pressure. To the residue was added water, and the mixture was extracted with ethyl acetate. The extract was washed with saturated brine, and dried over anhydrous sodium sulfate, and the solvent was evaporated under reduced pressure. The residue was purified by silica gel column chromatography (petroleum ether/ethyl acetate) to give the title compound (23.1 g).

¹H NMR (400 MHz, CDCl₃) δ 1.23 (3H, t, J=7.2 Hz), 2.66 (3H, s), 3.90 (3H, s), 4.28 (2H, q, J=7.2 Hz), 6.98-7.00 (2H, m), 7.63-7.66 (2H, m), 8.87 (1H, s).

B) [4-(4-methoxyphenyl)-2-(methylsulfanyl)pyrimidin-5-yl]methanol

To a solution of ethyl 4-(4-methoxyphenyl)-2-(methylsulfanyl)pyrimidine-5-carboxylate (23.1 g) in toluene (500 mL) was added diisobutylaluminum hydride (15% toluene solution, 131 mL) at −78° C. The reaction mixture was stirred at −78° C. for 1.5 hr, and quenched with acetic acid. The reaction mixture was extracted with ethyl acetate, and the extract was washed successively with saturated aqueous sodium carbonate solution and saturated brine, and dried over anhydrous sodium sulfate. The solvent was evaporated under reduced pressure to give the title compound (13.5 g).
$^1$H NMR (400 MHz, CDCl$_3$) δ 2.64 (3H, s), 3.90 (3H, s), 4.73 (2H, s), 7.03-7.05 (2H, m), 7.79-7.81 (2H, m), 8.63 (1H, s).

C) [4-(4-methoxyphenyl)pyrimidin-5-yl]methanol

A mixture of [4-(4-methoxyphenyl)-2-(methylsulfanyl)pyrimidin-5-yl]methanol (13.5 g), Raney-nickel (96 g) and ethanol (500 mL) was heated under reflux for 2 hr. The reaction mixture was filtered, and the filtrate was concentrated under reduced pressure. The residue was purified by silica gel column chromatography (petroleum ether/ethyl acetate) to give the title compound (8.6 g).
$^1$H NMR (400 MHz, CDCl$_3$) δ 3.91 (3H, s), 4.83 (2H, s), 7.06 (2H, d, J=8.8 Hz), 7.75 (2H, d, J=8.8 Hz), 8.90 (1H, s), 9.22 (1H, s).

D) 4-(4-methoxyphenyl)pyrimidine-5-carbaldehyde

A mixture of [4-(4-methoxyphenyl)pyrimidin-5-yl]methanol (8.6 g), manganese dioxide (48 g) and tetrahydrofuran (300 mL) was stirred overnight at room temperature. The reaction mixture was filtered, and the filtrate was concentrated under reduced pressure to give the title compound (5.32 g).
$^1$H NMR (400 MHz, CDCl$_3$) δ 3.94 (3H, s), 7.12 (2H, d, J=8.8 Hz), 7.75 (2H, d, J=8.8 Hz), 9.21 (1H, s), 9.39 (1H, s), 10.17 (1H, s).

E) (2E)-3-[4-(4-methoxyphenyl)pyrimidin-5-yl]prop-2-enoic acid

To a mixture of sodium hydride (60% in oil, 1.09 g) and N,N-dimethylformamide (150 mL) was slowly added triethyl phosphonoacetate (6.12 g) under ice-cooling, and the mixture was stirred until completion of the generation of hydrogen gas. To the reaction mixture was slowly added a solution of 4-(4-methoxyphenyl)pyrimidine-5-carbaldehyde (5.32 g) in N,N-dimethylformamide (50 mL) under ice-cooling, and the mixture was stirred for 1 hr. To the reaction mixture was added a saturated aqueous ammonium chloride solution (50 mL), and the mixture was extracted with ethyl acetate. The extract was washed with saturated brine, and dried over anhydrous sodium sulfate, and the solvent was evaporated under reduced pressure. The obtained residue, lithium hydroxide monohydrate (3.6 g), water (30 mL), tetrahydrofuran (100 mL) and ethanol (100 mL) were stirred at room temperature for 30 min. The pH of the reaction mixture was adjusted to 3 with 1 M hydrochloric acid, and the solvent was evaporated under reduced pressure. To the residue was added water, and the mixture was extracted with ethyl acetate. The extract was washed with saturated brine, and dried over anhydrous sodium sulfate, and the solvent was evaporated under reduced pressure to give the title compound (3.42 g).
$^1$H NMR (400 MHz, DMSO-d$_6$) δ 3.87 (3H, s), 6.73 (1H, d, J=15.6 Hz), 7.15 (2H, dd, J=6.8, 2.0 Hz), 7.54 (1H, d, J=15.6 Hz), 7.63 (2H, dd, J=6.8, 2.0 Hz), 9.24 (2H, d, J=10.4 Hz), 12.67 (1H, brs).

F) (2E)-3-[4-(4-methoxyphenyl)pyrimidin-5-yl]-N-{4-[2-(1,3,4-oxadiazol-2-yl)ethyl]phenyl}prop-2-enamide To a mixture of (2E)-3-[4-(4-methoxyphenyl)pyrimidin-5-yl]prop-2-enoic acid (1.025 g), N,N-dimethylformamide (1 drop) and tetrahydrofuran (20 mL) was added oxalyl chloride (0.51 mL), and the mixture was stirred at room temperature for 3 hr. The reaction mixture was concentrated under reduced pressure, to the residue was added toluene, and the mixture was concentrated under reduced pressure. The residue was dissolved in N,N-dimethylformamide (20 mL), triethylamine (0.61 mL) and 4-[2-(1,3,4-oxadiazol-2-yl)ethyl]aniline (833 mg) were added thereto, and the mixture was stirred at room temperature for 3 hr. To the reaction mixture was added saturated aqueous sodium hydrogen carbonate solution, and the mixture was extracted with ethyl acetate. The extract was washed with saturated brine, and dried over anhydrous sodium sulfate, and the solvent was evaporated under reduced pressure. The residue was purified by silica gel column chromatography (ethyl acetate/methanol). The obtained solid was recrystallized from water-containing ethanol to give the title compound (913 mg).
$^1$H NMR (300 MHz, CDCl$_3$) δ 3.07-3.27 (4H, m), 3.88 (3H, s), 6.59 (1H, d, J=15.4 Hz), 7.04 (2H, d, J=8.7 Hz), 7.21 (2H, d, J=8.3 Hz), 7.33 (1H, s), 7.55 (2H, d, J=7.5 Hz), 7.68 (2H, d, J=8.7 Hz), 7.86 (1H, d, J=15.4 Hz), 8.33 (1H, s), 8.90 (1H, s), 9.21 (1H, s).

Example 6

(2E)-3-[4-(4-fluorophenyl)pyridin-3-yl]-N-[4-(morpholin-4-ylmethyl)phenyl]prop-2-enamide To a mixture of (2E)-3-[4-(4-fluorophenyl)pyridin-3-yl]prop-2-enoic acid (300 mg), N,N-dimethylformamide (1 drop) and tetrahydrofuran (10 mL) was added oxalylchloride (0.11 mL), and the mixture was stirred at room temperature for 30 min. The reaction mixture was concentrated under reduced pressure, to the residue was added toluene, and the mixture was concentrated under reduced pressure. The residue was dissolved in N,N-dimethylformamide (10 mL), 4-(morpholin-4-ylmethyl)aniline (215 mg) were added thereto, and the mixture was stirred at room temperature for 1.5 hr. To the reaction mixture were added water and a saturated aqueous sodium hydrogen carbonate solution, and the resulting solid was collected by filtration. The obtained solid was purified by silica gel column chromatography (NH, ethyl acetate/methanol). The obtained solid was suspended in diisopropyl ether, collected by filtration, washed with diisopropyl ether, and dried to give the title compound (379 mg).
$^1$H NMR (300 MHz, CDCl$_3$) δ 2.38-2.49 (4H, m), 3.47 (2H, s), 3.66-3.75 (4H, m), 6.58 (1H, d, J=15.4 Hz), 7.14-7.23 (2H, m), 7.28-7.39 (6H, m), 7.55 (2H, d, J=7.9 Hz), 7.74 (1H, d, J=15.4 Hz), 8.62 (1H, d, J=4.9 Hz), 8.91 (1H, s).

Example 7

(2E)-3-[4-(4-fluorophenyl)pyridin-3-yl]-N-{4-[(methylsulfonyl)methyl]phenyl}prop-2-enamide A mixture of (2E)-3-[4-(4-fluorophenyl)pyridin-3-yl]prop-2-enoic acid (0.24 g), 4-[(methylsulfonyl)methyl]

aniline (0.19 g), 1-ethyl-3-(3-dimethylaminopropyl)carbodiimide hydrochloride (0.25 g), 1-hydroxy-1H-1,2,3-benzotriazole (0.20 g) and N,N-dimethylformamide (10 mL) was stirred at room temperature for 15 hr. To the reaction mixture was added water, and the mixture was extracted with ethyl acetate. The extract was washed with saturated brine, dried over anhydrous magnesium sulfate and the solvent was evaporated under reduced pressure to give a solid. The obtained solid was recrystallized from acetone/hexane to give the title compound (0.28 g).

$^1$H NMR (500 MHz, DMSO-$d_6$) δ 2.88 (3H, s), 4.42 (2H, s), 6.91 (1H, d, J=15.8 Hz), 7.34-7.50 (8H, m), 7.63-7.70 (2H, m), 8.63 (1H, d, J=5.1 Hz), 8.93 (1H, s), 10.38 (1H, s).

Example 8

(2E)-N-[4-(1H-benzimidazol-1-ylmethyl)phenyl]-3-[4-(4-fluorophenyl)pyridin-3-yl]prop-2-enamide By a method according to Example 7, the title compound (0.34 g) was obtained from (2E)-3-[4-(4-fluorophenyl)pyridin-3-yl]prop-2-enoic acid (0.24 g) and 4-(1H-benzimidazol-1-ylmethyl)aniline (0.22 g).

$^1$H NMR (500 MHz, DMSO-$d_6$) δ 5.44 (2H, s), 6.87 (1H, d, J=15.8 Hz), 7.18-7.67 (14H, m), 8.39 (1H, s), 8.62 (1H, d, J=5.1 Hz), 8.90 (1H, s), 10.30 (1H, s).

Example 9

(2E)-3-[4-(4-fluorophenyl)pyridin-3-yl]-N-[4-(1H-imidazol-1-ylmethyl)phenyl]prop-2-enamide By a method according to Example 7, the title compound (0.27 g) was obtained from (2E)-3-[4-(4-fluorophenyl)pyridin-3-yl]prop-2-enoic acid (0.24 g) and 4-(1H-imidazol-1-ylmethyl)aniline (0.17 g).

$^1$H NMR (500 MHz, DMSO-$d_6$) δ 5.10 (2H, s), 6.63 (1H, d, J=15.5 Hz), 6.91 (1H, s), 7.10-7.36 (8H, m), 7.56-7.62 (3H, m), 7.75 (1H, d, J=15.5 Hz), 7.88 (1H, brs), 8.62 (1H, d, J=4.9 Hz), 8.94 (1H, s).

Example 10

(2E)-3-[4-(4-fluorophenyl)pyridin-3-yl]-N-[4-(1,3,4-oxadiazol-2-ylmethoxy)phenyl]prop-2-enamide By a method according to Example 2, C), the title compound (0.18 g) was obtained from (2E)-3-[4-(4-fluorophenyl)pyridin-3-yl]prop-2-enoic acid (0.27 g) and 4-(1,3,4-oxadiazol-2-ylmethoxy)aniline (0.21 g).

$^1$H NMR (500 MHz, DMSO-$d_5$) δ 5.42 (2H, s), 6.87 (1H, d, J=15.6 Hz), 7.01-7.07 (2H, m), 7.35-7.63 (8H, m), 8.63 (1H, d, J=4.9 Hz), 8.92 (1H, s), 9.31 (1H, s), 10.22 (1H, s).

Example 11 diethyl (4-{[(2E)-3-(4-phenylpyridin-3-yl)prop-2-enoyl]amino}benzyl)phosphonate

By a method according to Example 7, the title compound (276 mg) was obtained from (2E)-3-(4-phenylpyridin-3-yl)prop-2-enoic acid (225 mg) and diethyl (4-aminobenzyl)phosphonate (304 mg).

MS (ESI+): [M+H]$^+$451.2

Example 12 dimethyl (4-{[(2E)-3-(4-phenylpyridin-3-yl)prop-2-enoyl]amino}benzyl)phosphonoate By a method according to Example 7, the title compound (286 mg) was obtained from (2E)-3-(4-phenylpyridin-3-yl)prop-2-enoic acid (225 mg) and dimethyl (4-aminobenzyl)phosphonate (269 mg).

MS (ESI+): [M+H]$^+$423.2

Example 13 diethyl [4-({(2E)-3-[4-(4-fluorophenyl)pyridin-3-yl]prop-2-enoyl}amino)benzyl]phosphonoate By a method according to Example 7, the title compound (650 mg) was obtained from (2E)-3-[4-(4-fluorophenyl)pyridin-3-yl]prop-2-enoic acid (486 mg) and diethyl (4-aminobenzyl)phosphonate (606 mg).

$^1$H NMR (300 MHz, CDCl$_3$) δ 1.26 (6H, t, J=7.1 Hz), 3.13 (2H, d, J=21.6 Hz), 3.90-4.10 (4H, m), 6.75 (1H, d, J=15.3 Hz), 7.13-7.37 (7H, m), 7.48-7.58 (2H, m), 7.72 (1H, d, J=15.6 Hz), 8.60 (1H, d, J=4.8 Hz), 8.69 (1H, brs), 8.89 (1H, s).

Example 14 dimethyl [4-({(2E)-3-[4-(4-fluorophenyl)pyridin-3-yl]prop-2-enoyl}amino)benzyl]phosphonate By a method according to Example 7, the title compound (560 mg) was obtained from (2E)-3-[4-(4-fluorophenyl)pyridin-3-yl]prop-2-enoic acid (486 mg) and dimethyl (4-aminobenzyl)phosphonate (540 mg).

$^1$H NMR (300 MHz, CDCl$_3$) δ 3.20 (2H, d, J=29.1 Hz), 3.59 (6H, d, J=10.8 Hz), 6.90 (1H, d, J=15.6 Hz), 7.16-7.25 (2H, m), 7.36-7.64 (8H, m), 8.61 (1H, d, J=5.1 Hz), 8.91 (1H, s), 10.26 (1H, s).

Table 1 and Table 2 show the chemical names, structural formulas and actual values of MS of the Example compounds.

TABLE 1

| Example | IUPAC Name | Structure | MS |
|---|---|---|---|
| 1 | (2E)-3-[4-(4-fluorophenyl)pyridin-3-yl]-N-{4-[2-(1,3,4-oxadiazol-2-yl)ethyl]phenyl}prop-2-enamide | 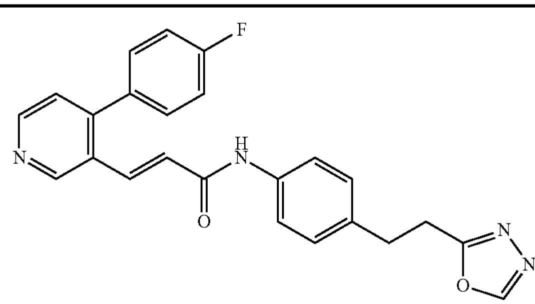 | 415.0 |

TABLE 1-continued

| Example | IUPAC Name | Structure | MS |
|---|---|---|---|
| 2 | (2E)-3-[4-(4-methoxyphenyl)pyridin-3-yl]-N-{4-[2-(1,3,4-oxadiazol-2-yl)ethyl]phenyl}prop-2-enamide | 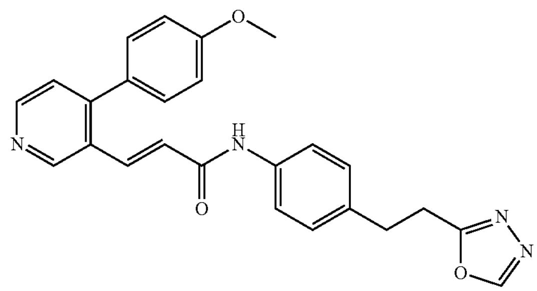 [SMILES: COc1ccc(-c2ccncc2/C=C/C(=O)Nc2ccc(CCc3nnco3)cc2)cc1] | 427.2 |
| 3 | (2E)-3-[4-(4-fluorophenyl)pyridin-3-yl]-N-{4-[2-(5-methyl-1,3,4-oxadiazol-2-yl)ethyl]phenyl}prop-2-enamide | 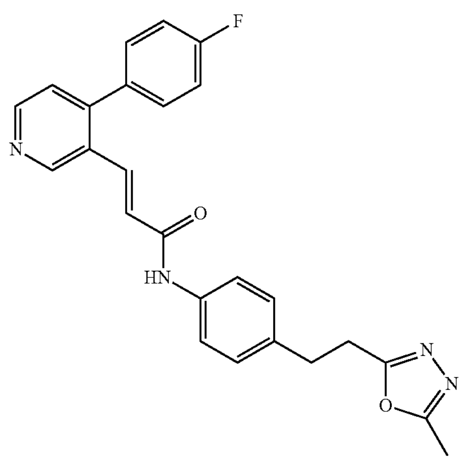 [SMILES: Cc1nnc(CCc2ccc(NC(=O)/C=C/c3cnccc3-c3ccc(F)cc3)cc2)o1] | 429.1 |
| 4 | (2E)-3-[4-(4-fluorophenyl)pyrimidin-5-yl]-N-{4-[2-(1,3,4-oxadiazol-2-yl)ethyl]phenyl}prop-2-enamide | 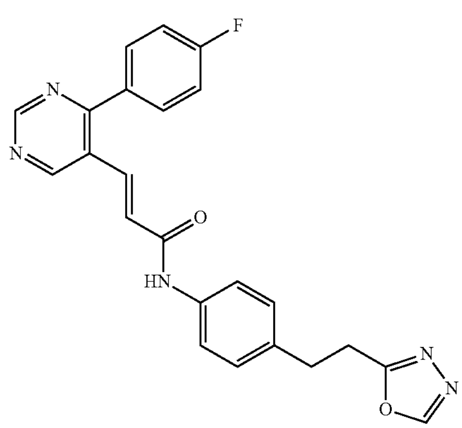 [SMILES: O=C(/C=C/c1cncnc1-c1ccc(F)cc1)Nc1ccc(CCc2nnco2)cc1] | 416.1 |
| 5 | (2E)-3-[4-(4-methoxyphenyl)pyrimidin-5-yl]-N-{4-[2-(1,3,4-oxadiazol-2-yl)ethyl]phenyl}prop-2-enamide | 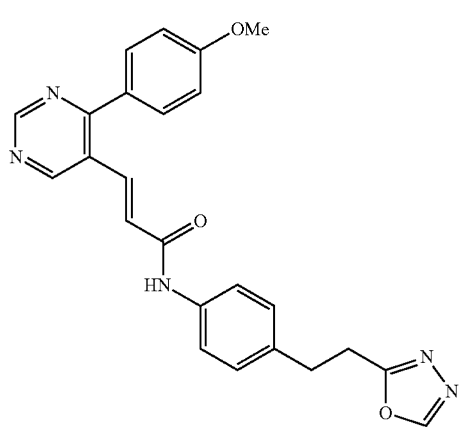 [SMILES: COc1ccc(-c2ncncc2/C=C/C(=O)Nc2ccc(CCc3nnco3)cc2)cc1] | 428.0 |

TABLE 1-continued

| Example | IUPAC Name | Structure | MS |
|---|---|---|---|
| 6 | (2E)-3-[4-(4-fluorophenyl)pyridin-3-yl]-N-[4-(morpholin-4-ylmethyl)phenyl]prop-2-enamide | 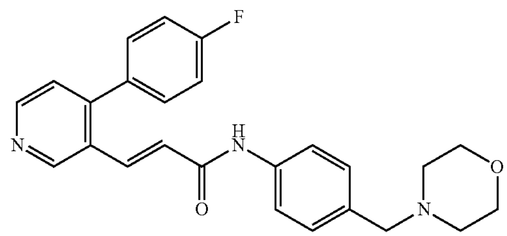 [SMILES: O=C(/C=C/c1cnccc1-c1ccc(F)cc1)Nc1ccc(CN2CCOCC2)cc1] | 418.1 |
| 7 | (2E)-3-[4-(4-fluorophenyl)pyridin-3-yl]-N-{4-[(methylsulfonyl)methyl]phenyl}prop-2-enamide | 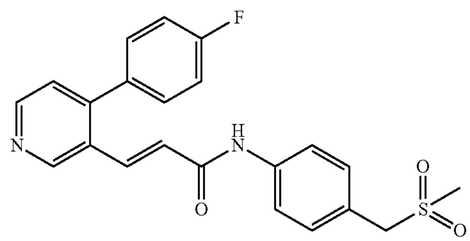 [SMILES: CS(=O)(=O)Cc1ccc(NC(=O)/C=C/c2cnccc2-c2ccc(F)cc2)cc1] | — |

1H NMR (300 MHz, DMSO-d$_6$) δ 2.88 (3H, s), 4.42 (2H, s), 6.91 (1H, d, J = 15.8 Hz), 7.34-7.50 (8H, m), 7.67-7.70 (2H, m), 8.63 (1H, d, J = 5.1 Hz), 8.93 (1H, s), 10.38 (1H, s).

| Example | IUPAC Name | Structure | MS |
|---|---|---|---|
| 8 | (2E)-N-[4-(1H-benzimidazol-1-ylmethyl)phenyl]-3-[4-(4-fluorophenyl)pyridin-3-yl]prop-2-enamide | | — |

1H NMR (300 MHz, DMSO-d$_6$) δ 5.44 (2H, s), 6.87 (1H, d, J = 15.8 Hz), 7.18-7.67 (14H, m), 8.39 (1H, s), 8.62 (1H, d, J = 5.1 Hz), 8.90 (1H, s), 10.30 (1H, s).

TABLE 2

| Example | IUPAC Name | Structure | MS |
|---|---|---|---|
| 9 | (2E)-3-[4-(4-fluorophenyl)pyridin-3-yl]-N-[4-(1H-imidazol-1-ylmethyl)phenyl]prop-2-enamide | 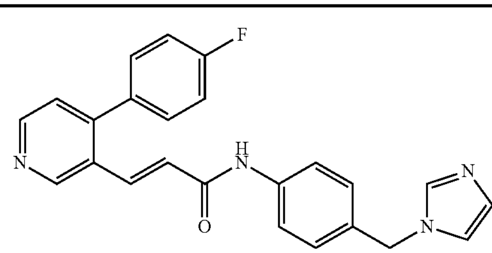 | — |

1H NMR (300 MHz, CDCl$_3$) δ 5.10 (2H, s), 6.63 (1H, d, J = 15.5 Hz), 6.91 (1H, s), 7.10-7.36 (8H, m), 7.56-7.62 (3H, m), 7.75 (1H, d, J = 15.5 Hz), 7.88 (1H, brs), 8.62 (1H, d, J = 4.9 Hz), 8.94 (1H, s).

TABLE 2-continued

| Example | IUPAC Name | Structure | MS |
|---|---|---|---|
| 10 | (2E)-3-[4-(4-fluorophenyl)pyridin-3-yl]-N-[4-(1,3,4-oxadiazol-2-ylmethoxy)phenyl]prop-2-enamide | 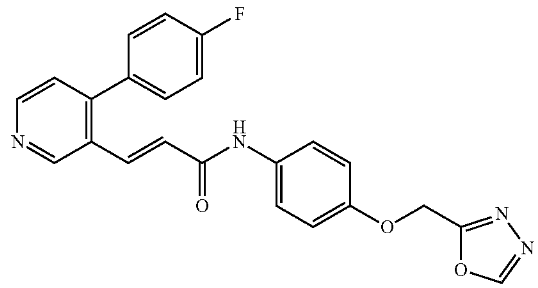 [SMILES: O=C(/C=C/c1cnccc1-c1ccc(F)cc1)Nc1ccc(OCc2nnco2)cc1] | — |

1H NMR (300 MHz, DMSO-d$_6$) δ 5.42 (2H, s), 6.87 (1H, d, J = 15.6 Hz), 7.01-7.07 (2H, m), 7.35-7.63 (8H, m), 8.63 (1H, d, J = 4.9 Hz), 8.92 (1H, s), 9.31 (1H, s), 10.22 (1H, s).

| Example | IUPAC Name | Structure | MS |
|---|---|---|---|
| 11 | diethyl (4-{[(2E)-3-(4-phenylpyridin-3-yl)prop-2-enoyl]amino}benzyl)phosphonate | 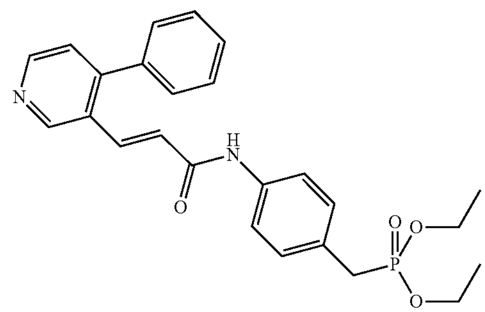 [SMILES: CCOP(=O)(Cc1ccc(NC(=O)/C=C/c2cnccc2-c2ccccc2)cc1)OCC] | 451.2 |
| 12 | dimethyl (4-{[(2E)-3-(4-phenylpyridin-3-yl)prop-2-enoyl]amino}benzyl)phosphonate | 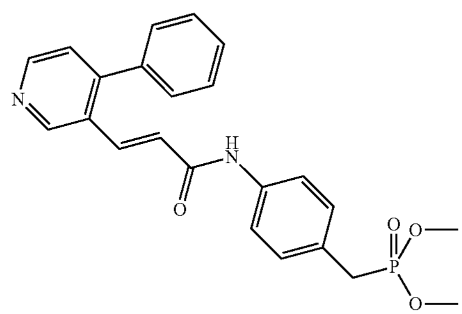 [SMILES: COP(=O)(Cc1ccc(NC(=O)/C=C/c2cnccc2-c2ccccc2)cc1)OC] | 423.2 |
| 13 | diethyl [4-({(2E)-3-[4-(4-fluorophenyl)pyridin-3-yl]prop-2-enoyl}amino)benzyl]phosphonate | 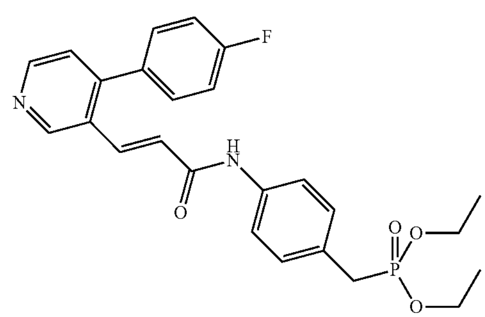 [SMILES: CCOP(=O)(Cc1ccc(NC(=O)/C=C/c2cnccc2-c2ccc(F)cc2)cc1)OCC] | — |

1H NMR (300 MHz, CDCl$_3$) δ 1.26 (6H, t, J = 7.1 Hz), 3.13 (2H, d, J = 21.6 Hz), 3.90-4.10 (4H, m), 6.75 (1H, d, J = 15.3 Hz), 7.13-7.37 (7H, m), 7.48-7.58 (2H, m), 7.72 (1H, d, J = 15.6 Hz), 8.60 (1H, d, J = 4.8 Hz), 8.69 (1H, brs), 8.89 (1H, s).

TABLE 2-continued

| Example | IUPAC Name | Structure | MS |
|---|---|---|---|
| 14 | dimethyl [4-({(2E)-3-[4-(4-fluorophenyl)pyridin-3-yl]prop-2-enoyl}amino)benzyl]phosphonate | 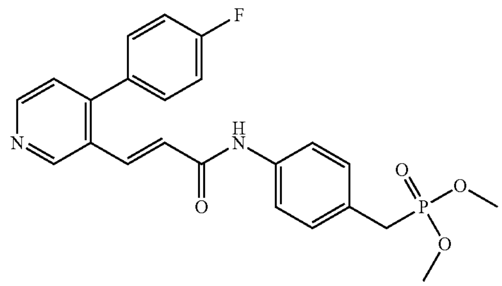 [SMILES: COP(=O)(Cc1ccc(NC(=O)/C=C/c2cnccc2-c2ccc(F)cc2)cc1)OC] | — |

1H NMR (300 MHz, DMSO-$d_6$) δ 3.20 (2H, d, J = 29.1 Hz), 3.59 (6H, d, J = 10.8 Hz), 6.90 (1H, d, J = 15.6 Hz), 7.16-7.25 (2H, m), 7.36-7.64 (8H, m), 8.61 (1H, d, J = 5.1 Hz), 8.91 (1H, s), 10.26 (1H, s).

Experimental Example 1

Evaluation of Cell Differentiation Promoting Activity in Myoblast (1) Mouse-derived myoblast line C2C12 cell (Dainippon Pharmaceutical Co., Ltd.) was subcultured in a high glucose Eagle's modified Dulbecco's medium (GIBCO) containing 10% calf fetal bovine serum (GIBCO), 100 unit/mL penicillin and 100 μg/mL streptomycin (hereinafter to be referred to as a growth medium), plated at 5000 cells/cm² and cultured at 37° C., under 5% $CO_2$.

(2) When the cells reached subconfluence, the medium was exchanged with a high glucose Eagle's modified Dulbecco's medium (GIBCO) containing 2% horse serum (GIBCO) and penicillin, streptomycin and a test compound (hereinafter to be referred to as a differentiation medium), and the cells were cultured for 2 days. To the control group was added DMSO solution instead of the test compound.

(3) The cells were washed with PBS, 0.5% NP-40 solution was added thereto, and the cells were lysed by freeze-thawing. The cell extract was centrifuged, and the creatine kinase activity in the supernatant was measured as an index of muscle differentiation. The creatine kinase activity was measured using CPKII Test Wako (Wako Pure Chemical Industries, Ltd.) according to the manual of the kit. The tests using the compounds of Example 7 to Example 14 were corrected based on the total protein amount measured using CA Protein Assay Kit (Thermo Scientific).

The creatine kinase activity of C2C12 cell treated with the compound is shown in Table 3. The numerical values in Table 3 show CK activity of the compound addition group with the CK activity without addition of the compound as 100%, and 1 μM of the compound was added for the measurement.

TABLE 3

| Example No. | creatinine kinase activating action (%) |
|---|---|
| 1 | 196.1 |
| 2 | 211 |
| 3 | 249.3 |
| 4 | 249.3 |
| 5 | 290.4 |
| 6 | 298.7 |
| 7 | 197.2 |

TABLE 3-continued

| Example No. | creatinine kinase activating action (%) |
|---|---|
| 8 | 196.9 |
| 9 | 208.1 |
| 10 | 164.2 |
| 11 | 189.4 |
| 12 | 188.6 |
| 13 | 183.5 |
| 14 | 204.9 |

As shown in Table 3, in C2C12 myoblast, the test compound enhanced the creatine kinase activity specifically expressed in muscle cell, that is, promoted the muscle cell differentiation.

Experimental Example 2

Evaluation of Sugar Metabolism Promoting Activity in Muscle Cell (1) In the same manner as in Experimental Example 1, C2C12 cell was cultured in a growth medium. When the cells reached subconfluence, the medium was exchanged with a differentiation medium, and the cells were cultured for 3 to 4 days while exchanging the medium every 2 or 3 days until the cells differentiated to form a myotube.

(2) After confirmation of myotube formation under a microscope, the compound (1 μM) was added to a differentiation medium and cultured for 2 days. The cells were washed with Krebs-Ringer HEPES phosphate buffer (10 mM HEPES, pH 7.4, 131 mM NaCl, 4.7 mM KCl, 2.5 mM $CaCl_2$-$2H_2O$, 1.2 mM $MgSO_4$-$7H_2O$, 1.2 mM $KH_2PO_4$), the medium was exchanged with Krebs-Ringer HEPES phosphate buffer containing 5 mM glucose, 0.2% fatty acid-free bovine serum albumin, and the cells were cultured at 37° C. for 4 hr.

(3) The lactic acid concentration of the culture supernatant was measured using Detarminer LA kit (Kyowa Medex Co., Ltd.).

Table 4 shows the lactic acid concentration in the culture supernatant of the C2C12 cell containing the compound. The numerical values in Table 4 show the lactic acid concentration of the compound addition group with the lactic acid concentration without addition of the compound as 100%.

TABLE 4

| Example No. | lactic acid production promoting action (%) |
|---|---|
| 1 | 226.1 |
| 2 | 168.3 |
| 3 | 175.4 |
| 4 | 222.9 |
| 5 | 233.3 |
| 6 | 216.7 |

As shown in Table 4, the test compound promoted lactic acid production, i.e., glycolysis, in differentiated C2C12 muscle cell.

Experimental Example 3

Evaluation of Anti-Obesity Action in High-Fat Diet-Loaded Mouse

As male C57BL/6J mouse (CLEA Japan, Inc.), mice fed with a high-fat diet (45 kcal % fat, D12451, research diet) for 40 weeks from 5 weeks old were used. After acclimation bred for 3 weeks, the body weight, ingestion amount, body fat percentage, plasma triglyceride, insulin and leptin concentration were measured, and the mice were divided into 4 groups at 6 per group without difference between them. Plasma total cholesterol concentration was measured using Hitachi automatic analyzer 7180. The compound of Example 1 was suspended in aqueous methylcellulose solution, and the suspension was orally administered repeatedly to 3 groups of the rats divided into 4 groups at 3 mg/kg, 10 mg/kg or 30 mg/kg once a day for 4 weeks. A 0.5% aqueous methylcellulose solution was orally administered similarly to the remaining one group, and the group was used as a control group. On the administration completion day, the body weight and plasma total cholesterol concentration were measured. The results are shown in Table 5. The numerical values in Table 5 show mean±standard deviation at n=6 (n is the number of mice).

TABLE 5

|  | body weight (g) | plasma total cholesterol concentration (mg/dL) | |
|---|---|---|---|
|  |  | before administration | after administration for 4 weeks |
| control group | 53.4 ± 2.1 | 275.3 ± 14.1 | 258.9 ± 23.0 |
| Example 1 3 mg/kg/day | 52.5 ± 2.5 | 265.5 ± 29.7 | 225.9 ± 27.7 |
| Example 1 10 mg/kg/day | 49.0 ± 3.2 | 270.9 ± 24.5 | 192.8 ± 27.6 |
| Example 1 30 mg/kg/day | 44.9 ± 3.1 | 275.9 ± 18.2 | 161.7 ± 16.9 |

As shown in Table 5, the compound of Example 1 showed a body weight decreasing action by administration at 10 mg/kg or above. The plasma index then shows decreased total cholesterol concentration and improved lipid metabolism. It was confirmed that a compound having a muscle cell differentiation promoting or/and adipocyte differentiation suppressive action shows a superior anti-obesity action and dyslipidemia improving action.

Experimental Example 4

NF-kB Activation Suppressive Action in Muscle Cell (1) C2C12 cells introduced with NF-kB reporter plasmid (C2C12/NF-kB-luc, Panomics) was plated at 20000 cells/cm$^2$, 100 µg/ml hygromycin was added thereto, and the cells were cultured in a growth medium in the same manner as in Example 1.
(2) The cells were cultured in a differentiation medium containing the compound of Example 1, Example 8, Example 9, Example 10 or Example 11 for 1 hr, TNF-α was added thereto such that the concentration is 10 ng/mL, and the cells were cultured for 4 hr.
(3) The luciferase activity in the medium was measured using a Stedy-Glo luciferase assay system (Promega). The NF-kB activity was evaluated by measuring the luciferase activity.

Table 6 to Table 10 show the NF-kB activity when the NF-kB activity without addition of TNF-α is 1. The data in Table 6 to Table 10 show mean±standard deviation at n=8 (n is the number of samples).

TABLE 6

| Example 1 (µM) | — | control group | 0.001 | 0.003 | 0.01 | 0.03 | 0.1 | 0.3 | 1 | 3 | 10 |
|---|---|---|---|---|---|---|---|---|---|---|---|
| TNF-α (ng/mL) | — | 10 | 10 | 10 | 10 | 10 | 10 | 10 | 10 | 10 | 10 |
| NF-κB activity (multiple) | 1.0 | 13.0 | 13.2 | 13.4 | 13.7 | 12.5 | 10.7 | 9.4 | 9.3 | 8.3 | 9.0 |
| SD | 0.1 | 1.6 | 1.4 | 1.0 | 1.8 | 1.5 | 1.0* | 1.4* | 1.3* | 1.3* | 1.2* | n = 8,
*: p ≤ 0.025 VS. control group (Williams test)

TABLE 7

| Example 8 (µM) | — | control group | 0.001 | 0.003 | 0.01 | 0.03 | 0.1 | 0.3 | 1 | 3 | 10 |
|---|---|---|---|---|---|---|---|---|---|---|---|
| TNF-α (ng/mL) | — | 10 | 10 | 10 | 10 | 10 | 10 | 10 | 10 | 10 | 10 |
| NF-κB activity (multiple) | 1.0 | 9.1 | 9.4 | 9.7 | 10.8 | 10.6 | 9.4 | 7.6 | 7.1 | 6.6 | 6.1 |
| SD | 0.1 | 1.7 | 0.7 | 1.4 | 1.5 | 0.8 | 0.8 | 0.6* | 1.1* | 0.9* | 0.7* | n = 8,
*: p ≤ 0.025 VS. control group (Williams test)

TABLE 8

| Example 9 (μM) | — | control group | 0.001 | 0.003 | 0.01 | 0.03 | 0.1 | 0.3 | 1 | 3 | 10 |
|---|---|---|---|---|---|---|---|---|---|---|---|
| TNF-α (ng/mL) | — | 10 | 10 | 10 | 10 | 10 | 10 | 10 | 10 | 10 | 10 |
| NF-κB activity (multiple) | 1.0 | 12.6 | 11.8 | 13.0 | 12.1 | 13.1 | 13.0 | 10.2 | 8.4 | 7.6 | 6.9 |
| SD | 0.1 | 1.4 | 1.2 | 1.3 | 0.9 | 1.2 | 1.7 | 0.8* | 1.2* | 0.4* | 0.6* | n = 8,
*: $p \leq 0.025$ VS. control group (Williams test)

TABLE 9

| Example 10 (μM) | — | control group | 0.001 | 0.003 | 0.01 | 0.03 | 0.1 | 0.3 | 1 | 3 | 10 |
|---|---|---|---|---|---|---|---|---|---|---|---|
| TNF-α (ng/mL) | — | 10 | 10 | 10 | 10 | 10 | 10 | 10 | 10 | 10 | 10 |
| NF-κB activity (multiple) | 1.0 | 10.4 | 10.0 | 10.2 | 10.5 | 10.5 | 9.6 | 7.8 | 7.5 | 6.9 | 6.2 |
| SD | 0.1 | 0.9 | 1.2 | 1.2 | 1.2 | 1.4 | 1.4 | 0.7* | 0.8* | 0.8* | 0.8* | n = 8,
*: $p \leq 0.025$ VS. control group (Williams test)

TABLE 10

| Example 11 (μM) | — | control group | 0.001 | 0.003 | 0.01 | 0.03 | 0.1 | 0.3 | 1 | 3 | 10 |
|---|---|---|---|---|---|---|---|---|---|---|---|
| TNF-α (ng/mL) | — | 10 | 10 | 10 | 10 | 10 | 10 | 10 | 10 | 10 | 10 |
| NF-κB activity (multiple) | 1.0 | 10.7 | 9.7 | 10.8 | 10.5 | 10.6 | 10.6 | 9.0 | 7.3 | 7.0 | 5.2 |
| SD | 0.1 | 1.2 | 1.4 | 1.2 | 1.3 | 1.1 | 1.4 | 0.6* | 0.9* | 0.5* | 0.7* | n = 8,
*: $p \leq 0.025$ VS. control group (Williams test)

As shown in Table 6 to Table 10, the NF-kB activity induced by TNF-α was suppressed in a concentration-dependent manner by the addition of the test compound.

Experimental Example 5

Evaluation of Anti-Diabetes Action in KKA$^y$ Mouse

Female KKA$^y$ mice (12-13 week-old, CLEA Japan, Inc.) were bred allowing free ingestion of both feed and water. The mice were acclimation bred with powder CE-2 (CLEA Japan, Inc.) from 2 weeks before administration of the test compound. The body weight, blood glycohemoglobin % (GHb %) value, plasma glucose, triglyceride and total cholesterol concentration were measured, and the mice were divided into 3 groups or 5 groups (6 mice/group) such that those measurement values are uniform at the start of the administration. The compound was administered by mixing (0.01-0.03%) in the feed for 2 weeks. GHb % was measured on the last day. GHb % was measured using Tosoh Corporation automatic glycohemoglobin analyzer (HLC-723GHbV Alc2.2). The numerical values in Table 11 show the variation from the value before administration to the measured value after administration in mean±standard deviation at n=6 (n is the number of mice).

TABLE 11

| Example No. | amount mixed with feed (%) | GHb change (%) |
|---|---|---|
| Example 2 | 0.02 | −1 |
| Example 6 | 0.02 | −1.2 |
| control group | — | −0.2 |
| Example 1 | 0.01 | −0.4 |

TABLE 11-continued

| Example No. | amount mixed with feed (%) | GHb change (%) |
|---|---|---|
| Example 3 | 0.03 | −0.3 |
| Example 4 | 0.03 | −0.7 |
| Example 5 | 0.03 | −0.3 |
| control group | — | 0.8 |

As shown in Table 11, the test compound lowered the glycated hemoglobin level of KKA$^y$ mouse. From the above results, it was confirmed that a compound having a muscle cell differentiation promoting or/and adipocyte differentiation suppressive action has a superior anti-diabetes action.

Experimental Example 6

Evaluation of Adipocyte Differentiation Suppressive Action

3T3-L1 cells (ATCC) were cultured in a growth medium until confluence. 1 μM dexamethasone, 0.5 mM 3-isobutyl-1-methylxanthine and 5 μg/mL insulin were added to the medium, and the cells were cultured for 3 days. The medium was exchanged with a growth medium containing 4 μg/mL insulin and the cells were cultured for 3 more days. When the compound (1 μM) was to be added, it was added after the cells reached confluence, and the cells were cultured for 6 days. After completion of the culture period, the fat droplet formed was quantified using Adipogenesis Assay Kit (CHEMICON). The numerical values in Table 12 show the relative value when without addition of the compound as 100% (n is the number of samples).

TABLE 12

| compound  | lipid accumulation (%) |
|-----------|------------------------|
| Example 1 | 53                     |
| Example 2 | 45                     | n = 2

As shown in Table 12, it was confirmed that the compounds of Example 1 and Example 2 decrease the lipid accumulation amount in the cell in fat differentiation and have an adipocyte differentiation suppressive action.

Formulation Example 1

Production of Capsule

| 1) compound of Example 1        | 30 mg |
|---------------------------------|-------|
| 2) finely divided powder cellulose | 10 mg |
| 3) lactose                      | 19 mg |
| 4) magnesium stearate           | 1 mg  |
| total                           | 60 mg |

1), 2), 3) and 4) are mixed and filled in a gelatin capsule.

Formulation Example 2

Production of Tablet

| 1) compound of Example 1           | 30 g  |
| 2) lactose                         | 50 g  |
| 3) cornstarch                      | 15 g  |
| 4) calcium carboxymethylcellulose  | 44 g  |
| 5) magnesium stearate              | 1 g   |
| 1000 tablets total                 | 140 g |

The total amount of 1), 2), 3) and 30 g of 4) are kneaded with water, vacuum dried and sieved.

The sieved powder is mixed with 14 g of 4) and 1 g of 5), and the mixture is tableted by a tableting machine. As a result, 1000 tablets containing 30 mg of the compound of Example 1 are obtained.

INDUSTRIAL APPLICABILITY

The compound of the present invention has a muscle cell or adipocyte differentiation regulating action, and is useful for the prophylaxis or treatment of diseases such as diabetes, obesity, dyslipidemia and the like, and the like.

This application is based on patent application No. 2010-160240 filed in Japan, the contents of which are encompassed in full herein.

The invention claimed is:

1. A compound represented by the formula (I):

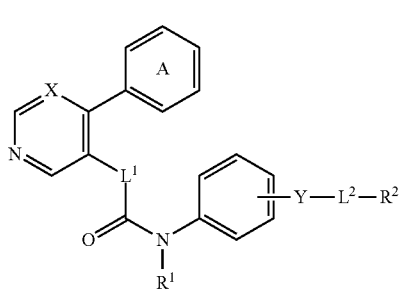

wherein

A is an optionally substituted benzene ring,

X is CH or N,

Y is a bond, —O— or —S—, $L^1$ is a $C_{2-6}$ alkenylene group, $L^2$ is a $C_{1-6}$ alkylene group, a $C_{2-6}$ alkenylene group or a $C_{2-6}$ alkynylene group, $R^1$ is a hydrogen atom or a $C_{1-6}$ alkyl group, $R^2$ is (1) a 5- or 6-membered aromatic heterocyclic group optionally substituted by 1 to 3 substituents selected from a halogen atom, a $C_{1-6}$ alkyl group and a $C_{1-6}$ alkoxy group, (2) a fused aromatic heterocyclic group of a benzene ring and a 5- or 6-membered heterocycle, wherein the fused aromatic heterocyclic group is optionally substituted by 1 to 3 substituents selected from a halogen atom, a $C_{1-6}$ alkyl group and a $C_{1-6}$ alkoxy group, (3) —PO(OR$^3$)$_2$ or (4) —S(O)$_m$R$^4$, $R^3$ is a $C_{1-6}$ alkyl group, $R^4$ is a $C_{1-6}$ alkyl group, and m is 0, 1 or 2, or a salt thereof.

2. The compound or salt of claim 1, wherein $L^2$ is a $C_{1-6}$ alkylene group.

3. The compound or salt of claim 1, wherein A is a benzene ring optionally substituted by 1 to 3 substituents selected from a $C_{1-6}$ alkoxy group and a halogen atom.

4. The compound or salt of claim 1, wherein Y is a bond or —O—.

5. The compound or salt of claim 1, wherein $R^2$ is (1) imidazolyl or oxadiazolyl, each of which is optionally substituted by 1 to 3 $C_{1-6}$ alkyl groups, (2) benzimidazolyl optionally substituted by 1 to 3 $C_{1-6}$ alkyl groups, (3) —PO(OCH$_3$)$_2$ or —PO(OC$_2$H$_5$)$_2$ or (4) —S(O)$_2$CH$_3$.

6. The compound or salt of claim 1, wherein R is imidazol-1-yl, benzimidazol-1-yl or 1,3,4-oxadiazol-2-yl, each of which is optionally substituted by $C_{1-6}$ alkyl group (s).

7. The compound or salt of claim 1, which is represented by the formula (II):

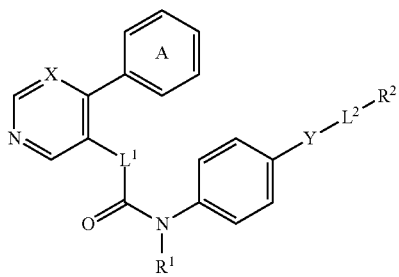

(II)

wherein each symbol is as defined in claim 1.

8. The compound or salt of claim 1, which is represented by the formula (II):

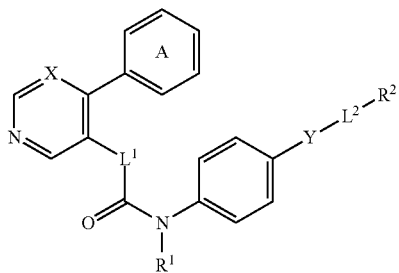

(II)

wherein

A is a benzene ring optionally substituted by 1 to 3 substituents selected from a $C_{1-6}$ alkoxy group and a halogen atom, X is CH or N, Y is a bond or —O—, $L^1$ is a $C_{2-6}$ alkenylene group, $L^2$ is a $C_{1-6}$ alkylene group, $R^1$ is a hydrogen atom, and $R^2$ is (1) imidazol-1-yl or 1,3,4-oxadiazol-2-yl, each of which is optionally substituted by 1 to 3 $C_{1-6}$ alkyl groups, (2) benzimidazol-1-yl optionally substituted by 1 to 3 $C_{1-6}$ alkyl groups, (3) —PO(OCH$_3$)$_2$ or —PO(OC$_2$H$_5$)$_2$, or (4) —S(O)$_2$CH$_3$.

9. (2E)-3-[4-(4-Fluorophenyl)pyridin-3-yl]-N-{4-[2-(1,3,4-oxadiazol-2-yl)ethyl]phenyl}prop-2-enamide or a salt thereof.

10. (2E)-3-[4-(4-Fluorophenyl)pyrimidin-5-yl]-N-{4-[2-(1,3,4-oxadiazol-2-yl)ethyl]phenyl}prop-2-enamide or a salt thereof.

11. A pharmaceutical composition comprising the compound or salt of claim 1 and a pharmacologically acceptable carrier.

* * * * *

UNITED STATES PATENT AND TRADEMARK OFFICE
CERTIFICATE OF CORRECTION

PATENT NO. : 8,937,055 B2
APPLICATION NO. : 13/810021
DATED : January 20, 2015
INVENTOR(S) : Osamu Ujikawa et al.

It is certified that error appears in the above-identified patent and that said Letters Patent is hereby corrected as shown below:

In the Claims

Line 65 in column 62 that reads: "6. The compound or salt of claim 1, wherein R is imidazol-" should be changed to -- 6. The compound or salt of claim 1, wherein $R^2$ is imidazol- --.

Signed and Sealed this
Thirtieth Day of June, 2015

Michelle K. Lee
*Director of the United States Patent and Trademark Office*